US012653917B2

(12) United States Patent
Lim et al.

(10) Patent No.: US 12,653,917 B2
(45) Date of Patent: Jun. 16, 2026

(54) PLASMA TREATMENT APPARATUS AND METHOD USING SAME

(71) Applicant: PLASMAPP CO., LTD., Daejeon (KR)

(72) Inventors: You Bong Lim, Daejeon (KR); Seung Hun Lee, Daejeon (KR); Jun Young Kim, Daejeon (KR)

(73) Assignee: PLASMAPP CO., LTD., Daejeon (KR)

( * ) Notice: Subject to any disclaimer, the term of this patent is extended or adjusted under 35 U.S.C. 154(b) by 731 days.

(21) Appl. No.: 17/928,847

(22) PCT Filed: May 28, 2021

(86) PCT No.: PCT/KR2021/006695
   § 371 (c)(1),
   (2) Date: Nov. 30, 2022

(87) PCT Pub. No.: WO2021/246727
   PCT Pub. Date: Dec. 9, 2021

(65) Prior Publication Data
   US 2023/0226236 A1      Jul. 20, 2023

(30) Foreign Application Priority Data

Jun. 1, 2020    (KR) ........................ 10-2020-0065842
   Jun. 18, 2020   (KR) ........................ 10-2020-0074260
   (Continued)

(51) Int. Cl.
   *A61L 2/14*          (2006.01)
   *A61L 2/24*          (2006.01)
   (Continued)

(52) U.S. Cl.
   CPC .................. *A61L 2/24* (2013.01); *A61L 2/14* (2013.01); *A61L 2/26* (2013.01); *A61L 2202/11* (2013.01);
   (Continued)

(58) Field of Classification Search
   CPC ........................................................ A61L 2/14
   See application file for complete search history.

(56) References Cited

U.S. PATENT DOCUMENTS

2018/0138022 A1      5/2018   Lam et al.
2019/0374327 A1     12/2019   Lam et al.

FOREIGN PATENT DOCUMENTS

CN         109504970 A       3/2019
CN         110402121 A      11/2019
   (Continued)

OTHER PUBLICATIONS

English Translation provided by the United States Patent Office Search Tool PE2E Search: Lee, Seunghoon; Low Temperature Plasma Device For Surface Treatment; Feb. 10, 202 (Year: 2020).*
   (Continued)

*Primary Examiner* — Kevin Joyner
(74) *Attorney, Agent, or Firm* — Sughrue Mion, PLLC

(57) ABSTRACT

The present disclosure relates to a plasma treatment apparatus and a method using the same, and more particularly, to a plasma treatment apparatus for applying, to a target object, such as a biomaterial, characteristics (e.g., removal of organic materials, crosslinking reaction, etching reaction, structural change by surface chemical reaction, sterilization effect, wettability, adhesiveness, bondability, color compatibility, surface reinforcement, modification of surface heat resistance, sterilization, removal of harmful proteins/bacteria, etc.) according to plasma treatment, and a method using the plasma treatment apparatus.

13 Claims, 34 Drawing Sheets

(30)       Foreign Application Priority Data

| | | | |
|---|---|---|---|
| Jul. 15, 2020 | (KR) | ........................ | 10-2020-0087734 |
| Sep. 25, 2020 | (KR) | ........................ | 10-2020-0124911 |
| Apr. 26, 2021 | (KR) | ........................ | 10-2021-0053970 |

(51) Int. Cl.

| | |
|---|---|
| *A61L 2/26* | (2006.01) |
| *H05H 1/24* | (2006.01) |

(52) U.S. Cl.

CPC ..... *A61L 2202/122* (2013.01); *A61L 2202/14* (2013.01)

(56)       References Cited

FOREIGN PATENT DOCUMENTS

| | | | |
|---|---|---|---|
| JP | 6410924 | B2 | 10/2018 |
| KR | 10-2001-0104380 | A | 11/2001 |

| | | | | | |
|---|---|---|---|---|---|
| KR | 10-2011-0071111 | A | | 6/2011 | |
| KR | 10-2012-0039729 | A | | 4/2012 | |
| KR | 10-1439344 | B1 | | 9/2014 | |
| KR | 10-2014-0132347 | A | | 11/2014 | |
| KR | 10-1483431 | B1 | | 1/2015 | |
| KR | 10-2017-0017023 | A | | 2/2017 | |
| KR | 10-1705830 | B1 | | 2/2017 | |
| KR | 10-2018-0015053 | A | | 2/2018 | |
| KR | 10-2019-0030520 | A | | 3/2019 | |
| KR | 10-2036169 | B1 | | 10/2019 | |
| KR | 10-2064955 | B1 | | 1/2020 | |
| KR | 20200014166 | A | * | 2/2020 | .......... A61C 8/0087 |
| KR | 10-2169548 | B1 | | 10/2020 | |
| WO | 2018/164497 | A1 | | 9/2018 | |

OTHER PUBLICATIONS

International Search Report for PCT/KR2021/006695, dated Sep. 2, 2021.

* cited by examiner

CONTROL

Plasma treated and contained in the vacuum

| | |
|---|---|
| Accommodate accommodation container | S610 |
| Generate path communicating with inside of container | S620 |
| Exhaust internal air of container | S630 |
| Apply electric power for generating plasma to container | S640 |
| Vent inside of container | S650 |

FIG. 31

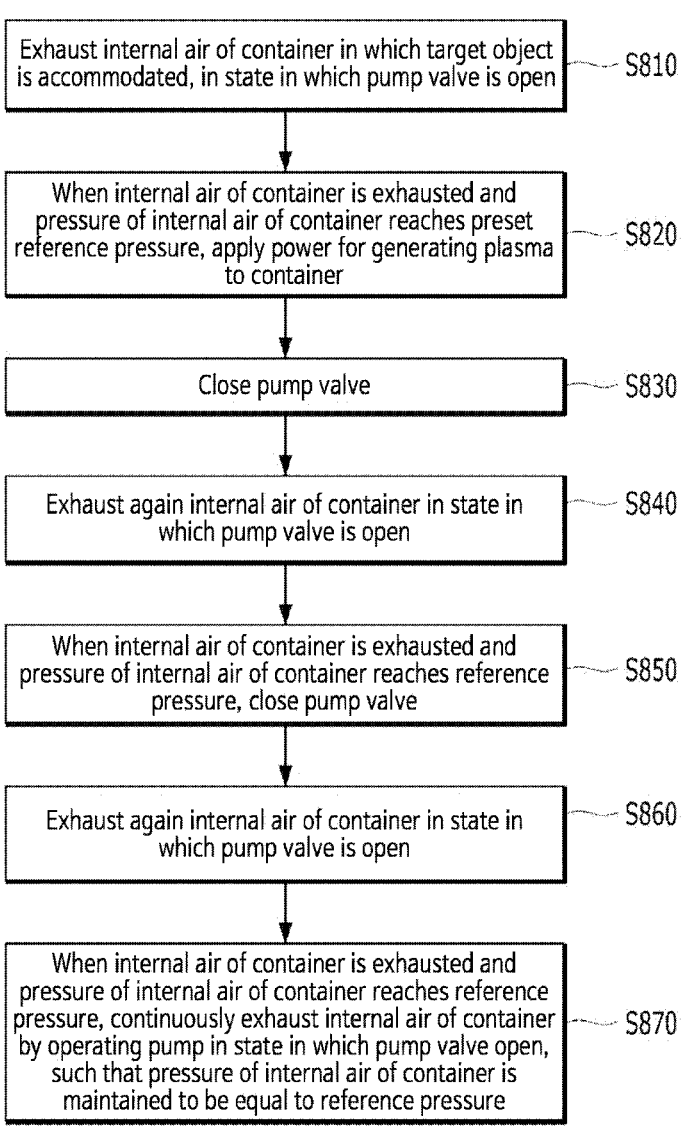

Exhaust internal air of container in which target object is accommodated, in state in which pump valve is open ~ S810

When internal air of container is exhausted and pressure of internal air of container reaches preset reference pressure, apply power for generating plasma to container ~ S820

Close pump valve ~ S830

Exhaust again internal air of container in state in which pump valve is open ~ S840

When internal air of container is exhausted and pressure of internal air of container reaches reference pressure, close pump valve ~ S850

Exhaust again internal air of container in state in which pump valve is open ~ S860

When internal air of container is exhausted and pressure of internal air of container reaches reference pressure, continuously exhaust internal air of container by operating pump in state in which pump valve open, such that pressure of internal air of container is maintained to be equal to reference pressure ~ S870

PLASMA TREATMENT APPARATUS AND METHOD USING SAME

TECHNICAL FIELD

The present disclosure relates to a plasma treatment apparatus and a method using the same, and more particularly, to a plasma treatment apparatus for applying, to a target object, such as a biomaterial, characteristics (e.g., removal of organic materials, crosslinking reaction, etching reaction, structural change by surface chemical reaction, sterilization effect, wettability, adhesiveness, bondability, color compatibility, surface reinforcement, modification of surface heat resistance, sterilization, removal of harmful proteins/bacteria, etc.) according to plasma treatment, and a method using the plasma treatment apparatus.

In addition, the present disclosure relates to a plasma treatment container including a cover, in which an implant body is accommodated and connected to the cover to keep airtight an internal gas environment filled with discharge gas used for plasma discharge according to a preset composition ratio.

In addition, the present disclosure relates to a plasma treatment container including an exhaust unit having a passage for exhausting internal gas of a storage container storing contents, in a state in which the exhaust unit is coupled to and thus inserted into the storage container, and a plasma treatment method using the plasma treatment container.

BACKGROUND ART

Plasma treatment is used for various purposes in various industries, such as semiconductor, display, agriculture, and medical industries.

In the field of agriculture, plasma treatment is applicable to sterilization and promotion of germination of seeds using nonthermal plasma. Such plasma treatment may have a sterilization effect on microorganisms present on the surface of a sprout by performing nonthermal plasma directly on the surface of a seed, and an effect of reducing a time period required for germination by increasing the rate and speed of germination of sprouted seeds, thus reducing a time period required for agricultural production, and providing safer food.

In addition, with the recent development of the medical industry, plasma treatment has been used in various ways, and has been used to increase biocompatibility in implantation of biomaterials, such as implants.

In particular, in dentistry, a treatment for implanting an artificial tooth (generally referred to as an implant) to replace a tooth that is extracted due to tooth decay or other reasons is used.

An implant refers to a replacement for restoring lost human tissue, and in dentistry, refers to an artificial tooth structure.

In an implant procedure, an artificial tooth root made of a material that is not rejected by a human body (e.g., titanium) is implanted in a bone to replace the tooth root of a lost tooth. Thereafter, the artificial tooth root is adhered to the alveolar bone, and a prosthesis is fixed to form an artificial tooth structure.

In general, a dental implant consists of a fixture made of titanium and implanted in an alveolar bone, an abutment fixed onto the fixture to support a prosthesis, an abutment screw to fix the abutment onto the fixture, and the prosthesis as an artificial tooth fixed to the abutment.

An implant to be used as an artificial tooth is made of a material that is not rejected by a human body, and is used for cosmetic purposes for a part without bones and gums as well as for restoring functions of the part.

In such treatment, a fixture corresponding to an implant is planted in an alveolar bone from which a tooth has been extracted, and then fixed to restore the function of the tooth.

Here, the procedure includes a primary procedure of implanting the fixture in the alveolar bone, and a secondary procedure of fixing a crown, which is the final prosthesis, after waiting for 3 months or longer for the fixture to osseointegrate with the alveolar bone.

The components of a dental implant are to be inserted into human tissues, and thus need to be kept sterilized and surface-activated, and accordingly, preventing the components from being contaminated or damaged in packaging, transporting, and opening the package has been the most important task.

Commonly used fixtures are mainly made of a titanium metal or a titanium alloy, and in transplanting such materials into a human body, it takes a long time for osteointegration, and, as an oxide film is formed, stability may be secured compared to other metals, but there is a need for more improved human body stability.

In order to compensate for such disadvantages, technologies for enhancing osseointegration by appropriately treating the surface of titanium and titanium alloy materials have been developed and applied.

The rate and quality of osseointegration are closely related to the surface properties and chemical composition of an implant, such as surface composition, surface roughness, or hydrophilicity. In particular, it is known that an implant having a highly hydrophilic surface is advantageous for interaction with body fluids, cells, and tissues.

In a production stage of an implant, hydrophilicity may be secured through a plasma surface treatment process. However, due to the formation of an oxide film during production, transportation, distribution, and storage, hydrophilicity changes over time to hydrophobicity, and accordingly, it is difficult to secure existing biocompatibility.

Therefore, in order to solve a related-art issue of changes with the passage of time, techniques for securing biocompatibility through surface treatment of a fixture before an implant procedure with simple equipment are being developed. Representative examples of such techniques include those for improving hydrophilicity and osseointegration efficiency by performing plasma surface treatment and ultraviolet irradiation.

However, medical devices that are to be inserted into a human body, such as implants, require assurance of sterility, but in performing plasma surface treatment or ultraviolet irradiation, as aseptic packaging materials of a fixture is removed and then the fixture is handled while being exposed to an external environment, sterility cannot be assured, and an object to be treated may be contaminated.

Ultraviolet irradiation solves the above issue by using, as a case, a quartz tube capable of securing the transmission of ultraviolet rays, and positioning and processing an object to be treated therein, but there are issues in terms of cost in using an expensive quartz tube and inconvenient management being required, and because the object to be treated in the quartz tube is isolated in terms of heat flow, heat generated by ultraviolet treatment may not escape, and thus, the object may be thermally damaged.

In the related-art plasma treatment, it is difficult to assure sterility due to removal of aseptic packaging materials and fastening to a particular electrode connection part that are performed for surface treatment of a fixture.

In addition, the related-art method of generating plasma in an atmospheric pressure environment for treatment has an issue that plasma treatment performance is not constant, and high energy is locally delivered, resulting in damage to an object to be treated and deterioration in the performance of a fixture.

The related-art plasma treatment method has an issue that plasma generation and surface treatment are not spatially uniform because the surface treatment is performed at atmospheric pressure. In order to improve this, there has been a method of supplying a gas, such as helium or argon, to a space for plasma surface treatment for the purpose of improving spatial uniformity of the plasma surface treatment. However, this method has a limitation in that the gas needs to be continuously supplied, and there is an issue that the sterility of the supplied gas needs to be secured.

Even when the sterility is assured in a process of surface treatment of an implant, the deposition of organic materials, such as hydrocarbons (CHx) in the air, cause a change over time to hydrophobicity, which makes it difficult to maintain biocompatibility obtained through the surface treatment.

Accordingly, a surface treatment technique cannot be applied in a production stage, and even in a case in which surface treatment is performed before an implant procedure, there is an issue of a relatively short storage process, or that the maintenance performance of biocompatibility obtained from the surface treatment is deteriorated during the storage process.

Meanwhile, plasma surface treatment may create various effects on a surface-treated object.

In a case of surface treatment of a bone graft material, the bone cell adhesion and transplantation characteristics on the surface of the bone graft material are improved, and thus, the biocompatibility of the bone graft material increases.

In a case of surface treatment of plant seeds, the rate or speed of germination of the surface-treated plant seeds may be improved.

As such, for a case in which plasma surface treatment of various types of materials is required, there is a need for a technique for effectively performing surface treatment of contents regardless of the type of the contents.

DISCLOSURE

Technical Problem

A technical object to be achieved by the present disclosure is to provide a plasma treatment apparatus for applying, to a target object, such as a biomaterial, characteristics according to plasma treatment, and a method using the plasma treatment apparatus.

Another technical object to be achieved by the present disclosure is to provide a plasma treatment apparatus that is simplified by applying electricity to an target object to replace a high-voltage part for generating plasma, and a method using the plasma treatment apparatus.

Another technical object to be achieved by the present disclosure is to provide a plasma treatment apparatus that is modified such that the side of a connection unit of the apparatus for applying electricity to a target object is in line contact or surface contact with the target object or its connection member, so as to prevent damage caused when the connection unit is in point contact with the target object, and a method using the plasma treatment apparatus.

Another technical object to be achieved by the present disclosure is to provide a plasma treatment apparatus capable of creating a vacuum in a plasma treatment space so as to ensure sterility of the plasma treatment space, and a method using the plasma treatment apparatus.

Another technical object to be achieved by the present disclosure is to provide a plasma treatment apparatus capable of maintaining sterility and biocompatibility through storage in a vacuum state after plasma surface treatment is completed, and a method using the plasma treatment apparatus.

Another technical object to be achieved by the present disclosure is to provide a plasma treatment apparatus for preventing contamination in a process of moving a fixture to a vacuum chamber for performing surface treatment using plasma in a vacuum, and a method using the plasma treatment apparatus.

Another technical object to be achieved by the present disclosure is to provide a plasma treatment container including a cover, in which an implant body is accommodated and connected to the cover to keep airtight an internal gas environment filled with discharge gas used for plasma discharge according to a preset composition ratio.

Another technical object to be achieved by the present disclosure is to provide a plasma treatment container including an exhaust unit having a passage for exhausting internal gas of a storage container storing contents, in a state in which the exhaust unit is coupled to and thus inserted into the storage container, and a plasma treatment method using the plasma treatment container.

Technical Solution

A plasma treatment apparatus according to an embodiment of the present disclosure may include: an accommodation unit to accommodate a container in which a target object is accommodated; a first electrode unit in contact with the target object; a second electrode unit adjacent to an outer circumferential surface of the container; and a power supply unit to apply a voltage to the target object through the first electrode unit to generate plasma in the container.

In some embodiments, the accommodation unit may be provided with an insertion groove into which the container is inserted and accommodated, and the second electrode unit may be provided inside a sidewall of the insertion groove.

In some embodiments, upper and lower lengths of the target object may be less than or equal to upper and lower lengths of the second electrode unit, such that upper and lower regions of the target object are located within upper and lower regions of the second electrode unit, respectively, when the plasma is generated in the container.

In some embodiments, the plasma treatment apparatus may further include a dielectric between the container and the second electrode unit.

In some embodiments, the plasma treatment apparatus may further include an exhaust unit connected to the accommodation unit to exhaust internal air of the container, and the exhaust may include: a path generation unit to generate a path communicating with an inside of the container; and a pump to exhaust the internal air of the container through the path.

In some embodiments, the path generation unit may include a needle to generate the path by piercing one surface of the container.

A plasma treatment apparatus according to another embodiment of the present disclosure may include: first and second accommodation units to accommodate first and second containers in which first and second target objects are accommodated, respectively; an independent exhaust unit, which is connected to each of the first and second accommodation units and includes an exhaust pump and a pump valve to exhaust internal air of the first and second containers; and first and second treatment units to apply electric power for generating plasma, respectively to the first and second containers from which the internal air is exhausted by the independent exhaust unit.

In some embodiments, the plasma treatment apparatus may further include: a housing, which surrounds the first and second accommodation units and packs the first and second accommodation units to be independent of the independent exhaust unit; and a connection unit to connect the housing to the independent exhaust unit such that the housing and the independent exhaust unit are arranged independently of each other.

In some embodiments, the plasma treatment apparatus may further include: a first path generation unit, which includes a first needle to generate a first path for exhausting the internal air of the first container, by piercing one surface of the first container, and is connected to the connection unit; and a second path generation unit, which includes a second needle to generate a second path for exhausting the internal air of the second container, by piercing one surface of the second container, and is connected to the connection unit.

In some embodiments, the first and second treatment units may simultaneously or separately apply electric power to the first and second containers, respectively, such that the first and second target objects are simultaneously or separately plasma-treated.

In some embodiments, the first electrode unit may include a contact unit to be inserted into the container such that a side of the contact unit is electrically connected to the target object.

In some embodiments, the contact unit may include a tip capable of penetrating an outer surface of the container.

In some embodiments, the contact unit may include an air flow path therein for exhausting the internal air of the container.

In some embodiments, the accommodation unit may read information of a display unit provided in the container, and determine, through display unit provided in the container, at least one of whether the container is accurately accommodated in a target position, whether the container is a genuine product, the number of times the container is used for plasma treatment, a type of the container, and a type of the target object accommodated in the container.

In some embodiments, the accommodation unit may read information of a display unit provided in the container to determine an internal environment of the container, and the power supply unit may apply a voltage by varying a voltage condition according to the determined internal environment.

A plasma treatment method according to an embodiment of the present disclosure may include: exhausting internal air of a container in which a target object is accommodated; and when the internal air of the container is exhausted and a pressure of the internal air of the container reaches a preset reference pressure, applying, to the container, electric power for generating plasma in the container.

In some embodiments, in the applying of the electric power, the internal air of the container may be exhausted.

In some embodiments, in the applying of the electric power, an inside of the container may be closed.

In some embodiments, the plasma treatment method may further include, after the applying of the electric power, exhausting the internal air by releasing the closing of the container.

Advantageous Effects

Containers, apparatuses, and methods according to embodiments of the present disclosure have an effect of applying, to a target object, such as a biomaterial, characteristics according to plasma treatment.

In addition, the containers, apparatuses, and methods according to the embodiments of the present disclosure have an effect of simplifying an apparatus by allowing a target object to function as a high-voltage part for generating plasma by receiving electricity.

In addition, the containers, apparatuses, and methods according to the embodiments of the present disclosure have an effect of preventing a component of an apparatus to be a connection point for applying electricity to a target object from being damaged, and lowering the difficulty of an operation for making the connection point, by making the connection point to be line contact or surface contact rather than point contact.

In addition, the containers, apparatuses, and methods according to the embodiments of the present disclosure have an effect of performing uniform and stable plasma surface treatment in a vacuum, and having high spatial uniformity and improved surface treatment performance.

In addition, the containers, apparatuses, and methods according to the embodiments of the present disclosure have an effect of ensuring sterility of a plasma treatment space.

In addition, the containers, apparatuses, and methods according to the embodiments of the present disclosure have an effect of enabling vacuum sealing for maintaining sterilization and preventing damage and contamination of a plasma-treated object.

In addition, the containers, apparatuses, and methods according to the embodiments of the present disclosure have an effect of maintaining sterility and biocompatibility by enabling storage in a vacuum state after plasma surface treatment is completed.

In addition, the containers, apparatuses, and methods according to the embodiments of the present disclosure have an effect of preventing contamination in a process of moving a fixture to a vacuum chamber in performing surface treatment using plasma in a vacuum.

In addition, the apparatuses and methods according to the embodiments of the present disclosure have an effect of reducing the production costs by minimizing the configuration of a treatment apparatus.

In addition, the apparatuses and methods according to the embodiments of the present disclosure have an effect of increasing space efficiency as it is possible to change the arrangement by configuring a pump for exhaust as a separate device, and enabling systematical integrated installation with other apparatuses requiring exhaust.

In addition, the apparatuses and methods according to the embodiments of the present disclosure have an effect of simultaneously or individually treating a plurality of target objects.

In addition, the apparatuses and methods according to the embodiments of the present disclosure have an effect of not requiring the use of packaging using special materials in surface treatment that may ensure sterility.

The apparatuses and methods according to the embodiments of the present disclosure have an effect of maintaining airtightness for preventing contamination and damage and maintaining a sterilization state, with respect to an accommodated implant body.

In addition, the apparatuses and methods according to the embodiments of the present disclosure keep airtight an internal gas environment filled with discharge gas used for plasma discharge according to a preset composition ratio, and thus, a plasma treatment container in which an implant body is accommodated may be used for plasma treatment in an optimized state.

In addition, the apparatuses and methods according to the embodiments of the present disclosure may perform effective plasma treatment on an implant body as the implant body receiving a voltage applied thereto operates as one electrode used for dielectric barrier discharge.

In addition, the apparatuses and methods according to the embodiments of the present disclosure may effectively manage a plasma treatment container by displaying at least one of the type of discharge gas filled in the plasma treatment container, the composition ratio of the discharge gas, the internal pressure of the discharge gas, and the use-by date of the discharge gas, through a display unit outside the plasma treatment container.

The apparatuses and methods according to the embodiments of the present disclosure may effectively exhaust internal gas of a storage container and surface-treat contents by using an exhaust unit having a passage for exhausting the internal gas of the storage container storing the contents, in a state in which the exhaust unit is coupled to and thus inserted into the storage container.

In addition, the apparatuses and methods according to the embodiments of the present disclosure may improve the effect of surface treatment of contents, as an exhaust unit inserted into a storage container directly operates as a ground electrode or a power supply electrode.

In addition, the apparatuses and methods according to the embodiments of the present disclosure may minimize the phenomenon that contents are caught in an exhaust unit, as a hole for exhausting internal gas of a storage container is formed on the side of the exhaust unit.

In addition, the apparatuses and methods according to the embodiments of the present disclosure may maintain airtightness when or even after an external ground electrode or an external power supply electrode penetrates a plasma treatment container through an airtight unit.

In addition, the apparatuses and methods according to the embodiments of the present disclosure may maintain airtightness and sealing between a plasma treatment container and a storage container through a sealing unit.

DESCRIPTION OF DRAWINGS

FIG. 2 is a configuration diagram schematically illustrating a plasma treatment apparatus according to the second embodiment of the present disclosure.

Figure 3:
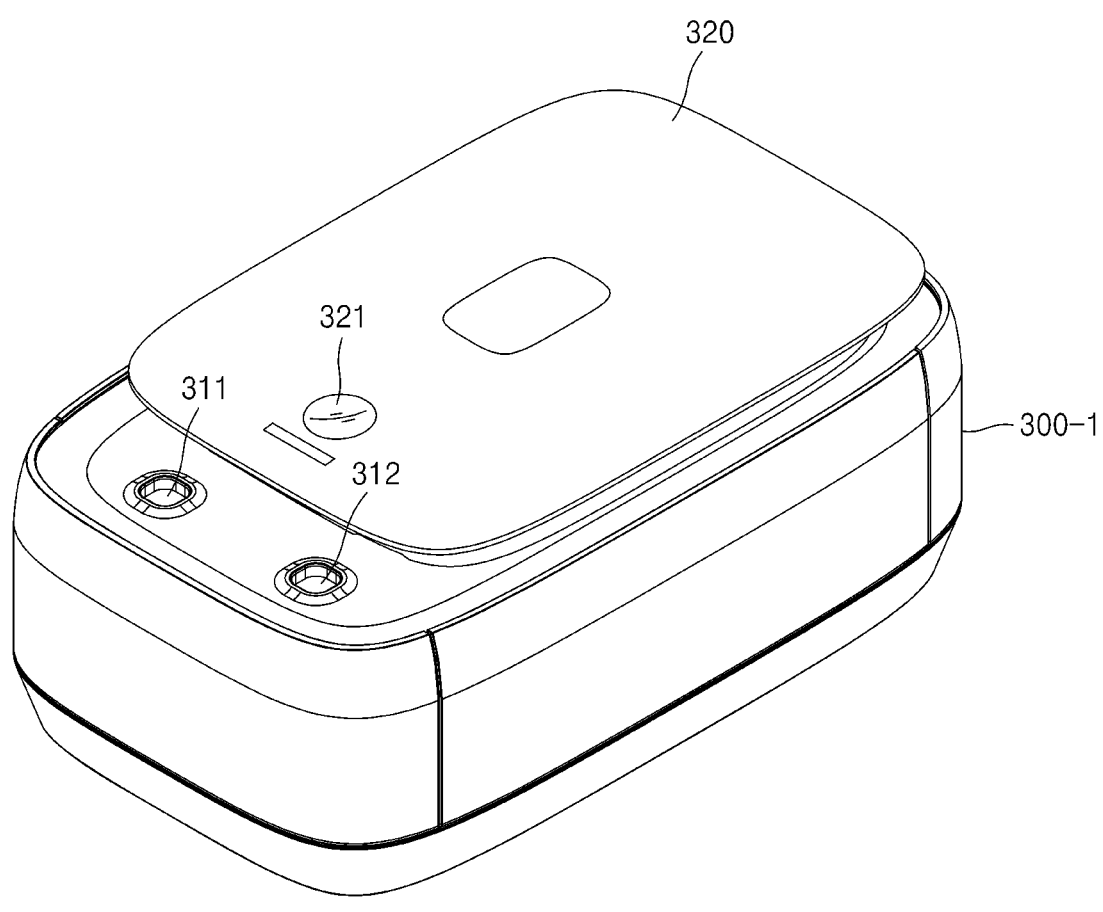
FIG. 3 is a perspective view of the front of a plasma treatment apparatus according to the third embodiment of the present disclosure.
Figure 5:
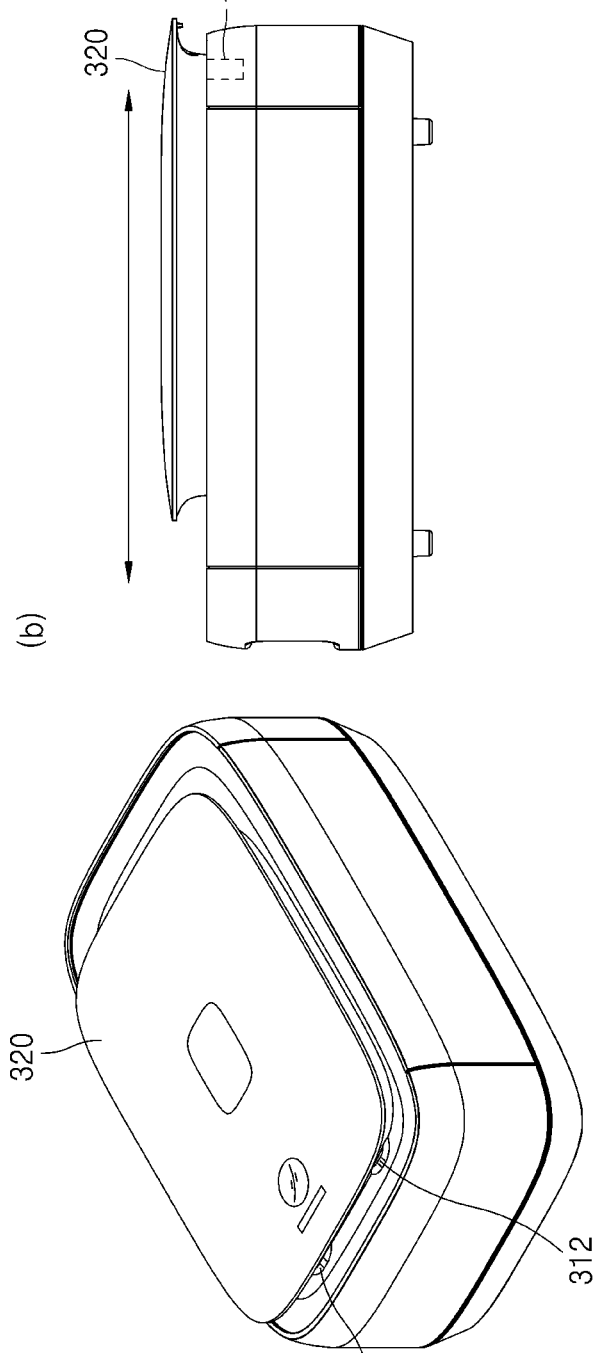

(a) of FIG. 5 is a perspective view of the closed plasma treatment apparatus of FIG. 3, and (b) of FIG. 5 is a side view thereof.

8

Figure 6:
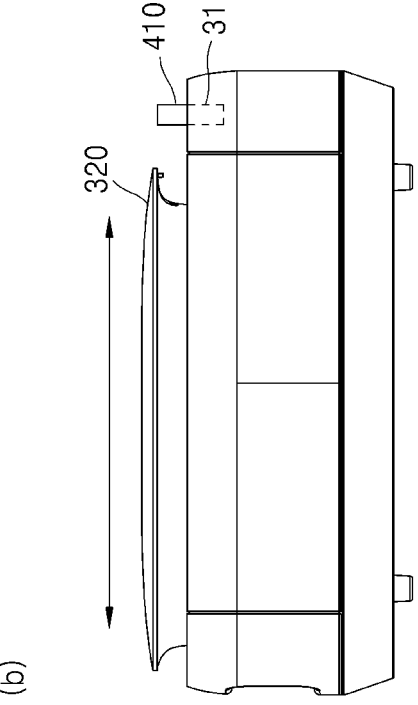
Figure 6:
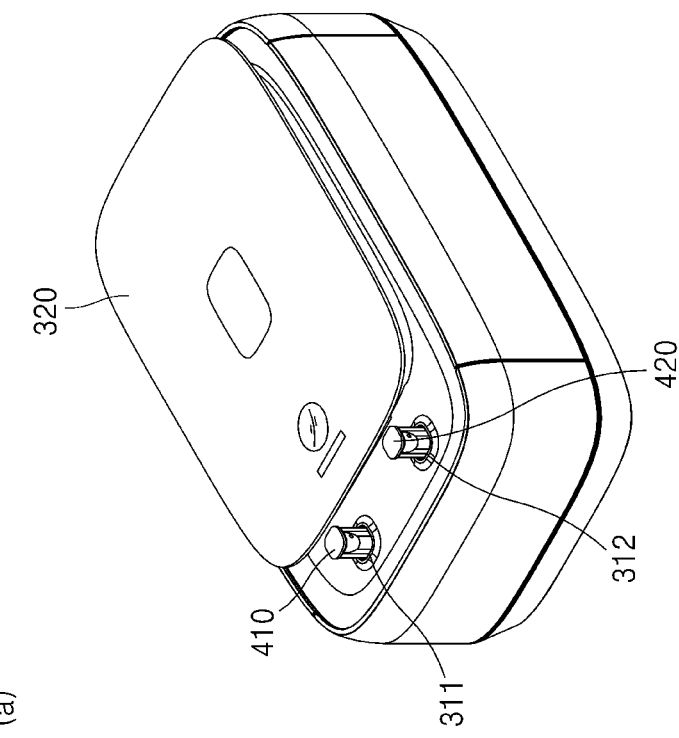

(a) of FIG. 6 is a perspective view of the open plasma treatment apparatus of FIG. 3, and (b) of FIG. 6 is a side view thereof.

Figure 7:
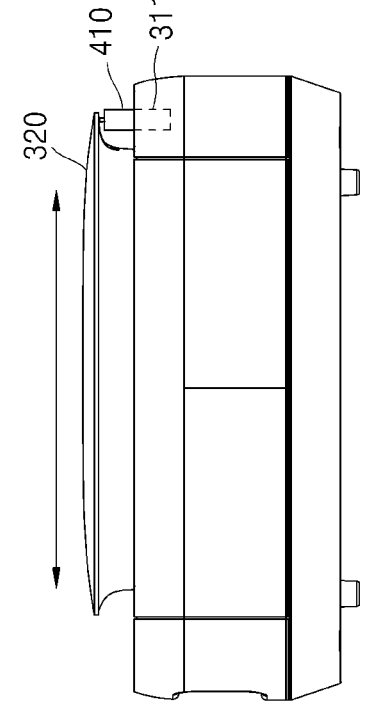
Figure 7:
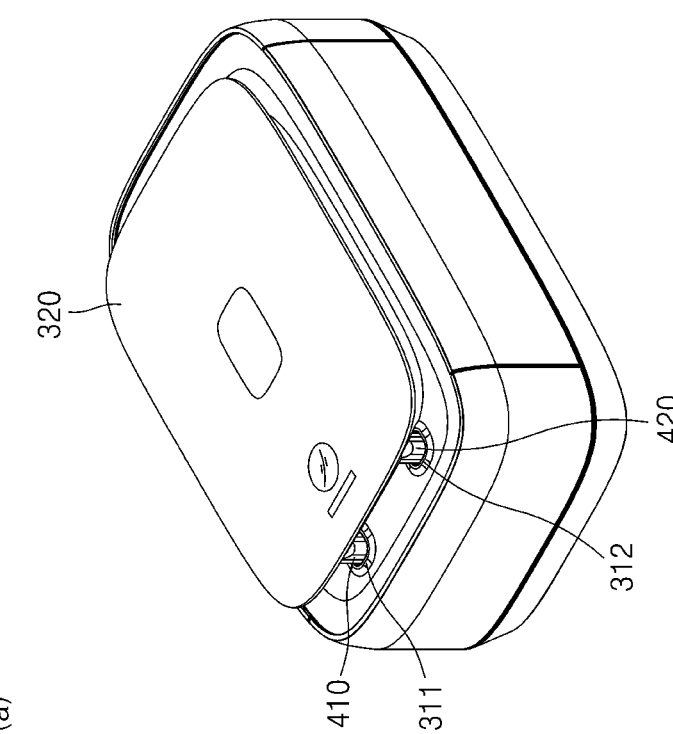

(a) of FIG. 7 is a perspective view of the plasma treatment apparatus of FIG. 3 that is operating, and (b) of FIG. 7 is a side view thereof.

Figure 8:
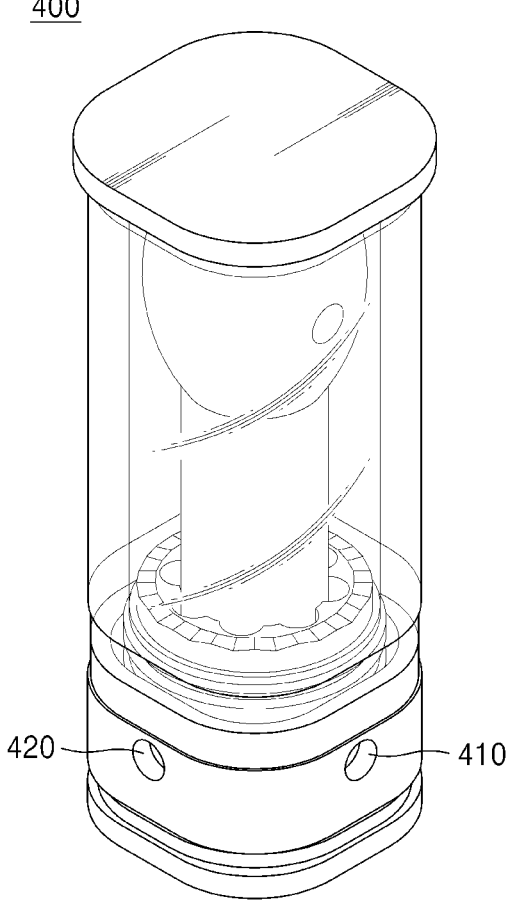

FIG. 8 is a configuration diagram schematically illustrating a container to be accommodated in the plasma treatment apparatus according to the third embodiment of the present disclosure.

FIGS. 9A to 9D show experimental results obtained by measuring carbon content when the surface of a target object is treated by using the plasma treatment apparatus according to the third embodiment of the present disclosure.

Figure 10:
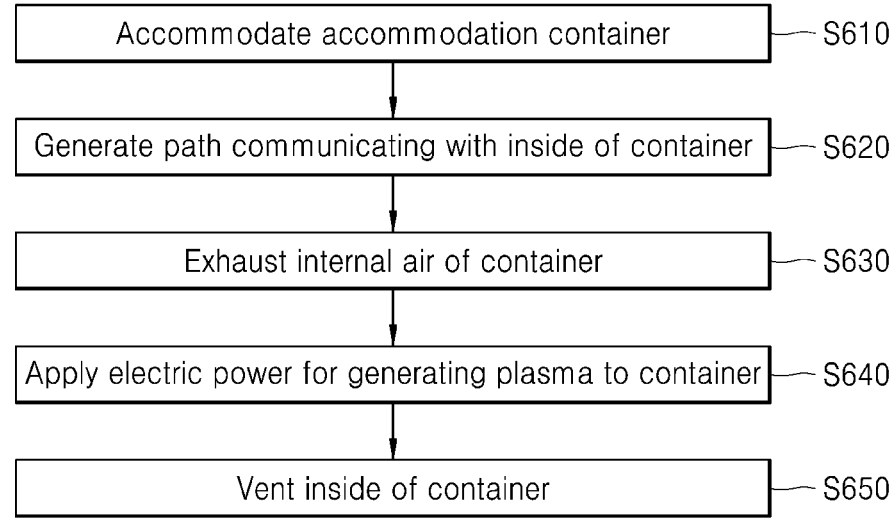

FIG. 10 is a flowchart illustrating a plasma treatment method according to the first embodiment of the present disclosure.

Figure 11:
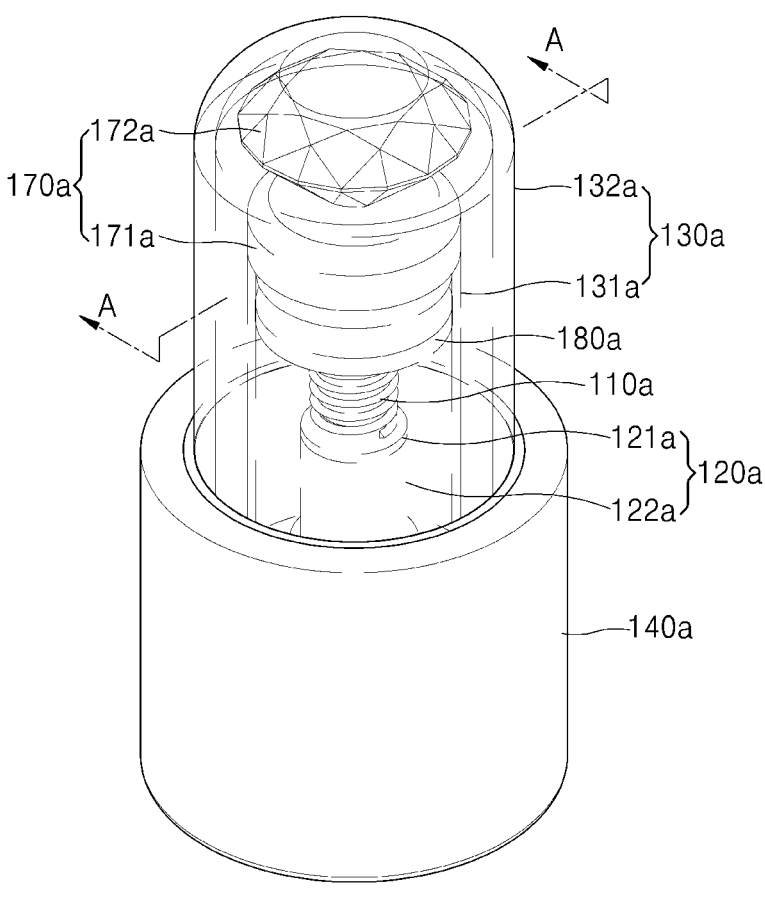

FIG. 11 is a configuration diagram schematically illustrating a plasma treatment container according to the first embodiment of the present disclosure.

Figure 12:
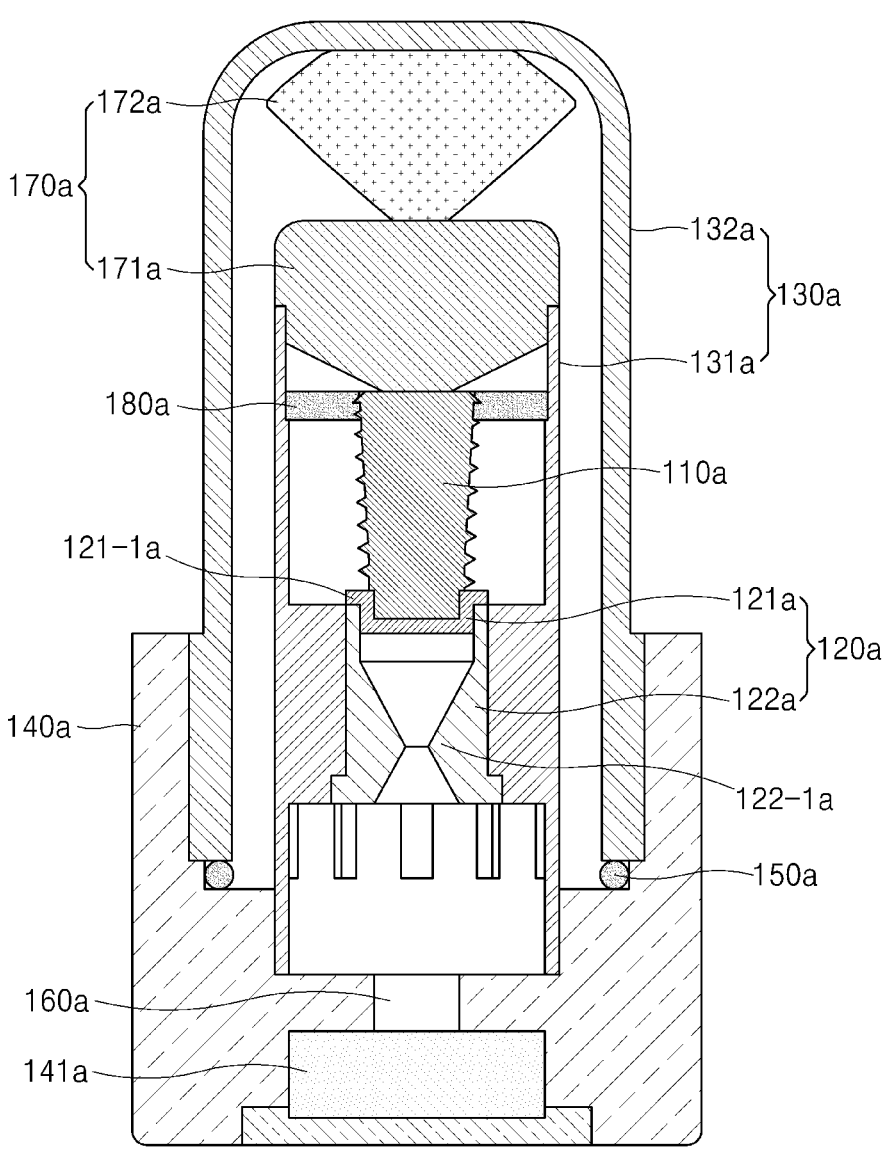

FIG. 12 is a schematic cross-sectional view taken along line AA of FIG. 11.

Figure 13:
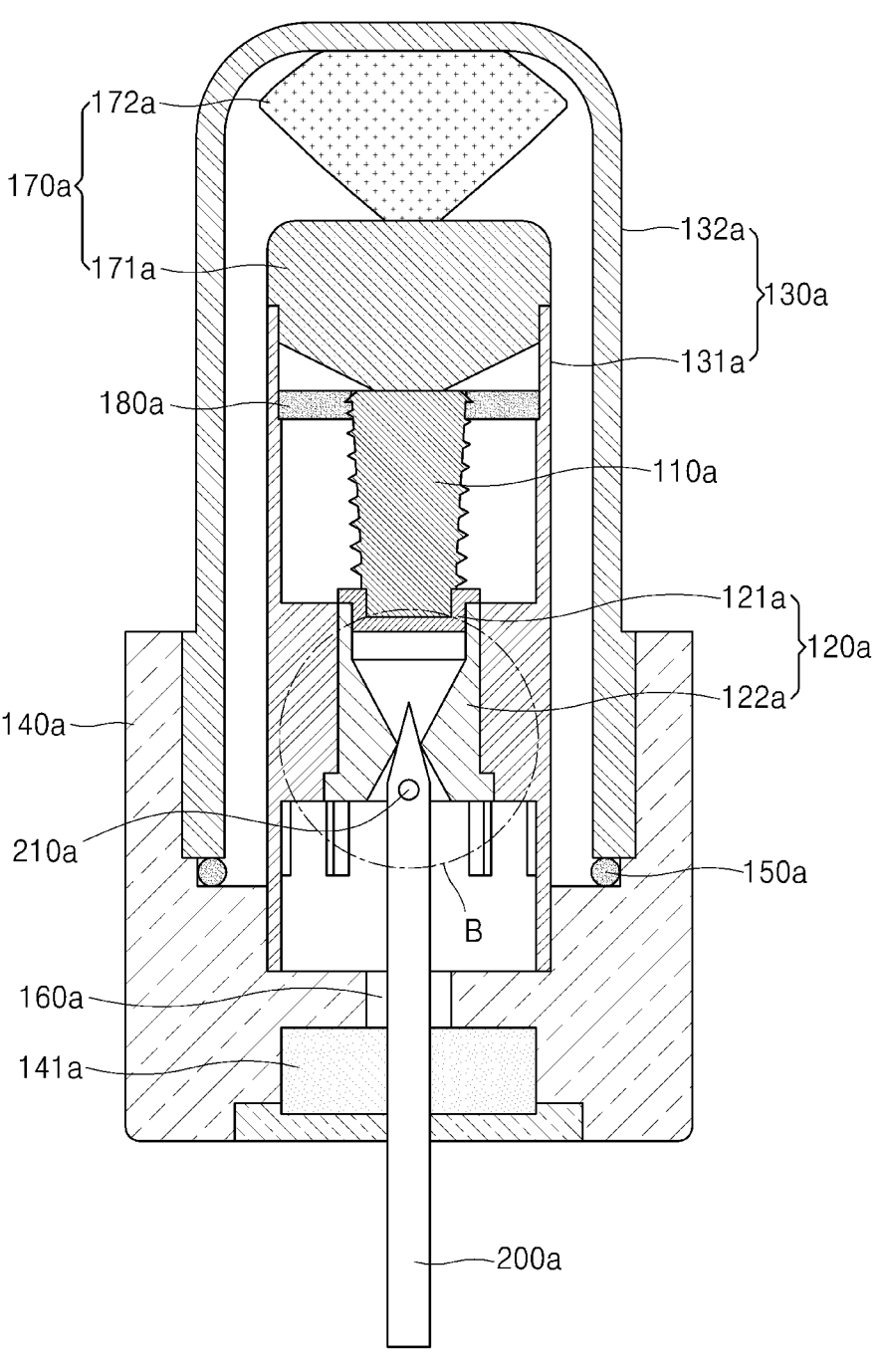

FIG. 13 is a schematic cross-sectional view illustrating a plasma treatment container when a contact unit is inserted thereinto in FIG. 12.

Figure 14:
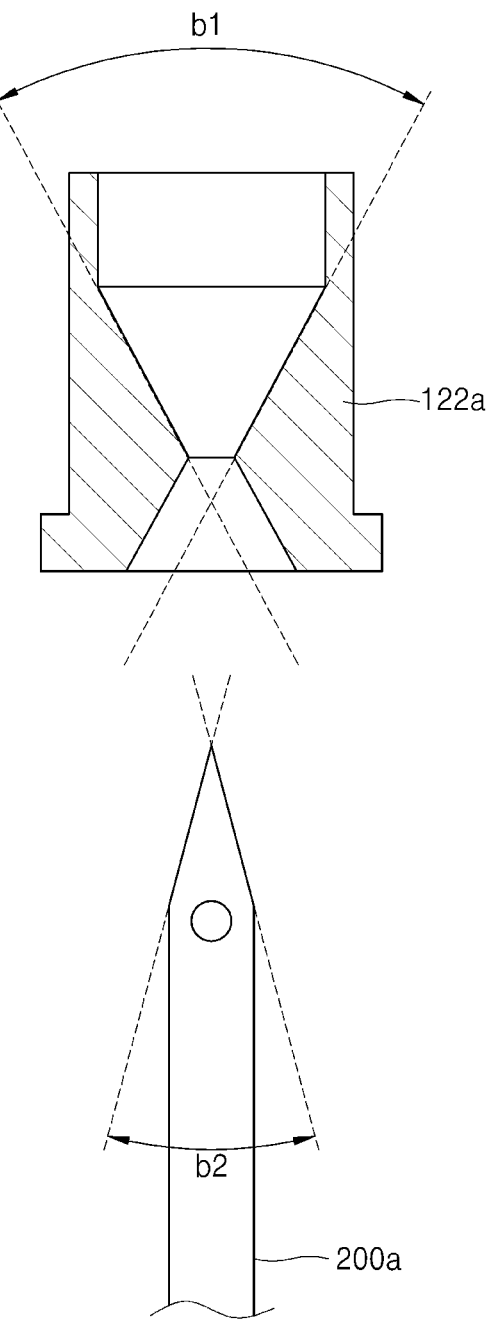

FIG. 14 is a diagram obtained by enlarging B of FIG. 13.

Figure 15:
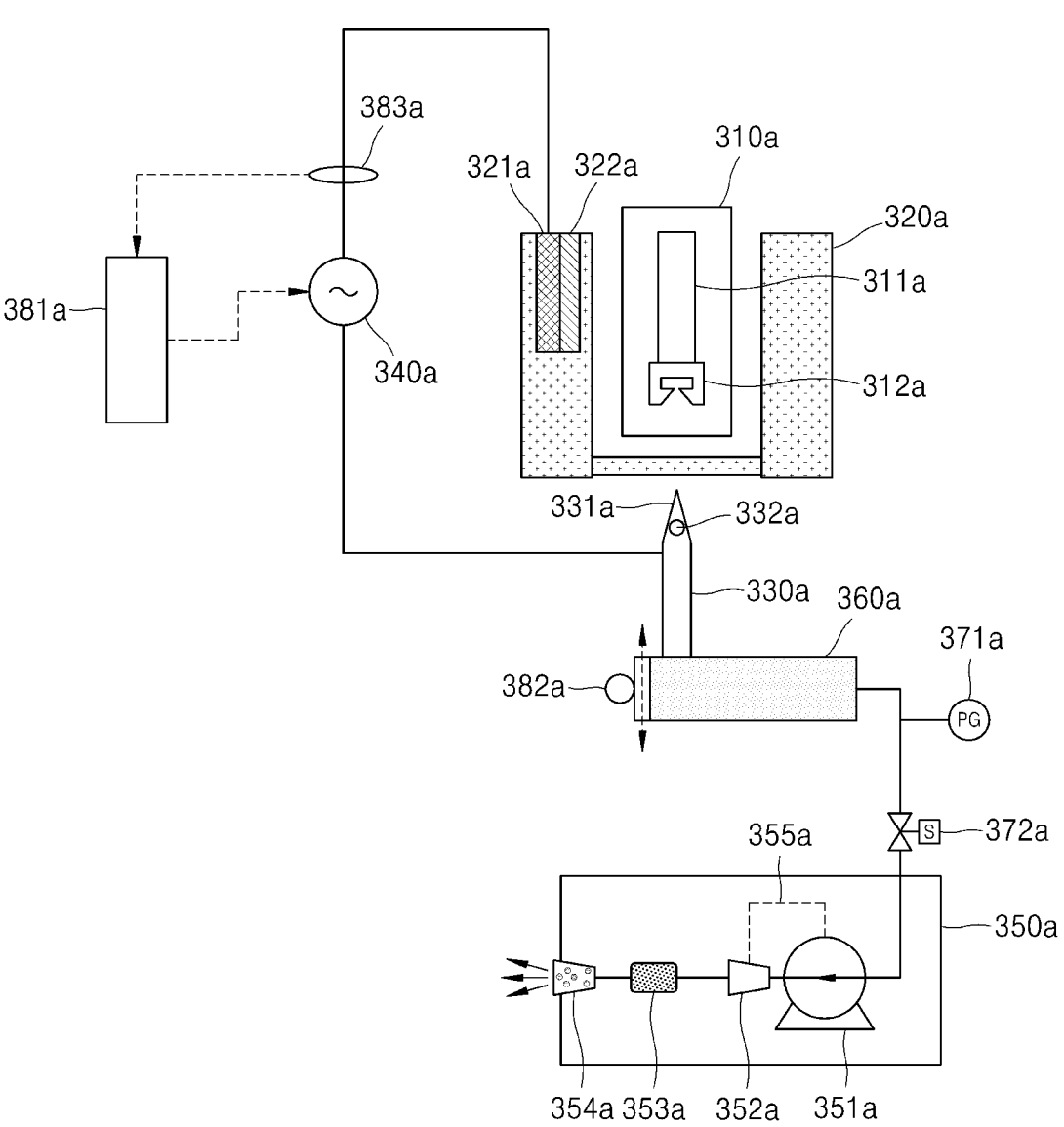

FIG. 15 is a configuration diagram schematically illustrating a plasma treatment apparatus according to the fourth embodiment of the present disclosure.

Figure 16:
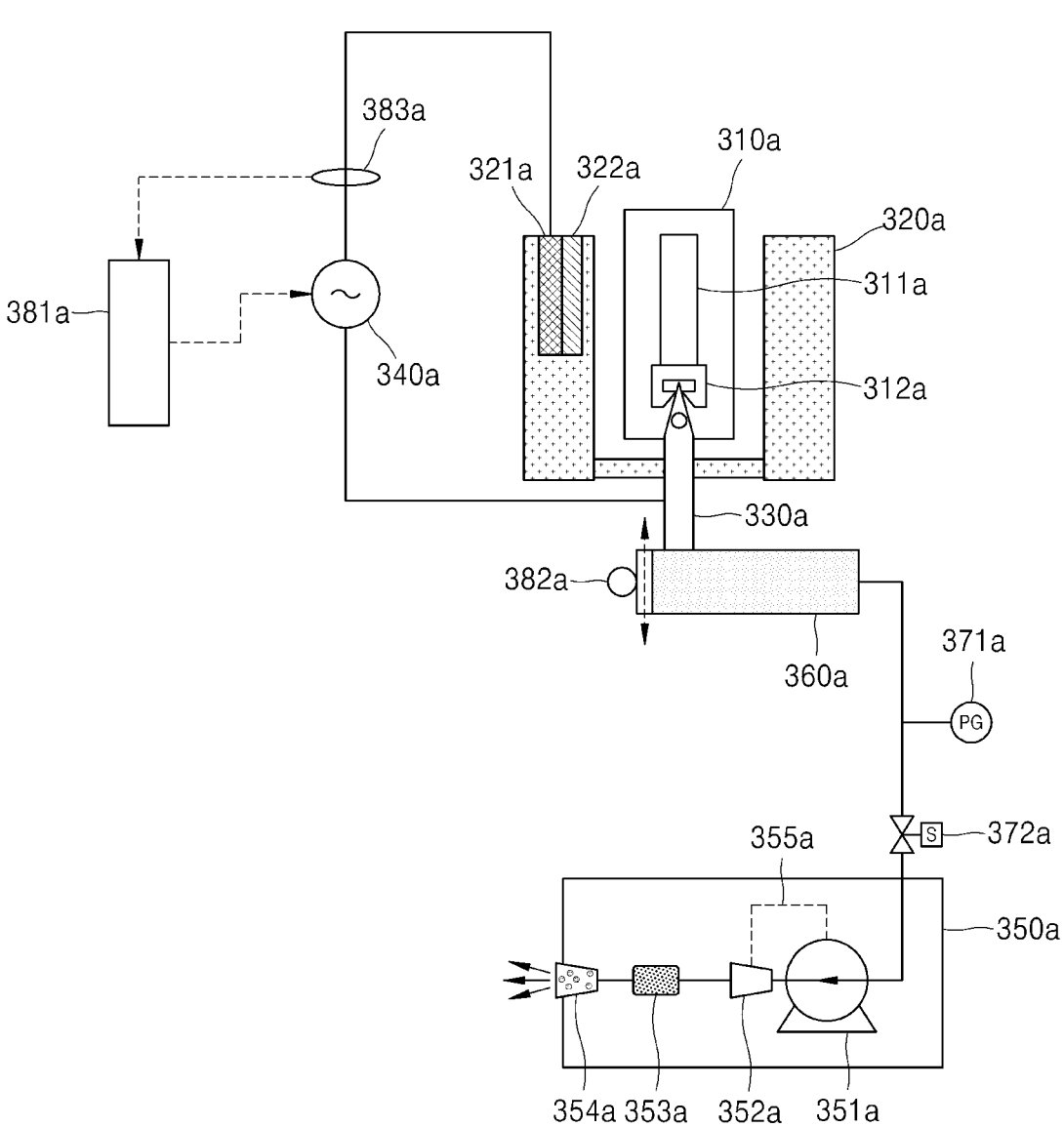

FIG. 16 is a configuration diagram schematically illustrating the plasma treatment apparatus when the contact unit is inserted into a container in FIG. 15.

Figure 17:
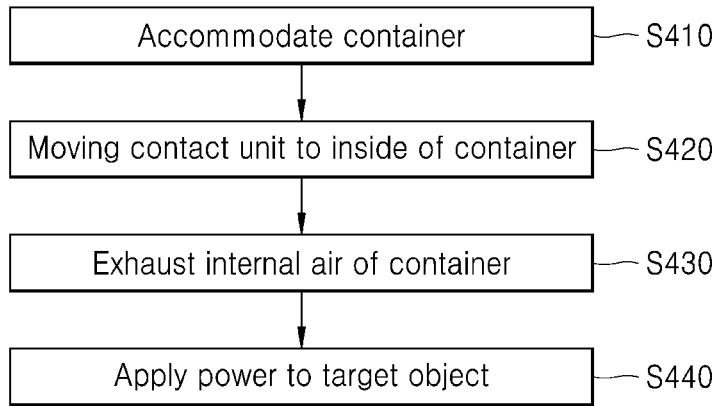

FIG. 17 is a flowchart illustrating a plasma treatment method according to the second embodiment of the present disclosure.

Figure 18:
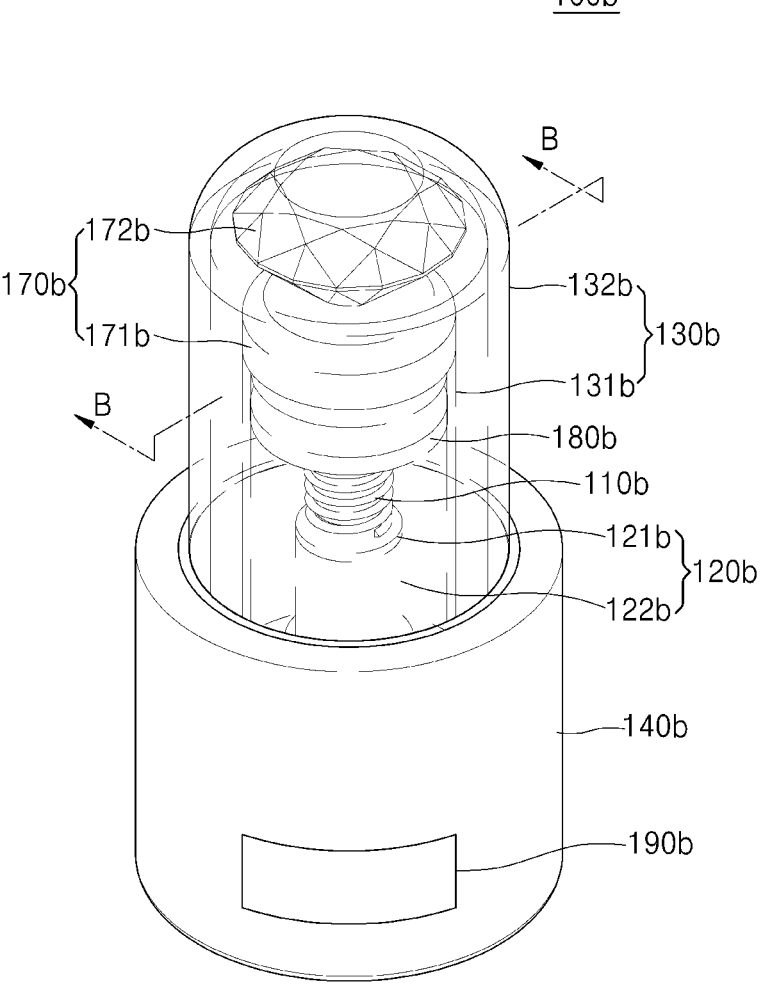

FIG. 18 is a perspective view of a plasma treatment container according to the second embodiment of the present disclosure.

Figure 19:
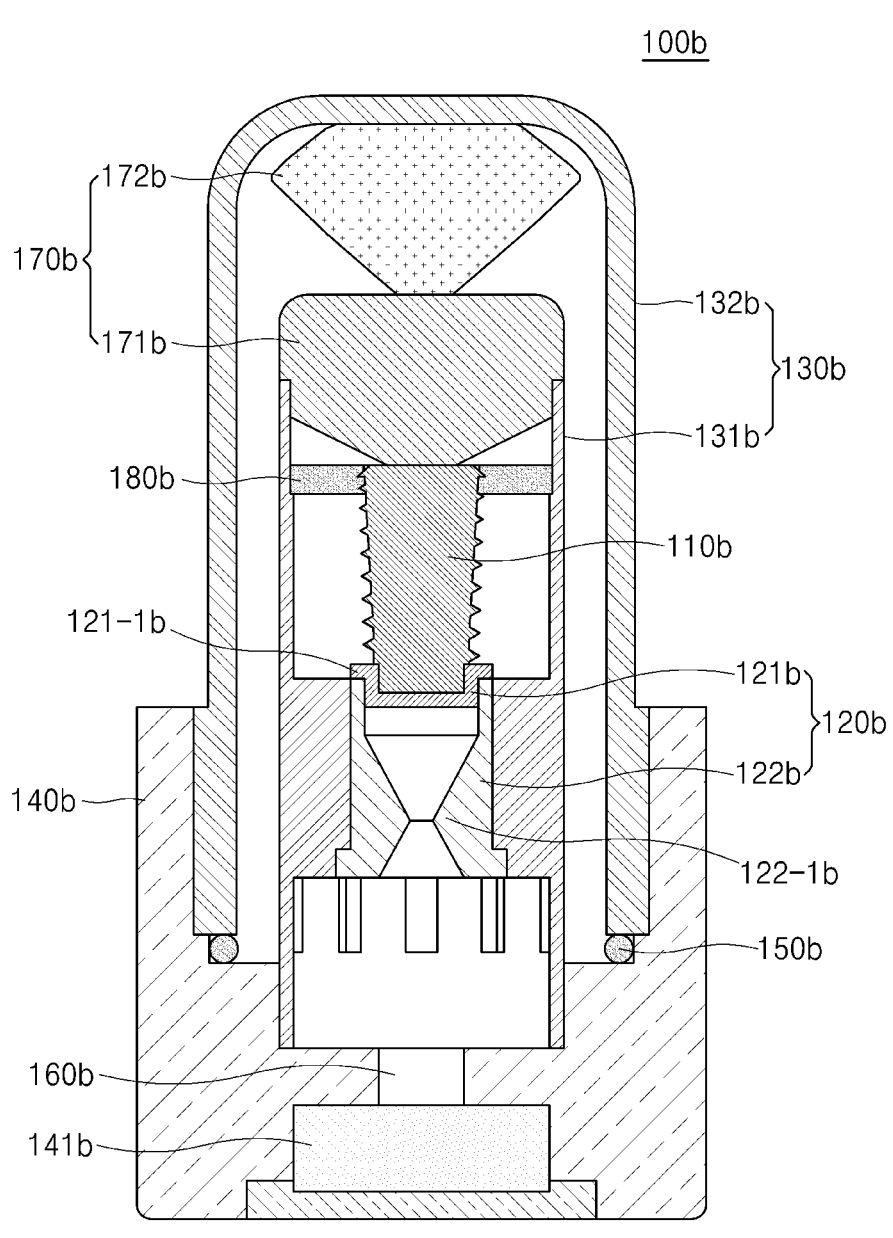

FIG. 19 is a cross-sectional view taken along line BB of FIG. 18.

Figure 20:
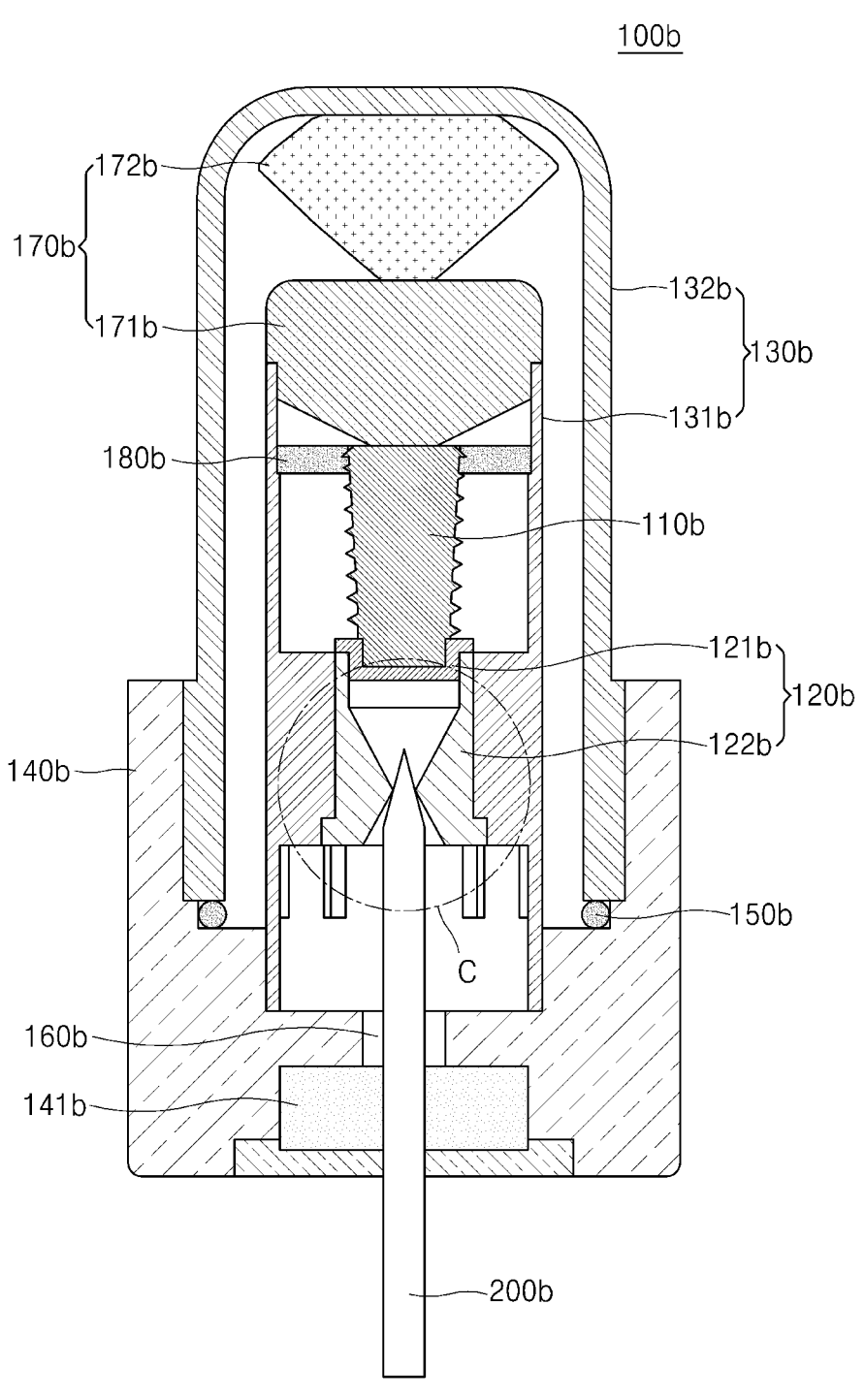

FIG. 20 is a diagram illustrating a state in which a contact unit is inserted into a plasma treatment container in FIG. 19.

Figure 21:
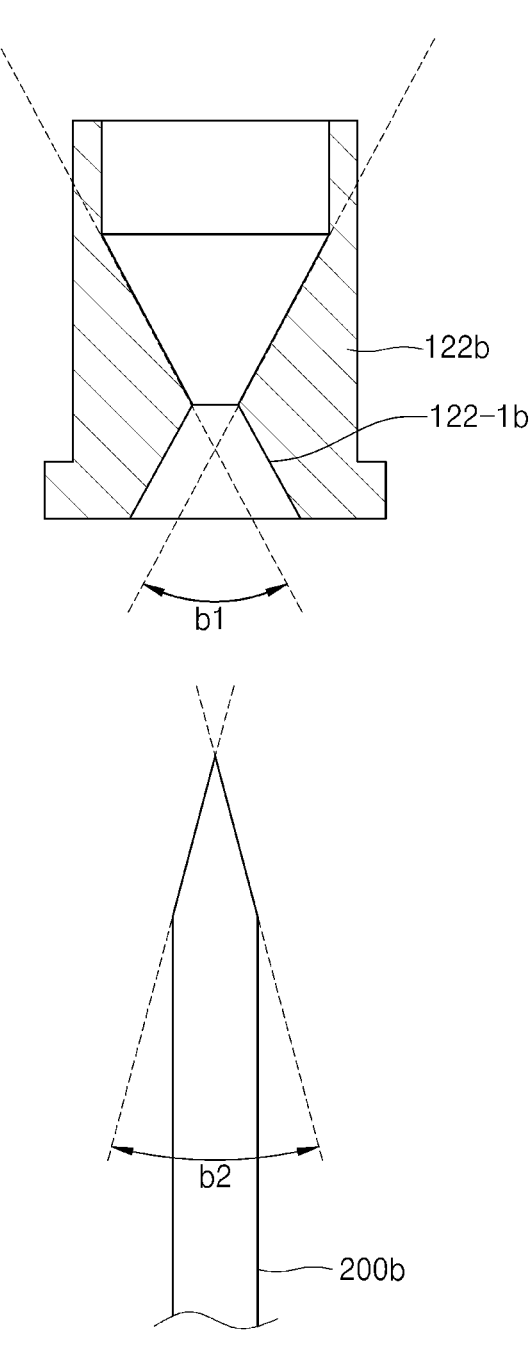

FIG. 21 is an enlarged view of region C of FIG. 20.

Figure 22:
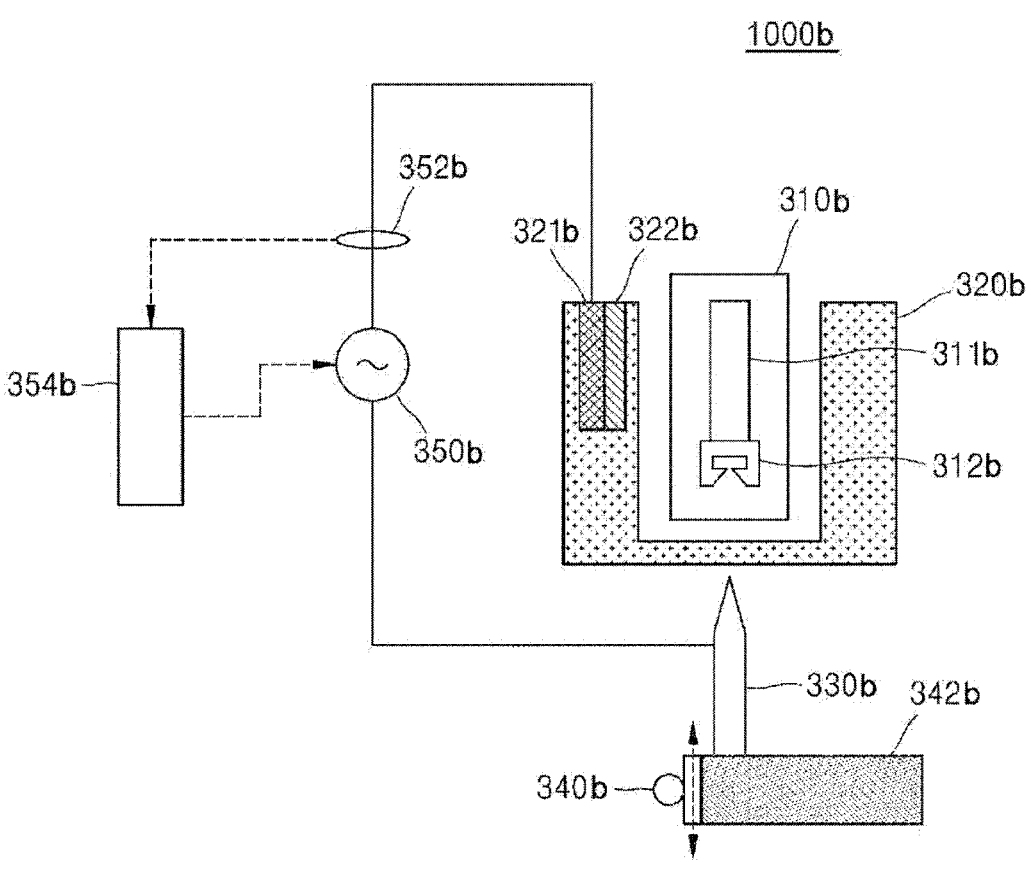

FIG. 22 is a schematic diagram of a plasma treatment apparatus according to the fifth embodiment of the present disclosure.

Figure 23:
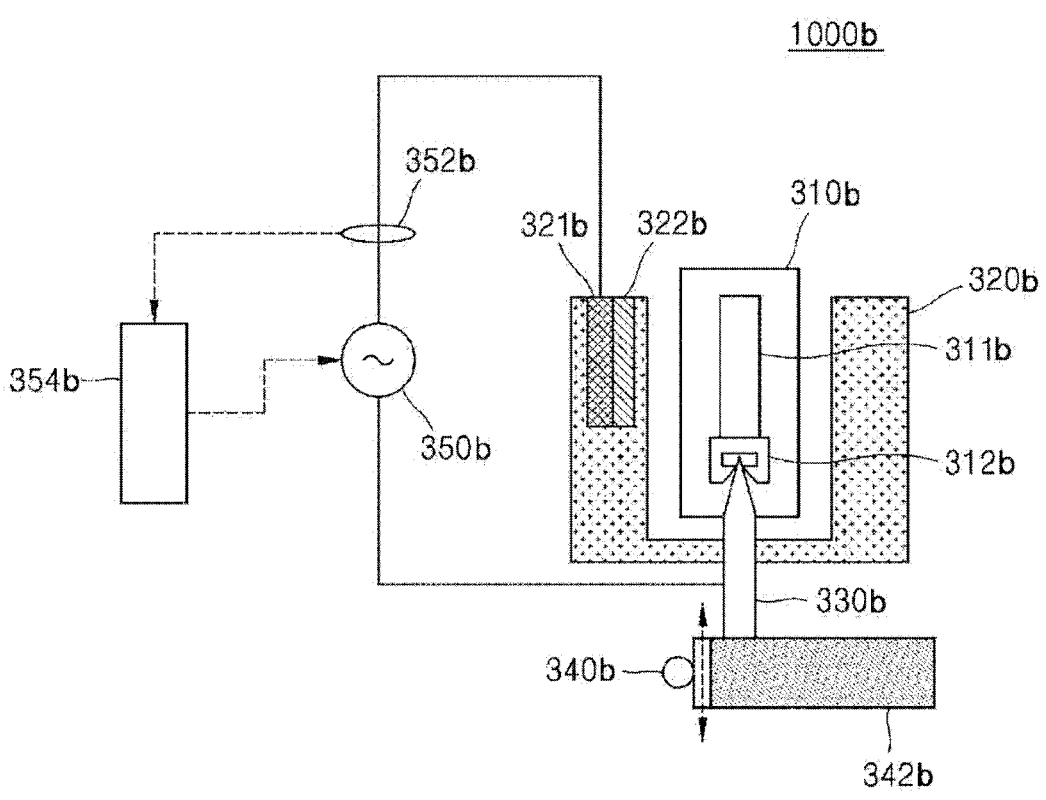

FIG. 23 is a diagram illustrating a state in which a contact unit is inserted into a plasma treatment container in the plasma treatment apparatus of FIG. 22.

Figure 24:
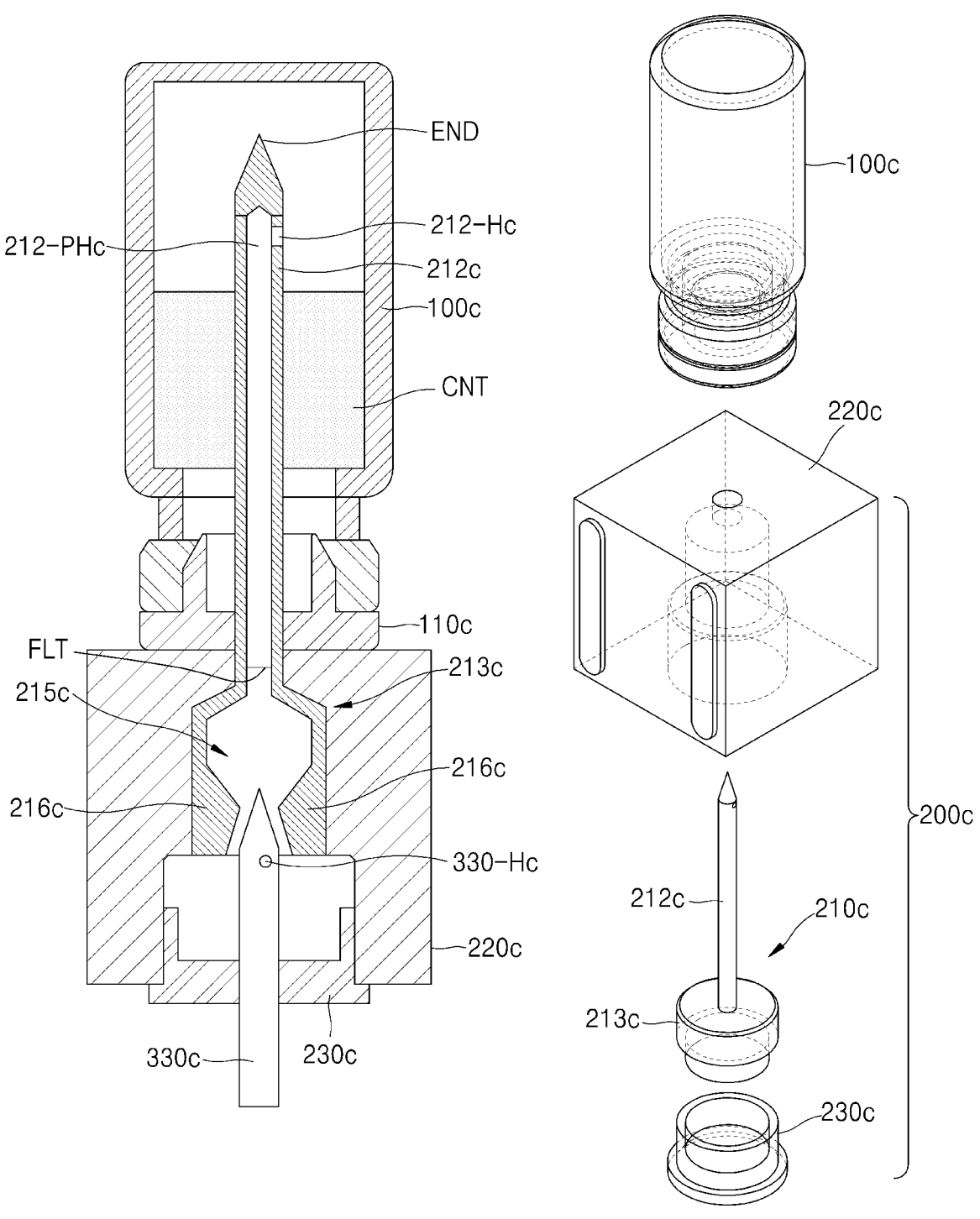

FIG. 24 is a cross-sectional view and an exploded view of a plasma treatment container according to the third embodiment of the present disclosure.

Figure 25:
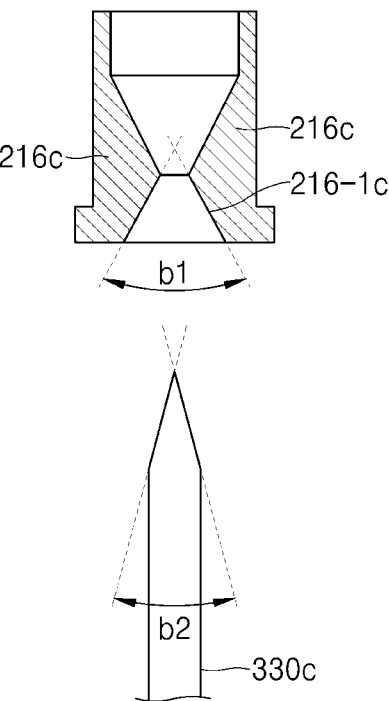

FIG. 25 is a diagram for describing a form in which an external ground electrode or power supply electrode is inserted into and brought into contact with the plasma treatment container of FIG. 24.

Figure 26:
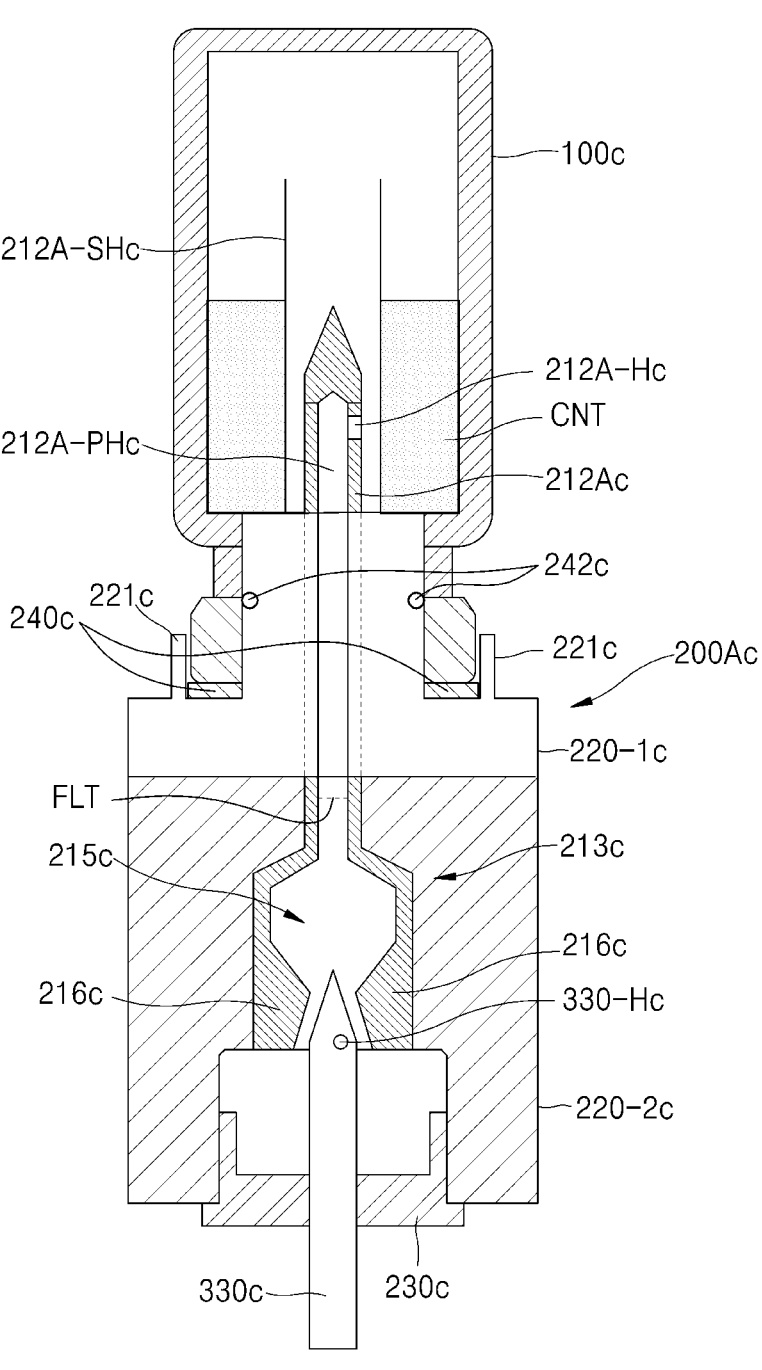

FIG. 26 is a cross-sectional view of a plasma treatment container according to the fourth embodiment of the present disclosure.

Figure 27:
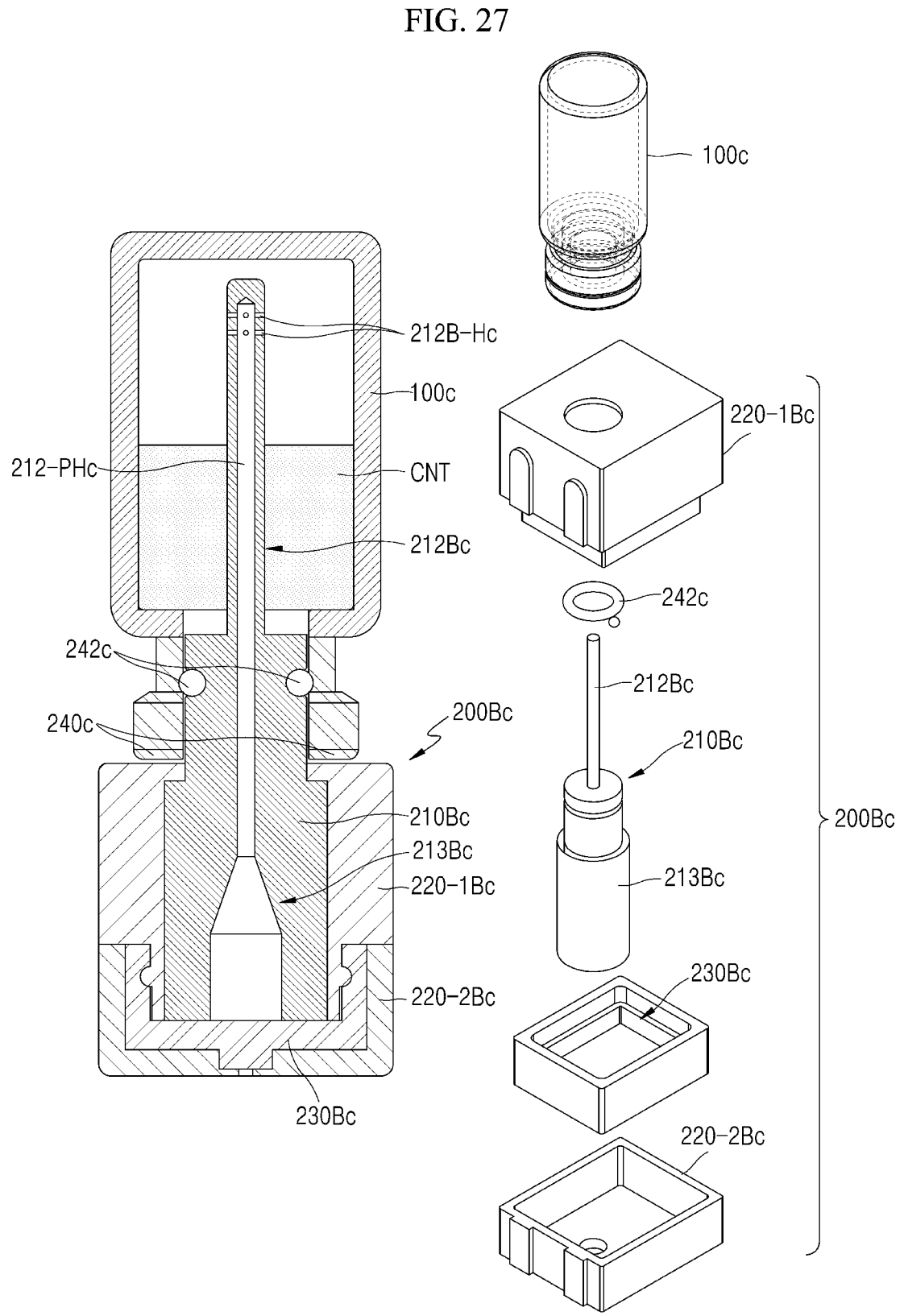

FIG. 27 is a cross-sectional view and an exploded view of a plasma treatment container according to the fifth embodiment of the present disclosure.

Figure 28:
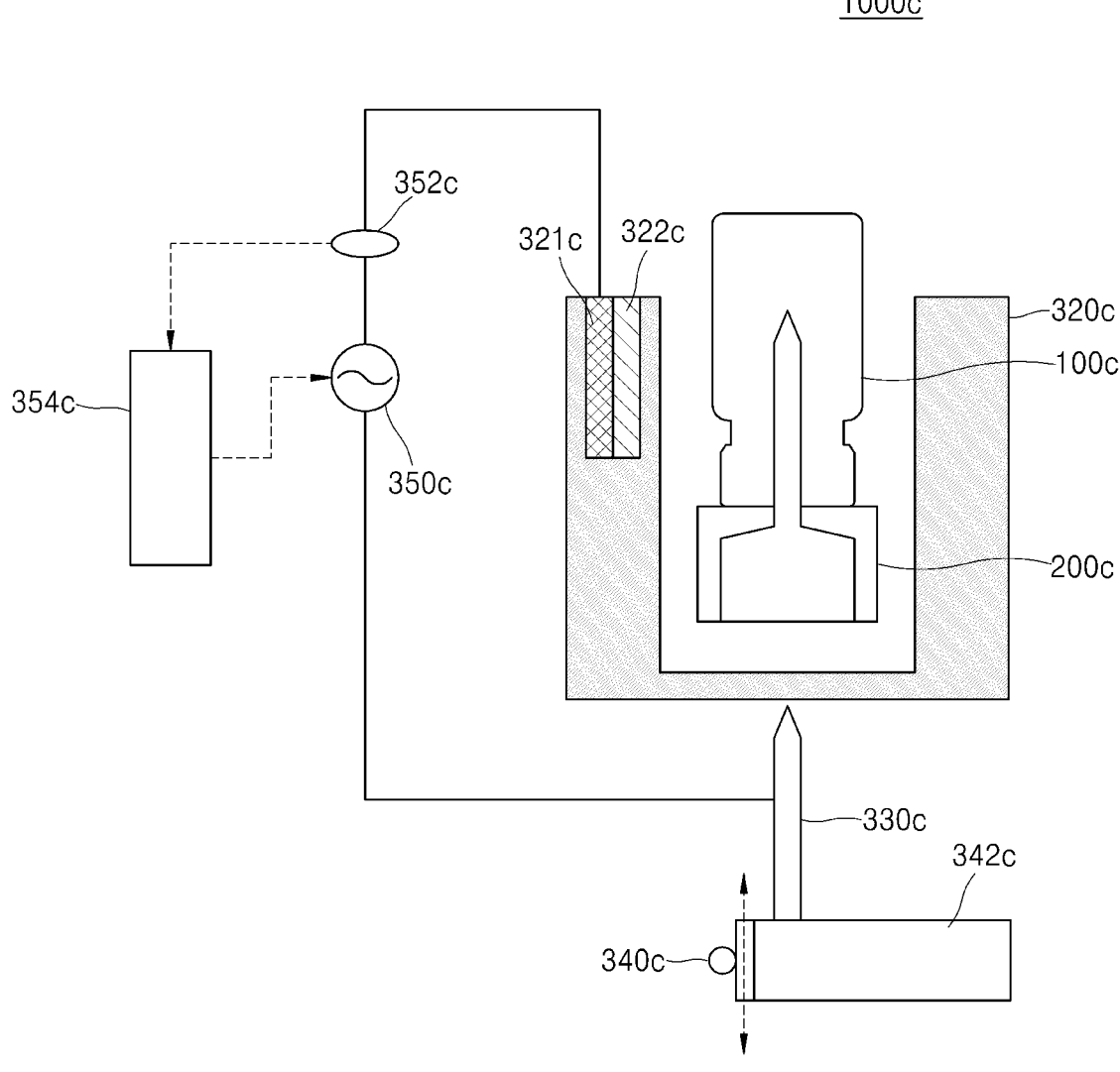
Figure 29:
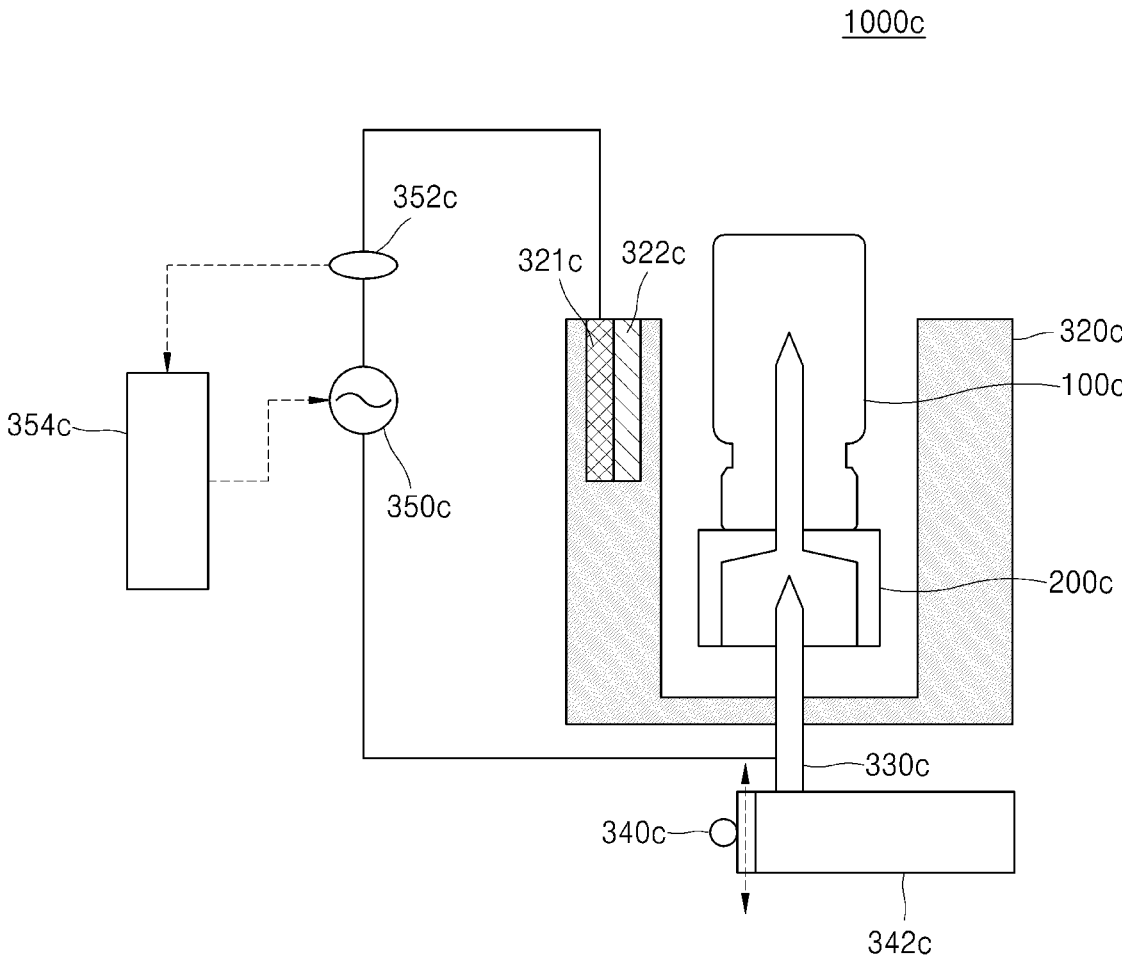

FIGS. 28 and 29 are diagrams for describing a process of performing surface treatment after an external electrode is inserted into a plasma treatment container of a plasma treatment apparatus according to the sixth embodiment.

Figure 30:
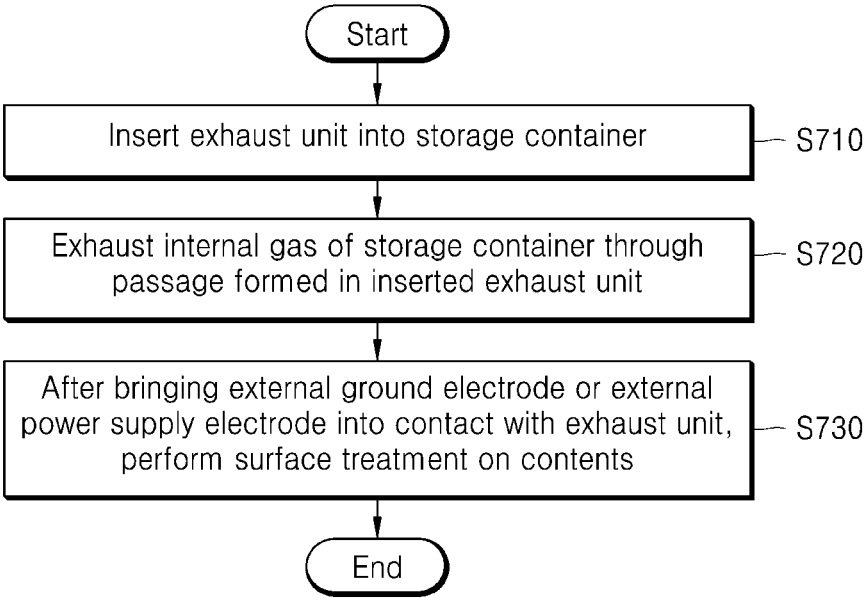

FIG. 30 is a flowchart of a plasma treatment method according to the third embodiment of the present disclosure.

FIG. 31 is a flowchart of a plasma treatment method according to the fourth embodiment of the present disclosure.

MODE FOR INVENTION

Exemplary embodiments according to the technical spirit of the present disclosure are provided to more completely explain the technical spirit of the present disclosure to those of skill in the art, and the following embodiments may be variously modified, and the scope of the technical spirit of the present is not limited to the following embodiments. Rather, these embodiments are provided such that the present disclosure will be thorough and complete, and will fully convey the scope of the present disclosure to those skill in the art.

It will be understood that, although terms, such as 'first' or 'second', may be used herein to describe various members, regions, layers, sections, and/or components, these members, regions, layers, sections, and/or components should not be limited by these terms. These terms do not denote any order, quantity, or importance, but rather are only used to distinguish one component, region, layer, and/or section from another component, region, layer, and/or section. Thus, a first member, component, region, layer, or section discussed below could be termed a second member, component, region, layer, or section without departing from the teachings of the technical spirit of the present disclosure. For example, as long as within the scope of the present disclosure, a first component may be referred to as a second component, and a second component may be referred to as a first component.

Unless otherwise defined, all terms including technical and scientific terms used herein have the same meaning as commonly understood by those of skill in the art to which the present disclosure. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

As used herein, the term 'and/or' includes any and all combinations of one or more of the associated listed items.

Hereinafter, embodiments of the present disclosure will be described in detail with reference to the accompanying drawings.

Hereinafter, embodiments according to the technical spirit of the present disclosure will be described in detail in turn.

Plasma Treatment Apparatus According to the First Embodiment of the Present Disclosure Hereinafter, a plasma treatment apparatus according to the first embodiment of the present disclosure will be described.

Figure 1:
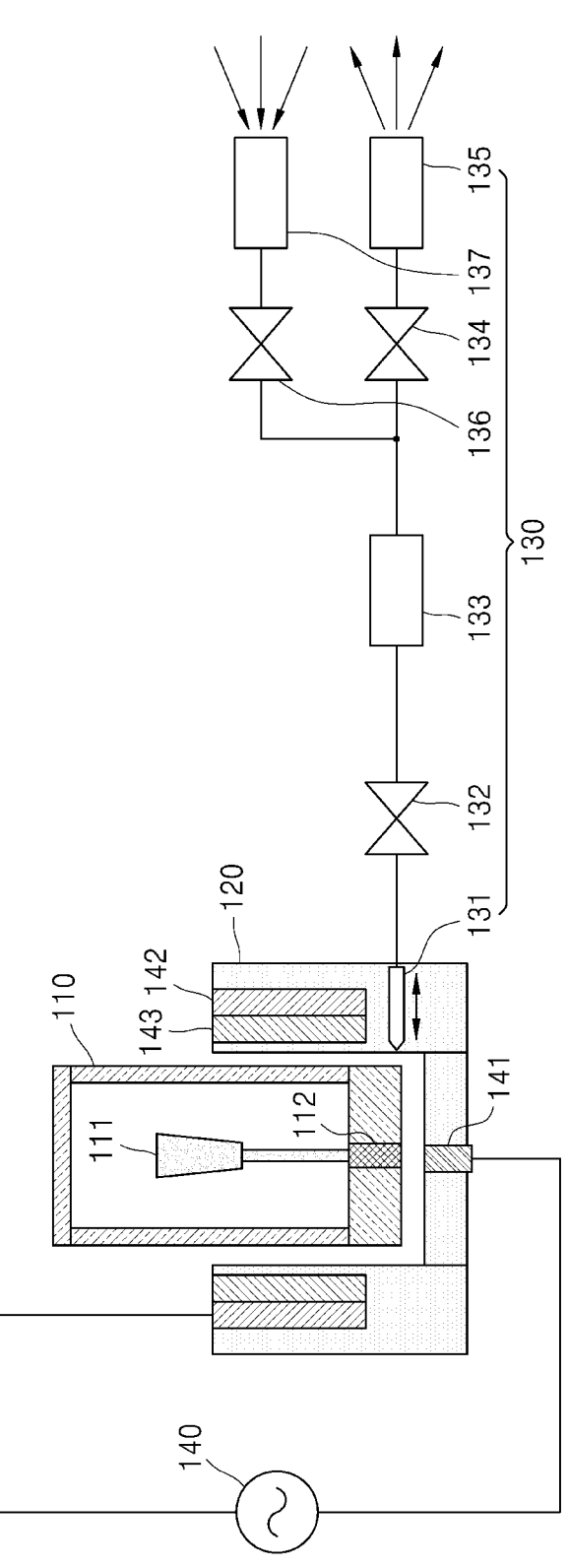
FIG. 1 is a configuration diagram schematically illustrating a plasma treatment apparatus according to the first embodiment of the present disclosure.

FIG. 1 is a configuration diagram schematically illustrating the plasma treatment apparatus according to the first embodiment of the present disclosure.

Referring to FIG. 1, the plasma treatment apparatus according to the first embodiment of the present disclosure includes an accommodation unit 120 for accommodating a container 110 in which a target object 111 is accommodated, an exhaust unit 130 connected to the accommodation unit 120 to exhaust internal air of the container 110, and treatment units 140, 141, 142, and 143 that apply electric power to the container 110 to generate plasma in the container 110 from which the internal air is exhausted by the exhaust unit 130.

Preferably, the container 110 is a container for accommodating an implant fixture.

Preferably, the container 110 is an ampoule.

Preferably, the target object 111 is an implant fixture.

Preferably, the accommodation unit 120 has a hole structure, and the lower end of the container 110 is fitted into the accommodation unit 120.

Preferably, the accommodation unit 120 is configured such that the container 110 is fastened to the apparatus in a forward, reverse, horizontal or vertical direction.

Preferably, the accommodation unit 120 includes a fastening unit for fixing the container 110 having been accommodated.

The container 110 may be provided with a quick response (QR) code, bar code, or near-field communication connection (radio-frequency identification (RFID), near-field communication (NFC)) on a surface that is brought into contact when the container 110 is accommodated.

The QR code, barcode, or near-field communication connection (RFID, NFC) may be a display unit provided on the outer surface of the container 110. In this case, the display unit contains information about a gas environment within the container 110, position information when the container 110 is accommodated, unique code information of the container 110, information about the target object accommodated in the container 110, etc.

When the container 110 is accommodated in the accommodation unit 120, the accommodation unit 120 may read the information contained in the display unit provided in the container 110 to determine at least one of whether the container 110 is accurately accommodated in a target position, whether the container 110 is a genuine product, the number of times the container 110 is used for plasma treatment, the type of the container 110, and the type of the target object accommodated in the container 110.

When the container 110 is accommodated in the accommodation unit 120, the accommodation unit 120 may determine, through the QR code, barcode, or near-field communication connection (RFID, NFC) provided in the container 110, whether the container 110 is accommodated, the type of the container 110, whether the container 110 is a genuine product, whether the container 110 is accommodated in the correct position, the type of the target object accommodated in the container 110, the number of times the container 110 is used for plasma treatment, etc.

The accommodation unit 120 may read information contained in the display unit provided in the container 110 to determine the internal environment of the container 110, and the power supply unit 140 may apply a voltage by varying a voltage condition according to the internal environment determined by the accommodation unit 120 and the display unit. Therefore, plasma treatment is performed by varying the voltage condition according to the internal environment of the container 110, and through this, more effective plasma treatment of the target object may be performed.

The exhaust unit 130 exhausts the internal air of the container 110.

Preferably, the exhaust unit 130 includes path generation units 131, 132, and 133 for generating a path communicating with the inside of the container 110.

Preferably, the exhaust unit 130 includes a pump 135 that exhausts the internal air of the container 110, and the pump 135 exhausts the internal air of the container 110 through the path generated by the path generation units 131, 132, and 133.

Preferably, the path generation units 131, 132, and 133 include the needle 131 that pierces one surface of the container 110 to generate a path.

Preferably, the path generation units 131, 132, and 133 include the driving unit 133 for moving the needle 131.

Preferably, the driving unit 133 operates to move the needle 131 toward the container 110 when the container 110 is mounted on the apparatus or in response to a request for plasma treatment, to generate a path on one surface of the container 110 through which air passes.

Preferably, the needle 131 has a sharp tip in which a through hole is formed such that the needle 131 partially penetrates one surface of the container 110 to exhaust the internal air of the container 110 through the through hole of the needle 131.

Preferably, the needle 131 partially penetrates one surface of the container 110 before plasma treatment is performed, to form a path through which air passes, maintains the penetration during the plasma treatment, and after the plasma treatment is completed, serves as an air injection passage for venting the inside of the container 110.

Preferably, the needle 131 is vented after the plasma treatment is completed, and then returns. Here, the container 110 is elastic to return to its original shape without the path generated by the penetration by the needle 131 when the needle 131 is separated therefrom.

Preferably, the path generation units 131, 132, and 133 include the exhaust valve 132 in the path communicating with the inside of the container 110.

Preferably, the exhaust valve 132 is open or closed in response to a control signal, to control exhausting or stopping of the internal air of the container 110.

Preferably, the exhaust valve 132 is controlled to be closed when an error occurs in a fastening state of the container 110 or in a plasma treatment operation, so as to prevent damage to the container 110 or the target object 111.

Preferably, the exhaust unit 130 includes a pump valve 134 adjacent to the pump 135.

Preferably, the pump valve 134 operates to be open when the internal air of the container 110 is exhausted, and to be closed when the inside of the container 110 is vented.

Preferably, the exhaust unit 130 includes a filter 137 in a path through which external air is introduced, and a filter valve 136 adjacent to the filter 137, to vent the inside of the container 110.

Preferably, the filter 137 filters out or purifies pollutants contained in the external air. According to an embodiment, the filter 137 is a high-efficiency particulate air (HEPA) filter.

Preferably, the filter valve 136 operates to be closed when the internal air of the container 110 is exhausted, and to be open when the inside of the container 110 is vented.

Preferably, the apparatus vents the inside of the container 110 and then exhausts the internal air again to create a vacuum in the container 110 on which the plasma treatment is completely performed.

The treatment units 140, 141, 142, and 143 apply electric power to the container 110 to generate plasma in the container 110 from which the internal air is exhausted by the exhaust unit 130.

Preferably, the treatment units 140, 141, 142, and 143 are components for plasma surface treatment of the target object 111 accommodated in the container 110.

Preferably, the treatment units 140, 141, 142, and 143 include the power supply unit 140 that applies a voltage to the target object 111 accommodated in the container 110.

Preferably, the power supply unit 140 is connected to the first electrode unit 141 in contact with an electrical connection unit 112 of the container 110 that is electrically connected to the target object 111, and then apply a voltage to the target object 111.

Preferably, the first electrode unit 141 is a power terminal, and when the container 110 is accommodated in the accommodation unit 120, the first electrode unit 141 is brought into contact with and thus electrically connected to the electrical connection unit 112 of the container 110.

Preferably, the first electrode unit 141 is in contact with one surface of the container 110 exposed such that electricity flows to the target object 111, and then applies a voltage to the target object 111.

Preferably, the electrical connection unit 112 is made of a metal material, which enables an electrical connection and is the same material as that of the target object 111, and may be an electrical terminal exposed to the outer surface of the container 110.

As such, the target object 111 functions as a high-voltage part in plasma generation through dielectric barrier discharge.

Preferably, the treatment units 140, 141, 142, and 143 include the grounded second electrode unit 142.

Preferably, the second electrode unit 142 is adjacent to the outer surface of the container 110 accommodated in the accommodation unit 120 and is grounded.

Preferably, the second electrode unit 142 is a ground electrode to which no voltage is applied, and maintains the ground (OV).

Preferably, the second electrode unit 142 is included in the accommodation unit 120, and is formed on a surface to which a part of the outer surface of the container 110 is adjacent when the container 110 is accommodated in the accommodation unit 120.

Preferably, the second electrode unit 142 is a ground electrode corresponding to the target object 111 accommodated in the container 110, which is applied with the voltage and thus is functioning as the high-voltage part when the container 110 is accommodated in the accommodation unit 120, and the second electrode unit 142 interacts with the target object 111 to form an electromagnetic field.

Preferably, the second electrode unit 142 may be the path generation units 131, 132, and 133 that generate a path communicating with the inside of the container 110, and in particular, may be the needle 131 that pierces one surface of the container 110 to generate the path.

Preferably, the treatment units 140, 141, 142, and 143 include the dielectric unit 143.

Preferably, the dielectric unit 143 is in contact with the second electrode unit 142 and is closer to the container 110 than is the second electrode unit 142.

Preferably, the dielectric unit 143 is included in the accommodation unit 120, and is formed on a surface to which a part of the outer surface of the container 110 is adjacent when the container 110 is accommodated in the accommodation unit 120.

Preferably, the dielectric unit 143 is formed in the container 110 and may be an inner or outer cylinder of the container 110.

Preferably, the dielectric unit 143 may be an internal space of the container 110.

Plasma Treatment Apparatus According to the
Second Embodiment of the Present Disclosure Hereinafter, a plasma treatment apparatus according to the second embodiment of the present disclosure will be described.

Figure 2:
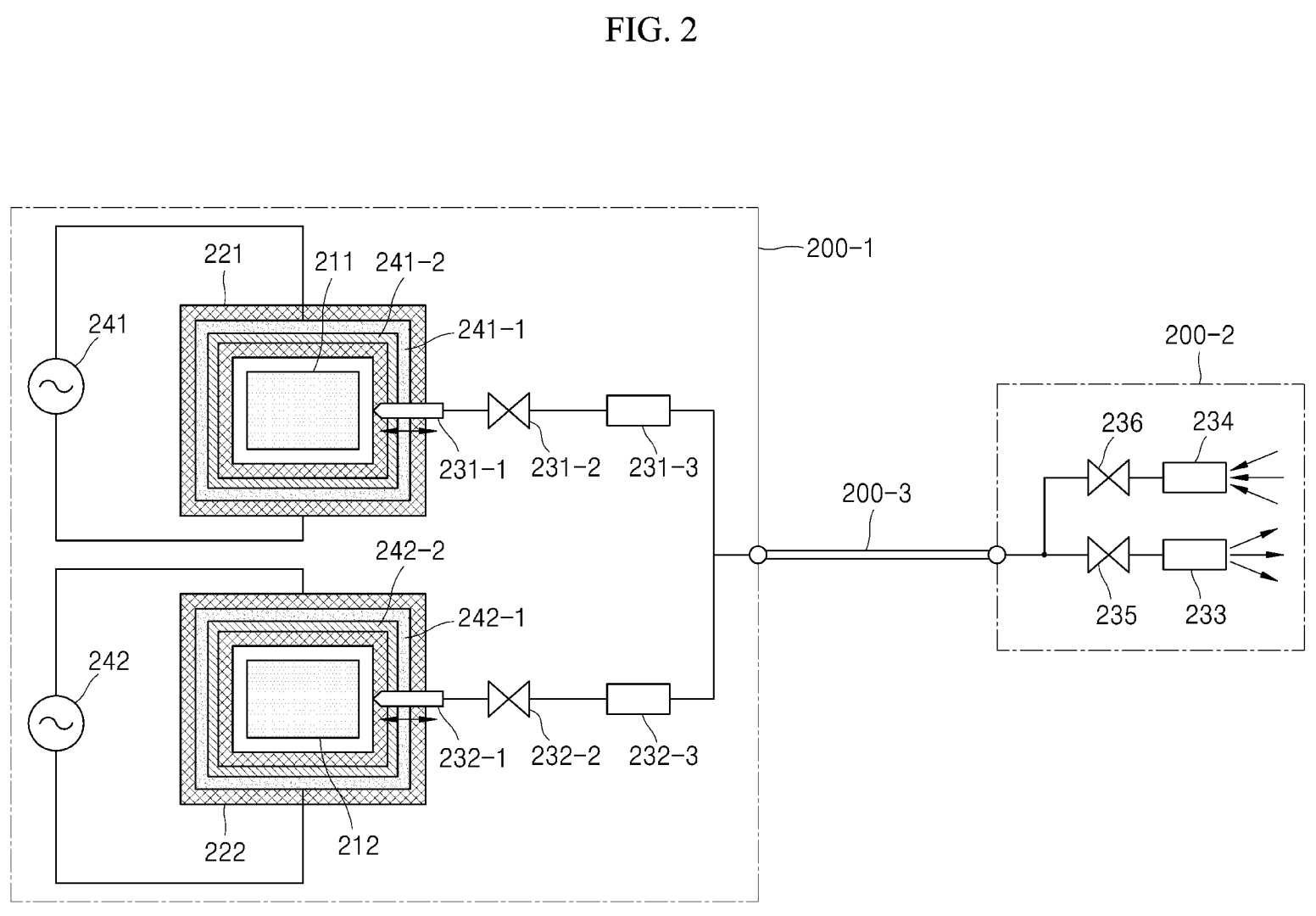

FIG. 2 is a configuration diagram schematically illustrating the plasma treatment apparatus according to the second embodiment of the present disclosure.

FIG. 1 is a schematic configuration diagram of a vertical cross-section of the plasma treatment apparatus according to the first embodiment of the present disclosure, and FIG. 2 is a schematic configuration diagram of a horizontal cross-section of the plasma treatment apparatus according to the second embodiment of the present disclosure.

Referring to FIG. 2, the plasma treatment apparatus according to the second embodiment of the present disclosure includes a plurality of accommodation units 221 and 222 for accommodating a plurality of containers 211 and 212 in which a plurality of target objects are accommodated, respectively, an independent exhaust unit 200-2 connected to each of the plurality of accommodation units 221 and 222 to exhaust internal air of the plurality of containers 211 and 212, and treatment units 241, 241-1, 241-2, 242, 242-1, 242-2 for applying, to each of the plurality of containers 211 and 212 from which the internal air is exhausted by the independent exhaust unit 200-2, electric power for generating plasma in the plurality of containers 211 and 212.

Preferably, the plasma treatment apparatus may simultaneously or individually process the plurality of target objects.

Preferably, the first container 211 in which the first target object is accommodated is accommodated in the first accommodation unit 221, the second container 212 in which the second target object is accommodated is accommodated in the second accommodation unit 222.

Preferably, the first accommodation unit 221 or the second accommodation unit 222 includes a sensor that detects whether a container is accommodated therein.

Preferably, the first accommodation unit 221 or the second accommodation unit 222 determines whether a container is accommodated, the type of the container, whether the container is a genuine product, whether the container is correctly accommodated, the type of a target object in the container, through a QR code, bar code, or near-field communication connection (RFID, NFC) on a surface that is brought into contact when the container is accommodated.

Preferably, the first path generation units 231-1, 231-2, and 231-3 generate a path for exhausting internal air of the first container 211 accommodated in the first accommodation unit 221, and, the second path generation units 232-1, 232-2, and 232-3 generate a path for exhausting internal air of second container 212 accommodated in the second accommodation unit 222.

Preferably, the first path generation units 231-1, 231-2, and 231-3 include the first needle 231-1 that pierces one surface of the first container 211 to generate a first path, the first driving unit 231-3 for moving the first needle 231-1, and the first exhaust valve 231-2 in the first path.

Preferably, the second path generation units 232-1, 232-2, and 232-3 include the second needle 232-1 that pierces one surface of the second container 212 to generate a second path, the second driving unit 232-3 for moving the second needle 232-1, and the second exhaust valve 232-2 in the second path.

Preferably, the first path generation units include the first needle 231-1 that pierces one surface of the first container 211 to generate the first path, and the first exhaust valve 231-2 in the first path, and the second path generation units include the second needle 232-1 that pierces one surface of the second container 212 to generate the second path, and the second exhaust valve 232-2 in the second path. Here, the driving units are formed as single units to drives a simultaneous operation or separate operations of the first needle 231-1 and the second needle 232-1.

Preferably, a control unit (not shown) obtains information about whether a container is accommodated, through the sensor included in the first accommodation unit 221 or the second accommodation unit 22 to detect whether a container is accommodated, and operates the first exhaust valve 231-2, the second exhaust valve 232-2, the first driving unit 231-3, and the second driving unit 232-3.

Preferably, when the first container 221 and the second container 222 are accommodated at the same time or when exhaust operations for the first container 221 and the second container 222 are required at the same time, the control unit opens the first exhaust valve 231-2 and the second exhaust valve 232-2 and drives the first driving unit 231-3 and the second driving unit 232-3 to move the first needle 231-1 and the second needle 232-2.

Preferably, when only the first container 221 is accommodated or when only an exhaust operation for the first container 221 is required, the control unit opens the first exhaust valve 231-2, closes the second exhaust valve 232-2, and drives only the first driving unit 231-3 to move only the first needle 231-1.

Preferably, the first treatment units 241, 241-1, and 241-2 apply power to the first container 211 for plasma surface treatment of the target object accommodated in the first container 211.

Preferably, the first treatment units 241, 241-1, and 241-2 include the first power supply unit 241 that applies a voltage to the target object accommodated in the first container 211, the first ground electrode unit 241-2, which is adjacent to the outer surface of the first container 211 accommodated in the first accommodation unit 221 and grounded, and the first dielectric unit 241-1, which is in contact with the first ground electrode unit 241-2 and is closer to the first container 211 than is the first ground electrode unit 241-2.

Preferably, the second treatment units 242, 242-1, and 242-2 include the second power supply unit 242 that applies a voltage to the target object accommodated in the second container 212, the second ground electrode unit 242-2, which is adjacent to the outer surface of the second container 212 accommodated in the second accommodation unit 222 and grounded, and the second dielectric unit 242-1, which is in contact with the second ground electrode unit 242-2 and is closer to the second container 212 than is the second ground electrode unit 242-2.

Preferably, the first power supply unit 241 and the first power supply unit 242 are configured as single units, and a power line for applying power to each container is provided with a switch to enable an simultaneous operation or separate operations.

Preferably, the plasma treatment apparatus according to the second embodiment of the present disclosure includes a housing 200-1 for configuring an independent plasma treatment module, the independent exhaust unit 200-2, and a connection unit 200-3 connecting the housing 200-1 and the exhaust unit 200-2 to each other.

Preferably, the housing 200-1 surrounds a plurality of accommodation units 211 and 212, a plurality of path generation units, and a plurality of treatment units, and packs them to be independent of the exhaust unit including the pump.

Preferably, the connection unit 200-3 connects the housing 200-1 and the exhaust unit 200-2 to each other such that the independent plasma treatment module and the independent exhaust unit are arranged independently of each other and may be changed.

Preferably, the connection unit 200-3 is elastic or flexible, or enables a coupling connection between a plurality of connection units, and thus is rotatable such that, although the point and length of connection between the housing 200-1 and the exhaust unit 200-2 are fixed, the arrangement may be changed.

Preferably, the independent exhaust unit 200-2 has an exterior independent of the independent plasma treatment module, and includes an exhaust pump 233, a pump valve 235, a filter 234, and a filter valve 236.

Plasma Treatment Apparatus According to the Third Embodiment of the Present Disclosure Hereinafter, a plasma treatment apparatus according to the third embodiment of the present disclosure will be described.

Figure 4:
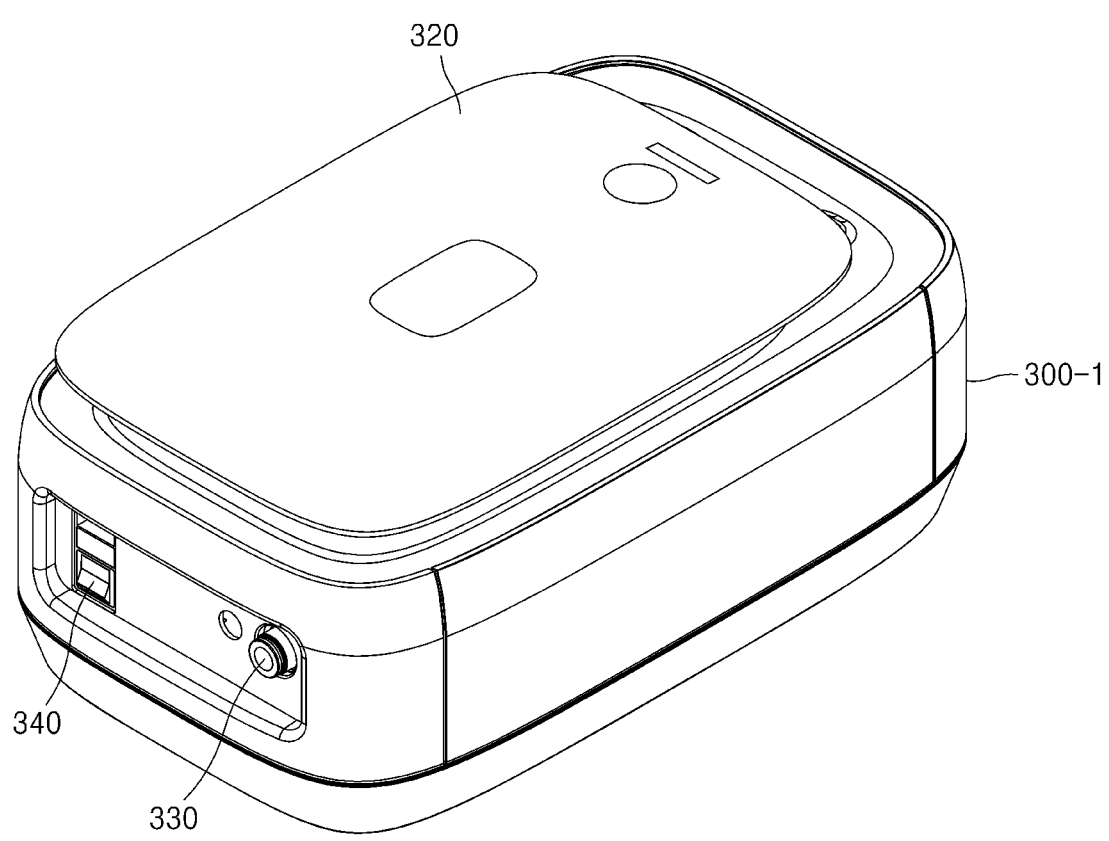
FIG. 4 is a perspective view of the rear of the plasma treatment apparatus of FIG. 3.

FIG. 3 is a perspective view of the front of the plasma treatment apparatus according to the third embodiment of the present disclosure, and FIG. 4 is a perspective view of the rear of the plasma treatment apparatus of FIG. 3.

Referring to FIGS. 3 and 4, the plasma treatment apparatus according to the third embodiment of the present disclosure includes a first accommodation unit 311 for accommodating a first container, a second accommodation unit 312 for accommodating a second container, and the opening/closing unit 320 for opening and closing the first accommodation unit 311 and the second accommodation unit 312.

Preferably, the opening/closing unit 320 may perform a closing operation to prevent external exposure of the first accommodation unit 311 and the second accommodation unit 312 when the apparatus is not operating, an opening operation to accommodate a container in the first accommodation unit 311 or the second accommodation unit 312, and a fixing operation to prevent separation of the container accommodated in the first accommodation unit 311 or the second accommodation unit 312 during a plasma treatment operation is performed by the apparatus.

Preferably, the opening/closing unit 320 includes a display unit 321 on the outer surface thereof for displaying an operating state of the apparatus.

Preferably, a housing 300-1 may include a pump or may be connected to an independent pump.

Preferably, the housing 300-1 includes a connector 330 connected to the independent pump, and includes a power supply unit 340 of the apparatus.

(a) of FIG. 5 is a perspective view of the closed plasma treatment apparatus of FIG. 3, and (b) of FIG. 5 is a side view thereof.

Referring to (a) and (b) of FIG. 5, the opening/closing unit 320 slides in a horizontal direction to cover the first accommodation unit 311 and the second accommodation unit 312.

(a) of FIG. 6 is a perspective view of the open plasma treatment apparatus of FIG. 3, and (b) of FIG. 6 is a side view thereof.

Referring to (a) and (b) of FIG. 6, the opening/closing unit 320 slides in the horizontal direction to be open such that a first container 410 and a second container 420 are accommodated in the first accommodation unit 311 and the second accommodation unit 312, respectively.

(a) of FIG. 7 is a perspective view of the plasma treatment apparatus of FIG. 3 that is operating, and (b) of FIG. 7 is a side view thereof.

Referring to (a) and (b) of FIG. 7, the opening/closing unit 320 slides in the horizontal direction but moves less than when performing the closing operation to prevent separation of the first container 410 and the second container 420 accommodated in the first and second accommodation units 311 and 312, respectively.

Preferably, the opening/closing unit 320 has a step to be in contact with upper portions of the first container 410 and the second container 420 to prevent separation thereof.

Preferably, the opening/closing unit 320 has a fastening unit on a surface that is in contact with the first container 410 and the second container 420.

Preferably, a sensor (not shown) checks the degree of sliding of the opening/closing unit 320 to determine whether the opening/closing unit 320 is open, closed, or fixed during operation.

Preferably, when it is confirmed, through the sensor, that the opening/closing unit 320 slides and moves to change to an open state during operation of the apparatus, the control unit (not shown) controls to stop the application of power or stop an exhaust operation.

FIG. 8 is a configuration diagram schematically illustrating a container to be accommodated in the plasma treatment apparatus according to the third embodiment of the present disclosure.

Referring to FIG. 8, a container 400 has a plurality of holes 410 and 420.

Preferably, the container 400 has the plurality of holes 410 and 420 through which a lower block in contact with a target object accommodated in the container 400 is exposed to the outside of the container.

Preferably, in at least one 410 of the plurality of holes 410 and 420, a path communicating between the inside of the container 400 and a treatment apparatus is generated by a path generation unit of the plasma treatment apparatus according to the third embodiment of the present disclosure.

Preferably, at least one 410 of the plurality of holes 410 and 420 exposes a lower block that is made of elastic silicone to allow the path generation unit of the plasma treatment apparatus according to the third embodiment of the present disclosure to generate a communication path, and when plasma surface treatment is completed and the path generation unit is separated therefrom, returns its original shape to close the path.

Preferably, at least one 420 of the plurality of holes 410 and 420 is a fastening unit for fixing contact between an electrode for supplying power to the apparatus, and one surface of the exposed container 400 such that electricity flows to the accommodated target object, while electric power is applied to the target object.

Preferably, at least one 420 of the plurality of holes 410 and 420 is fastened as an elastic protrusion provided in the accommodation unit of the plasma treatment apparatus according to the third embodiment of the present disclosure is inserted into the hole 420.

FIGS. 9A to 9D show experimental results obtained by measuring carbon content when the surface of a target object is treated by using the plasma treatment apparatus according to the third embodiment of the present disclosure.

Referring to FIGS. 9A to 9D, FIG. 9A shows a result of measuring a carbon peak by using X-ray photoelectron spectroscopy (XPS) with respect to hydrocarbon (CHx) content of a fixture that is not surface-treated.

Figure 9A:
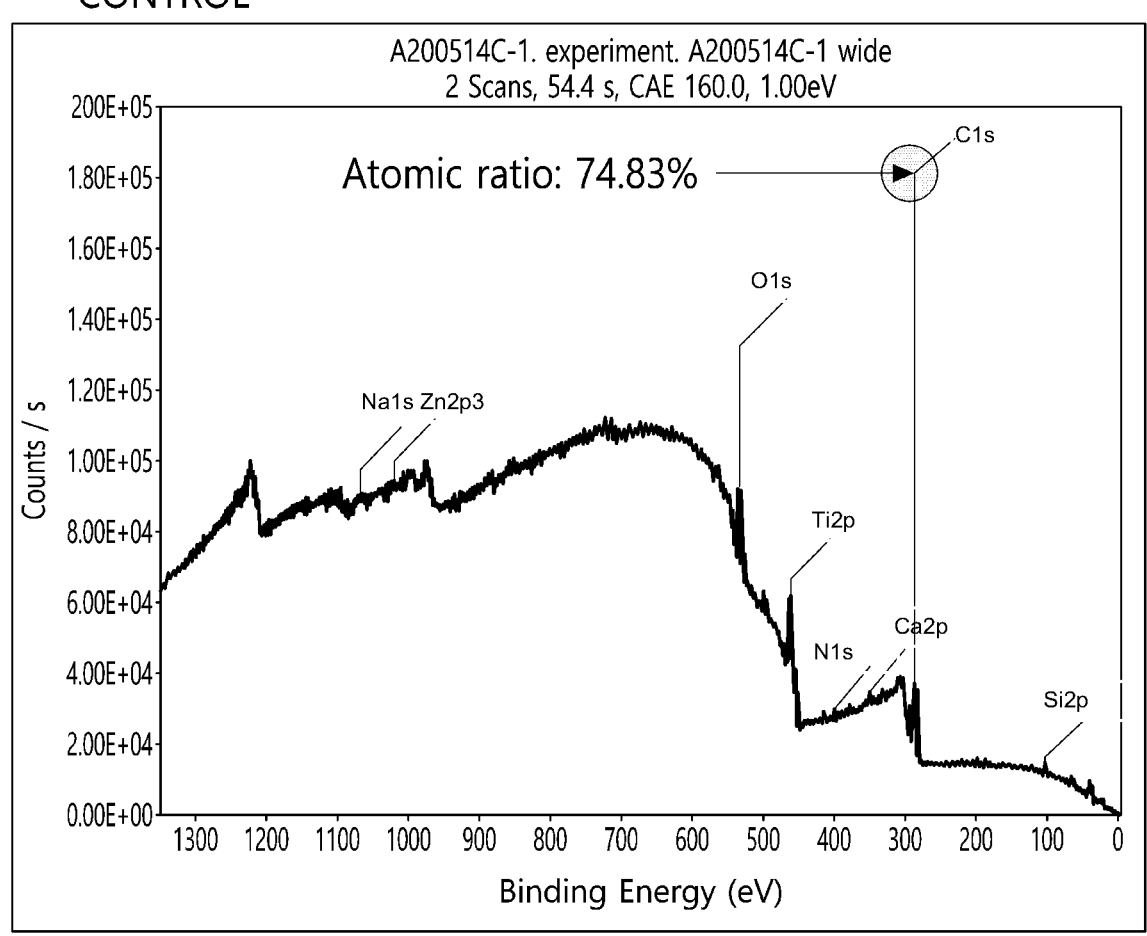
Figure 9B:
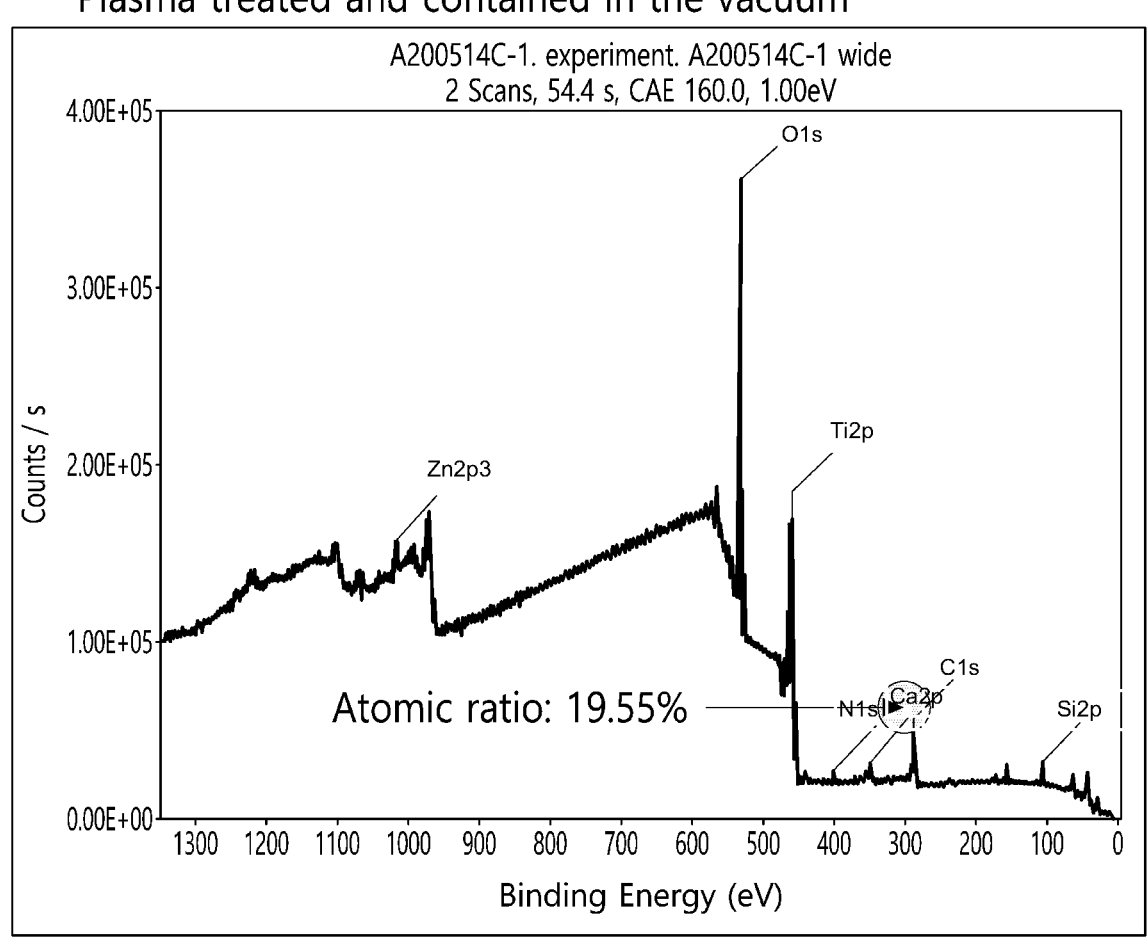

FIG. 9B shows a result of measuring a carbon peak by using XPS with respect to hydrocarbon content of a fixture that is surface-treated by the plasma treatment apparatus according to the third embodiment of the present disclosure.

Comparing FIGS. 9A and 9B with each other, the plasma treatment apparatus according to the third embodiment of the present disclosure may significantly reduce the carbon peak to 19.55%, compared to 74.83% of the untreated target object.

Figure 9C:
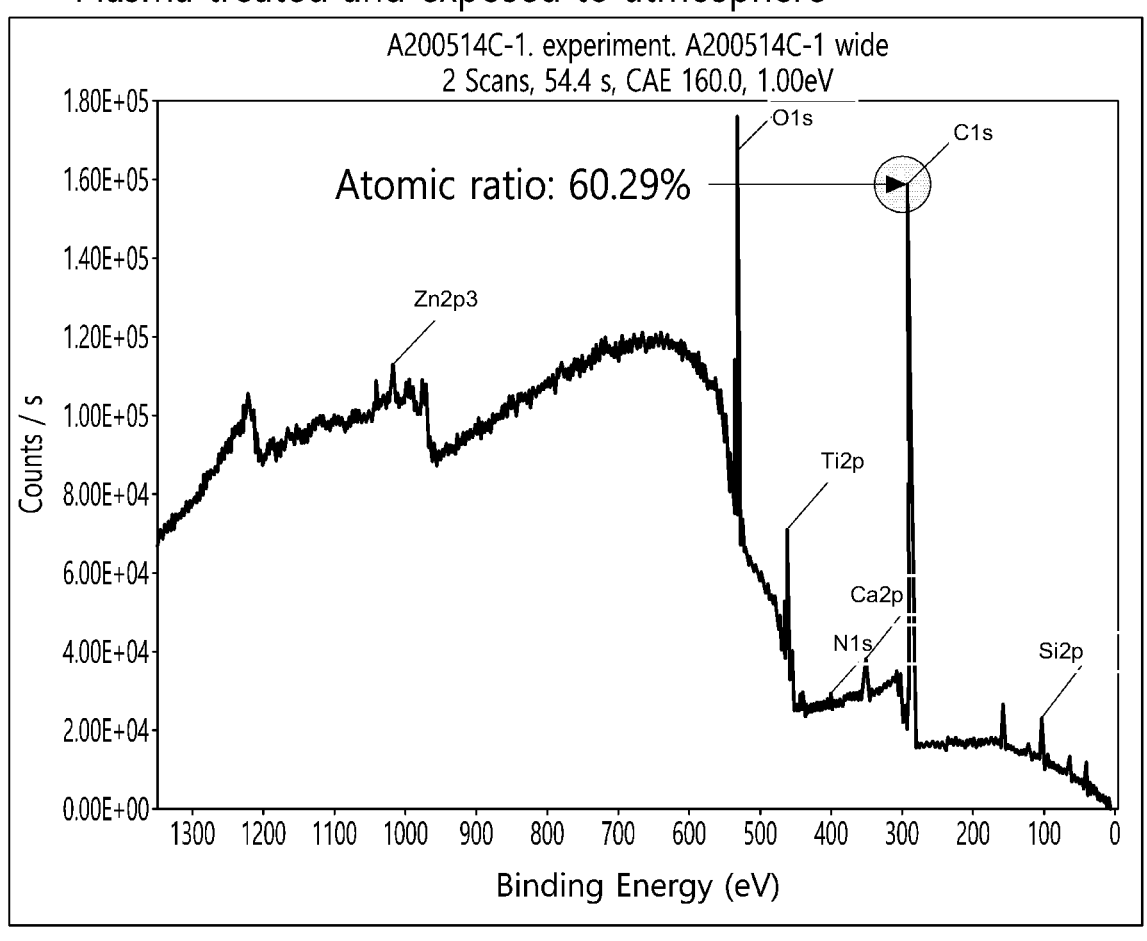

FIG. 9C shows a result of measuring a carbon peak by using XPS with respect to hydrocarbon content after exposing the surface of a fixture that is treated with the plasma treatment apparatus according to the third embodiment of the present disclosure, to the atmosphere for a certain time period (one day).

It may be seen, from FIG. 9C, that it is difficult to maintain the performance secured through plasma surface treatment, when exposed to the atmosphere even for a relatively short time period.

Figure 9D:
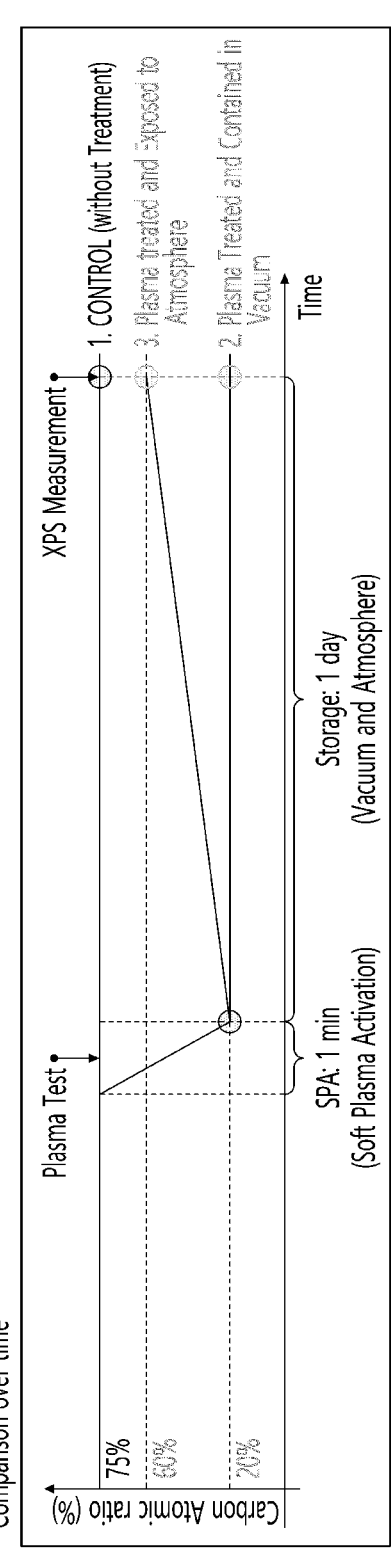

FIG. 9D shows changes over time in carbon content of the untreated sample in FIG. 9A, the sample that is plasma-surface-treated and then exposed to the atmosphere in FIG. 9B, and the sample that is plasma-surface-treated and then maintained in a vacuum in FIG. 9C.

That is, the plasma treatment apparatus according to the third embodiment of the present disclosure has an effect of maintaining the performance achieved through surface treatment.

Plasma Treatment Method According to the First Embodiment of the Present Disclosure Hereinafter, a plasma treatment method according to the first embodiment of the present disclosure will be described.

FIG. 10 is a flowchart illustrating the plasma treatment method according to the first embodiment of the present disclosure.

Referring to FIG. 10, the plasma treatment method according to the first embodiment of the present disclosure includes accommodating an accommodation container in which a target object is accommodated (S610), generating a path communicating with the inside of the accommodation container (S620), exhausting internal air of the accommodation container (S630), applying electric power for generating plasma to the accommodation container (S640), and venting the inside of the accommodation container (S640).

In operation S610, the accommodation container accommodating the target object is accommodated in the accommodation unit of the apparatus.

In operation S620, the path generation unit of the apparatus generates the path that communicates with the inside of the accommodation container accommodated in the accommodation unit.

Preferably, in operation S620, the path generation unit of the apparatus drives a needle that pierces one surface of the container to generate the path.

In operation S630, the exhaust unit of the apparatus exhausts the internal air of the accommodation container accommodated in the accommodation unit.

In operation S640, the treatment unit of the apparatus applies a voltage to the target object in the accommodation container accommodated in the accommodation unit, generates plasma in conjunction with the ground electrode formed on the outer surface of the accommodation container, and thus performs plasma surface treatment on the target object.

Preferably, in operation S640, the treatment unit of the apparatus irradiates, with ultraviolet rays, the target object in the accommodation container accommodated in the accommodation unit.

In operation S650, the exhaust unit of the apparatus vents the accommodation container when the plasma surface treatment of the target object is completed.

Preferably, when the plasma surface treatment of the target object is completed, the exhaust unit of the apparatus causes the internal air to be discharged, while maintaining a vacuum inside the accommodation container.

A plasma treatment apparatus according to an embodiment of the present disclosure may include: a accommodation unit for accommodating a container in which a target object is accommodated; an exhaust unit, which is connected to the accommodation unit and exhausts internal air of the container; and a treatment unit, which applies, to the container from which the internal air is exhausted by the exhaust unit, electric power for generating plasma in the container.

In some embodiments, the exhaust unit may include: a path generation unit for generating a path communicating with the inside of the container; and a pump for exhausting the internal air of the container through the path.

In some embodiments, the path generation unit may include: a needle for generating the path by piercing one surface of the container; and a driving unit for moving the needle.

In some embodiments, the plasma treatment apparatus may further include a housing that surrounds the accommodation unit, the path generation unit, and the treatment unit, and packs them to be independent of the pump.

In some embodiments, the plasma treatment apparatus may further include a connection unit that connects the pump to the housing such that the arrangement may be changed independently.

In some embodiments, the connection unit is rotatable such that, although the point and length of connection between the pump and the housing are fixed, the arrangement may be changed.

In some embodiments, the accommodation unit includes a first accommodation unit for accommodating a first container and a second accommodation unit for accommodating a second container, and the path generation unit includes a first path generation unit for generating a path communicating with the inside of the first accommodation unit and a second path generation unit for generating a path communicating with the inside of the second accommodation unit, and may further include a control unit that operates the first path generation unit or the second path generation unit based on whether the first container or the second container is accommodated.

In some embodiments, when the first container is accommodated, the control unit may open a valve of the first path generation unit, close a valve of the second path generation unit, and operate the pump.

In some embodiments, the exhaust unit vents, through the path generated by the path generation unit, the container in which plasma treatment is completed by the treatment unit, and may further include a filter in the path.

In some embodiments, the plasma treatment apparatus may further include an opening/closing unit for opening and closing the accommodation unit.

In some embodiments, the opening/closing unit may perform a closing operation to prevent external exposure of the accommodation unit when the apparatus is not operating, an opening operation to accommodate the container, and a fixing operation to fix the container in a treatment state of the treatment unit.

In some embodiments, the opening/closing unit may cover the accommodation unit to prevent separation of the container accommodated in the accommodation unit, for fixing the container.

In some embodiments, when the opening/closing unit is changed from a fixed state to an open state during operation of the apparatus, the treatment unit may stop applying the electric power, or the exhaust unit may stop exhausting.

In some embodiments, the opening/closing unit may include, on the outer surface thereof, a display unit for displaying an operation state of the apparatus.

In some embodiments, the treatment unit may include a first electrode unit that is in contact with one surface of the container exposed such that electricity flows to the target object, and then applies a voltage to the target object.

In some embodiments, the treatment unit may include a second electrode unit that is grounded on a surface adjacent to the outer surface of the container.

In some embodiments, the second electrode unit may be a needle that pierces one surface of the container to generate a path communicating with the inside of the container.

In some embodiments, the accommodation unit may include a fastening unit for fixing contact between the first electrode unit and one surface of the container that is exposed such that electricity flows to the target object.

A plasma treatment method according to an embodiment of the present disclosure includes: accommodating a container in which a target object is accommodated; exhausting internal air of the container; and applying electric power for generating plasma to the container from which the internal air is exhausted.

In some embodiments, the exhausting may include generating a path communicating with the inside of the container.

In some embodiments, the generating may include driving a needle that pierces one surface of the container to generate the path.

In some embodiments, the accommodating may include accommodating a first container in which a first target object is accommodated and accommodating a second container in which a second target object is accommodated, and may further include, based on whether the first container or the second container is accommodated, determining whether to generate a path communicating with the inside of the first container or to generate a path communicating with the inside of the second container.

In some embodiments, the plasma treatment method may further include, when plasma treatment of the target object is completed, venting the inside of the container.

In some embodiments, the applying of the electric power may further include contacting an electrode with one exposed surface of the container, such that electricity flows to the target object.

In some embodiments, the target object is an implant, and the plasma treatment method may further include irradiating the container with ultraviolet rays.

Plasma Treatment Container According to the First Embodiment of the Present Disclosure Hereinafter, a plasma treatment container according to the first embodiment of the present disclosure will be described.

FIG. 11 is a configuration diagram schematically illustrating the plasma treatment container according to the first embodiment of the present disclosure.

Referring to FIG. 11, the plasma treatment container according to the first embodiment of the present disclosure includes a fixing unit 120a, which is in contact with and fixes a target object 110a, and a cover 130a for accommodating the fixing unit 120a.

Preferably, the target object 110a is an implant fixture, and the plasma treatment container is an ampoule for accommodating an implant fixture.

Preferably, the cover 130a is transparent and made of polycarbonate.

FIG. 12 is a schematic cross-sectional view taken along line AA of FIG. 11, and FIG. 13 is a schematic cross-sectional view illustrating the plasma treatment container when a contact unit is inserted thereinto in FIG. 12.

Further referring to FIGS. 12 and 13, the fixing unit 120a comes into contact with a side of a contact unit 200a inserted into the cover 130a from the outside of the cover 130a.

Preferably, the contact unit 200a is connected to a power source to apply electricity to the fixing unit 120a.

Preferably, the fixing unit 120a and the target object 110a are made of a material through which electricity flows, and electricity applied from the contact unit 200a is connected to the target object 110a through the fixing unit 120a, such that the target object 110a becomes a power supply unit for generating plasma. As such, the target object 111a functions as a high-voltage part in plasma generation through dielectric barrier discharge.

Preferably, the contact unit 200a is a needle with a sharp tip, is made of a material through which electricity flows, and is equipped with an internal air flow path to simultaneously connect electricity and exhaust internal air.

Preferably, the cover 130a includes a first region 141a penetrated by the contact unit 200a. The first region 141a is made of an elastic material such that the inside of the cover 130a is sealed and maintains a vacuum state even when the contact unit 200a penetrates the first region 141a, and may return to its original shape to close the penetrated region.

Preferably, the internal air of the cover 130a is exhausted by the contact unit 200a to create a vacuum in the cover 130a, and the inside of the cover 130a is sealed to maintain the vacuum.

Preferably, the fixing unit 120a includes a protrusion 122-1a, which is convex toward the portion into which the contact unit 200a is inserted, and the protrusion 122-1a comes into contact with a side of the contact unit 200a as the contact unit 200a moves for insertion.

When manufacturing the plasma treatment container, the plasma treatment container may be manufactured while the cover 130a is filled with discharge gas.

The discharge gas may include helium gas, neon gas, argon gas, krypton gas, xenon gas, radon gas, xenon gas, nitrogen gas, hydrogen selenide gas, deuterium gas, fluorine gas, chlorine gas, bromine gas, iodine gas, hydrogen gas, mercury gas, or a combination thereof.

The discharge gas filled in the cover 130a as described above may be filled in the plasma treatment container by being made airtight by the cover 130a (e.g., an outer cover 132a) and a sealing member 140a.

When the plasma treatment container is manufactured, as the plasma treatment container is manufactured while being filled with the discharge gas, it may be determined, through the pressure of the discharge gas filled in the plasma treatment container, whether the plasma treatment container is damaged during distribution. In other words, in a case in which the plasma treatment container has been damaged due to a movement or the like during the distribution of the plasma treatment container, the discharge gas leaks out, thus the pressure of the discharge gas inside the plasma treatment container is measured to be low, and through this, it is possible to easily determine whether the plasma treatment container is damaged.

According to an embodiment, a sealing member 140b may be made of a styrene-based acrylonitrile butadiene styrene (ABS) material, a silicone material, or a mixture thereof, but is not limited thereto.

When plasma treatment is performed on the target object in the plasma treatment container by using a plasma treatment apparatus, the plasma treatment may be performed by varying a voltage condition according to the type of the discharge gas filled in the cover 130a or the pressure inside the plasma treatment apparatus.

Information about the type of discharge gas may be input to a QR code, barcode, or near field communication (RFID, NFC) provided in the plasma treatment container.

The pressure of the discharge gas, that is, the pressure inside the plasma treatment container, may be measured by a pressure sensor included in the plasma treatment container or a pressure sensor included in the plasma treatment apparatus.

As described above, by performing the plasma treatment by varying the voltage condition according to an internal environment of the plasma treatment container, more effective plasma treatment may be performed on the target object.

FIG. 14 is a diagram obtained by enlarging B of FIG. 13.

Further referring to FIG. 14, an inner angle b1 of an insertion groove formed by the protrusion 122-1a is greater than an inner angle b2 of the tip of the contact unit 200a.

That is, the contact unit 200a is inserted into the insertion groove formed by the protrusion 122-1a at a certain depth, but is caught and brought into contact with the protrusion 122-1a due to the size of the inner angle thereof.

Preferably, the inner angle b1 of the insertion groove formed by the protrusion 122-1a is greater than the inner angle b2 of the tip of the contact unit 200a such that, in a state in which the contact unit 200a is inserted into the insertion groove and the tip of the contact unit 200a is not in contact with the fixing unit 120a, the side of the contact unit 200a is in contact with the protrusion 122-1a, and the insertion groove has a certain depth.

As such, the protrusion 122-1a prevents the tip of the contact unit 200a from coming into contact with other members and thus being damaged, and is in contact with the side of the contact unit 200a and thus prevents further insertion thereof, to prevent the tip of the contact unit 200a from coming into contact with other members.

In particular, because the protrusion 122-1a is in line contact or surface contact with the side of the contact unit 200a, it is unnecessary to precisely adjust the degree of insertion of the contact unit 200a. This is because, in order for the tip of the contact unit 200a to make point contact, precise tolerance management is required, whereas, in order for the side of the contact unit 200a to make line contact or surface contact, less precise tolerance management is required, and thus, reliability of electrical contact may be achieved.

Preferably, the contact unit 200a is connected not to apply electricity to the target object 110a through point contact that causes damage to the tip, but to apply electricity to the target object 110a through line contact or surface contact of the side thereof.

Preferably, the fixing unit 120a includes a first member 121a to be in contact with the target object 110a, and a second member 122a coupled to the first member.

Preferably, the first member 121a is a stopper, is made of titanium, which is the same material as that of the target object 110a, and fixes the target object 110a not to move up and down or rotate.

Preferably, the second member 122a is made of aluminum, and is physically coupled to the first member 121a.

As such, the contact unit 200a may reduce damage by contacting the second member 122a having a lower hardness than that of the first member 121a.

Preferably, the first member 121a and the second member 122a are made of a material through which electricity flows, and transmit, to the target object 110a, electricity that is applied as the second member 122a comes into contact with the contact unit 200a.

Preferably, the first member 121a includes a D-cut portion 121-1a, a portion of the outer circumferential surface of which is cut into a plane shape, to fix the target object 110a not to rotate.

Preferably, the second member 122a includes a D-cut portion (not shown), a portion of the outer circumferential surface of which is cut into a plane shape, to fix the target object 110a not to rotate.

Preferably, the cover 130a includes an inner cover 131a for accommodating the target object 110a and the fixing unit 120a, and the outer cover 132a for accommodating the inner cover 131a, and the inner cover 131a and the outer cover 132a are spaced apart from each other by a certain distance.

Preferably, the inner cover 131a includes a path for moving internal air of the inner cover 131a toward the outer cover 132a.

As such, when air is exhausted by the contact unit 200a, both the internal air of the inner cover 131a and the internal air of the outer cover 132a are exhausted.

As such, the inner cover 131a has a structure for applying electricity to the target object 110a and a shape for dielectric barrier discharge, and the outer cover 132a is sealed from the outside of the container to provide a structure capable of creating and maintaining a vacuum, and provides safety of insulation from the outside.

Preferably, the outer cover 132a is a vacuum dielectric barrier discharge cover, is transparent, and is made of a polycarbonate material.

Preferably, the inner cover 131a is a vacuum dielectric barrier discharge cover, is transparent, and is made of a polycarbonate material.

Preferably, the plasma treatment container according to the first embodiment of the present disclosure further includes the sealing member 140a connected to the cover 130a.

Preferably, the sealing member 140a includes a penetration portion 141a to be penetrated by the contact unit 200a, and the penetration portion 141a is made of an elastic material such that, even when the penetration portion 141a is penetrated by the contact unit 200a, the inside of the cover 130a is sealed to maintain a vacuum state.

Preferably, the sealing member 140a and the penetration portion 141a are made of a styrene-based ABS material, a silicone material having a hardness of 110, or a mixture thereof.

Preferably, the plasma treatment container according to the first embodiment of the present disclosure further includes an elastic O-ring 150a or a sealing pad, between the sealing member 140a and the cover 130a.

Preferably, the sealing member 140a is screwed to the cover 130a, and as the internal air is exhausted, the O-ring 150a or the sealing pad is pressed to seal against a vacuum leak.

Preferably, the O-ring 150a or the sealing pad is made of a fluorocarbon material. Preferably, the coupling between the inner cover 131a and the sealing member 140a is enhanced as the internal air of the outer cover 132a is exhausted. The inner cover 131a is detachably coupled to the sealing member 140a. For example, the inner cover 131a is fitted and coupled to the sealing member 140a, and is sealed such that a vacuum therein is maintained.

Preferably, the coupling between the inner cover 131a and the outer cover 132a is enhanced as the internal air of the outer cover 132a is exhausted. The inner cover 131a is detachably coupled to the outer cover 140a, and is sealed such that a vacuum therein is maintained.

Preferably, as the internal air of the outer cover 132a is exhausted, the pressure of a point, line, or surface in contact with the outer cover 132a or the sealing member 140a increases, and thus, the fixation of the inner cover 131a is enhanced. For example, a cap unit 170a is elastic to connect the outer cover 132a to the inner cover 131a, and as the internal air of the outer cover 132a is exhausted, the cap unit 170a is pressed with a certain pressure to enhance the coupling between the outer cover 132a and the inner cover 131a. Conversely, as the inside of the outer cover 132a is vented and thus the pressure of the cap unit 170a is decreased, the elasticity of the cap unit 170a is restored to weakening the coupling between the outer cover 132a and the inner cover 131a.

Preferably, as the inside of the outer cover 132a is vented, the pressure of the point, line, or surface in contact with the outer cover 132a or the sealing member 140a decreases, and thus, the fixation of the inner cover 131a is weakened.

As such, when venting the inside of the plasma treatment container with a vacuum therein after the plasma surface treatment of the target object 110a accommodated in the plasma treatment container is completed, a user is able to detach the inner cover 131a from the container without touching the inner cover 131a.

In particular, when the user vents the inside of the plasma treatment container and then separates the outer cover 132a and the sealing member 140a, the inner cover 131a detachably coupled to the sealing member 140a is separated from the outer cover 132a. Thereafter, the user may hold a handle 172a of the cap unit 172a and separates the inner cover 131a connected through an inner cap unit 171a from the sealing member 140a to take out the target object 110a.

Preferably, the target object 110a is connected to a guide unit 180a or the inner cap unit 171a, and may be located on the side of the handle 172a when the inner cover 131a is separated from the sealing member 140a through the handle 172a.

That is, the inner cover 131a may be moved to an operating room, an operating table or a tray without contacting the user, and thus prevent infection in this process.

Preferably, the plasma treatment container according to the first embodiment of the present disclosure further includes the guide unit 180a made of titanium, which is the same material as that of the target object 110a, for enhancing the fixation of the target object 110a.

Preferably, the target object 110a is fixed as a lower portion thereof is in contact with the first member 121a and an upper portion thereof is in contact with the guide unit 180a.

Preferably, the plasma treatment container according to the first embodiment of the present disclosure further includes the cap unit 170a connected to the guide unit 180a.

Preferably, the cap unit 170a is detachably connected to the guide unit 180a, the guide unit 180a is detachably connected to the target object 110a, and thus, by pulling the cap unit 170a toward the outside of the container, the target object 110a and the guide unit 180a may be separated from the container without contacting the hand of the user.

Preferably, the cap unit 170a includes the inner cap unit 171a that covers an upper portion of the inner cover 131a, and the handle 172a in contact with the outer cover 132a for applying a pressing force to prevent separation of the inner cap unit 171a.

Preferably, the inner cap unit 171a is made of a styrene-based ABS material, and the handle 172a is made of an opaque polycarbonate material.

Preferably, the plasma treatment container according to the first embodiment of the present disclosure further includes a path portion 160a for a movement path for the contact unit 200a having pierced and been inserted into the penetration portion 141a to contact the protrusion 122-1a.

Plasma Treatment Apparatus According to the Fourth Embodiment of the Present Disclosure Hereinafter, a plasma treatment apparatus according to the fourth embodiment of the present disclosure will be described.

FIG. 15 is a configuration diagram schematically illustrating the plasma treatment apparatus according to the fourth embodiment of the present disclosure.

Referring to FIG. 15, the plasma treatment apparatus according to the fourth embodiment of the present disclosure includes an accommodation unit 320a for accommodating a container 310a in which a target object 311a is accommodated, a contact unit 330a electrically connected to the target object 311a, and a power supply unit 340a that applies, to the target object 311a through the contact unit 330a, power for generating plasma.

Preferably, the target object 311a is an implant fixture, and the container 310a is an ampoule for accommodating an implant fixture.

Preferably, the contact unit 330a is a needle including a tip 331a capable of penetrating the outer surface of the container 310a, and is made of a material through which electricity flows.

Preferably, the contact unit 330a includes an air circulation path therein for exhausting internal air of the container 310a. That is, the contact unit 330a has a hollow tube shape.

FIG. 16 is a configuration diagram schematically illustrating the plasma treatment apparatus when the contact unit is inserted into the container in FIG. 15.

Further referring to FIG. 16, the contact unit 330a is inserted into the container 310a such that a side of the contact unit 330a is electrically connected to the target object 311a.

Preferably, the contact unit 330a is inserted into an insertion groove of a member 312a that is electrically connected to the target object 311a, and thus, the side of the contact unit 330a is electrically connected to an inner protrusion of the member 312a.

Preferably, a hole 332a formed in the contact unit 330a for exhausting the internal air of the container 310a is formed to be farther from the target object 311a than is electrical contact between the contact unit 330a and the target object 311a.

Preferably, the hole 332a is formed at a position closer to the plasma treatment apparatus than is a line or a surface where the side of the contact unit 330a and the member 312a come into contact with each other. As such, exhausting through the hole 332a enhances the adhesion between the side of the contact unit 330a and the line or surface in contact with the member 312a, and solves an issue that all internal air of the container 310a is not exhausted.

Preferably, the plasma treatment apparatus according to the fourth embodiment of the present disclosure further includes a ground electrode unit 321a, which is adjacent to the outer circumferential surface of the container 310a, and is connected to the power supply unit 340a and is grounded when the container 310a is accommodated.

Preferably, the accommodation unit 320a further includes a fixing unit (not shown) in which the container 310a is accommodated and fixed.

Preferably, the accommodation unit 320a further includes a sensing unit (not shown) that determines whether the container 310a is accommodated, and prevents an operation error of the apparatus according to whether the container 310a is accommodated determined by the sensing unit.

Preferably, the plasma treatment apparatus according to the fourth embodiment of the present disclosure further includes an exhaust unit 350a connected to an air flow path of the contact unit 330a to exhaust internal air of the container 310a.

Preferably, the contact unit 330a is made of a material through which electricity flows, and further includes an insulation unit 360a in a path connected to the exhaust unit 350a of the contact unit 330a.

Preferably, the power supply unit 340a is controlled by a power control unit 381a, and the power control unit 381a controls through information measured by a current measurement unit 383a that monitors a current by the power supply unit 340a.

Preferably, the accommodation unit 320a includes the ground electrode unit 321a and a dielectric unit 322a.

Preferably, the dielectric unit 322a is in contact with the ground electrode unit 321a, and is formed to be closer to the container 310a than is the ground electrode unit 321a.

Preferably, the plasma treatment apparatus according to the fourth embodiment of the present disclosure further includes a movement control unit 382a that controls the movement of the contact unit 330a.

Preferably, the movement control unit 382a uses information received by a lower limit sensor and an upper limit sensor to control the movement of the contact unit 330a through a defined path.

Preferably, the plasma treatment apparatus according to the fourth embodiment of the present disclosure further includes a pressure sensor 371a that measures the pressure of exhausted air.

Preferably, the plasma treatment apparatus according to the fourth embodiment of the present disclosure includes a valve 372a for driving or stopping an exhaust operation.

Preferably, the exhaust unit 350a is configured independently by a housing spaced apart from the plasma treatment apparatus.

Preferably, the exhaust unit 350a includes an exhaust pump 351a, a mist trap 352a that collects oil drawn out by the exhaust pump 351a, and an ozone filter 353a and a HEPA filter 351a for preventing contamination of air drawn out of the exhaust unit 350a.

Plasma Treatment Method According to the Second Embodiment of the Present Disclosure Hereinafter, a plasma treatment method according to the second embodiment of the present disclosure will be described.

FIG. 17 is a flowchart illustrating the plasma treatment method according to the second embodiment of the present disclosure.

Referring to FIG. 17, the plasma treatment method according to the second embodiment of the present disclosure includes accommodating a container in which a target object is accommodated (S410a), moving a contact unit to the inside of the container (S420a), exhausting internal air of the container (S430a), and applying power to the target object (S440a).

In operation S410, the container accommodating the target object is accommodated in the accommodation unit of the apparatus.

In operation S420, the contact unit of the apparatus moves to the inside of the container such that a side of the contact unit is electrically connected to the target object.

In operation S430, the contact unit of the apparatus exhausts the internal air of the container.

In operation S440, a power supply unit of the apparatus applies, to the target object through the contact unit, power for generating plasma.

Preferably, the plasma treatment method according to the second embodiment of the present disclosure further includes detecting whether the container is accommodated, and applying power only when the container is accommodated.

A plasma treatment container according to an embodiment of the present disclosure may include: a fixing unit, which is in contact with and fixes a target object; and a cover for accommodating the fixing unit, and the fixing unit may be in contact with a side of a contact unit inserted into the cover from the outside of the cover, and thus receive electricity from the contact unit.

In some embodiments, the fixing unit and the target object may be made of a material through which electricity flows, and thus, the target object may serve as a power supply unit for generating plasma by using electricity applied from the contact unit.

In some embodiments, the cover includes a first region to be penetrated by the contact unit, and the first region is made of an elastic material such that the inside of the cover is sealed even when the first region is penetrated by the contact unit, and thus, a vacuum state may be maintained.

In some embodiments, internal air of the cover may be exhausted by the contact unit such that the inside of the cover may be in a vacuum state.

In some embodiments, the fixing unit includes an inwardly convex protrusion, and the protrusion may be in contact with a side of the inserted contact unit.

In some embodiments, the fixing unit may include: a first member in contact with the target object; and a second member coupled to the first member, and the first member and the second member are made of a material through which electricity flows, such that the second member may be in contact with the contact unit and thus transmit electricity applied thereto, to the target object.

In some embodiments, an inner angle of the insertion groove formed by the protrusion may be greater than an inner angle of the tip of the contact unit.

In some embodiments, the first member may include a D-cut portion, a portion of the outer circumferential surface of which is cut into a plane shape, to fix the target object not to rotate.

In some embodiments, the cover may include: an inner cover for accommodating the target object and the fixing unit; and an outer cover for accommodating the inner cover, and the inner cover and the outer cover may be spaced apart from each other by a certain distance.

In some embodiments, the plasma treatment container further includes a sealing member connected to the cover, the sealing member includes a penetration portion to be penetrated by the contact unit, and the penetration portion made of an elastic material such that, even when the penetration portion is penetrated by the contact unit, the inside of the cover is sealed to maintain a vacuum state.

In some embodiments, the plasma treatment container may further include an elastic O-ring or a sealing pad between the sealing member and the cover.

In some embodiments, the inner cover may include a path for moving internal air of the inner cover toward the outer cover.

In some embodiments, the plasma treatment container may further include: a sealing member connected to the outer cover; and an elastic O-ring or a sealing pad between the sealing member and the outer cover, the sealing member may be connected to the inner cover, the inner cover may be connected to the outer cover through an elastic cap unit, the inside of the outer cover may be sealed by the elastic O-ring or the sealing pad, as the inner air of the outer cover is exhausted, so as to maintain a vacuum state, the internal pressure of the outer cover may increase as the internal air of the outer cover is exhausted, so as to enhance the coupling between the inner cover and the outer cover through the cap unit, and the internal pressure of the outer cover may decrease as the inside of the outer cover is vented, such that the coupling between the inner cover and the outer cover may be weakened by the cap unit restoring its elasticity.

The plasma treatment apparatus according to an embodiment of the present disclosure may include: a accommodation unit for accommodating a container in which a target object is stored; a contact unit to be inserted into the container such that a side thereof is electrically connected to the target object; and a power supply unit that applies power for generating plasma to the target object through the contact unit.

In some embodiments, the contact unit may include a tip capable of penetrating the outer surface of the container.

In some embodiments, the contact unit may include an air flow path therein for exhausting internal air of the container.

In some embodiments, a hole formed in the contact unit to exhaust the internal air of the container may be formed at a position farther from the target object than is an electrical contact between the contact unit and the target object.

In some embodiments, the plasma treatment apparatus may further include an exhaust unit connected to the air flow path of the contact unit to exhaust the internal air of the container, and the contact unit may be made of a material through which electricity flows, and may further include an insulation unit in a path connected to the exhaust unit of the contact unit.

In some embodiments, the plasma treatment apparatus may further include a ground electrode unit, which is adjacent to the outer circumferential surface of the container, is connected to the power supply unit, and is grounded.

In some embodiments, the accommodation unit may further include a fixing unit that fixes the accommodated container.

The plasma treatment method according to an embodiment of the present disclosure may include: accommodating a container in which a target object is accommodated; moving a contact unit to the inside of the container such that a side of contact unit is electrically connected to the target object; exhausting internal air of the container through the contact unit; and applying, to the target object through the contact unit, power for generating plasma.

In some embodiments, the plasma treatment method may further include detecting whether the container is accommodated, and, when the container is accommodated, applying the power.

Plasma Treatment Container According to the Second Embodiment of the Present Disclosure Hereinafter, a plasma treatment container according to the second embodiment of the present disclosure will be described.

FIG. 18 is a perspective view of the plasma treatment container according to the second embodiment of the present disclosure, FIG. 19 is a cross-sectional view taken along line BB of FIG. 18, and FIG. 20 is a diagram illustrating a state in which a contact unit is inserted into the plasma treatment container in FIG. 19.

Referring to FIGS. 18 to 20, a plasma treatment container 100*b* according to the second embodiment of the present disclosure may include an implant body 110*b*, a fixing unit 120*b*, a cover 130*b*, a sealing member 140*b*, a penetration portion 141*b*, an elastic member 150*b*, a path portion 160*b*, a cap unit 170*b*, and a guide unit 180*b*.

The plasma treatment container 100*b* may store the implant body 110*b* accommodated therein.

The plasma treatment container 100*b* may be referred to as an implant ampoule or the like.

For example, the plasma treatment container 100*b* may include an implant storage container.

The implant body 110*b* may be an object to be stored in the plasma treatment container 100*b* and also may be a target object of plasma treatment when the plasma treatment is performed on the plasma treatment container 100*b*.

According to an embodiment, the implant body 110*b* may refer to a wide range of parts of an implant required to be plasma-treated. For example, the implant body 110*b* may be an implant fixture, but is not limited thereto.

The fixing unit 120*b* may be in contact with the implant body 110*b* to fix the implant body 110*b*.

According to an embodiment, the fixing unit 120*b* may include a first fixing member 121*b* and a second fixing member 122*b*.

The first fixing member 121*b* is formed to come into contact with the implant body 110*b* to fix the implant body 110*b* not to move in vertical and horizontal directions or rotational directions.

According to an embodiment, the first fixing member 121*b* may be implemented with a material through which electricity flows.

According to an embodiment, the first fixing member 121*b* may be made of the same material as that of the implant body 110*b* (e.g., titanium).

According to an embodiment, the first fixing member 121*b* may include a D-cut portion 121-1*b*, a portion of the outer circumferential surface of which is cut into a plane shape. Here, the D-cut portion 121-1*b* is engaged with the lower end of the implant body 110*b* to prevent the implant body 110*b* from moving.

The second fixing member 122*b* is formed to be in contact with the first fixing member 122*b*. The second fixing member 122*b* has a structure in which, when a contact unit 200*b* for applying a voltage is inserted into the plasma treatment container 100*b*, the contact unit 200*b* may stably come into contact with the second fixing member 122*b* without damage.

According to an embodiment, the second fixing member 122*b* may be implemented with a material (e.g., aluminum) having a relatively low hardness that that of the first fixing member while allowing electricity to flow therethrough.

Referring to FIG. 20 together, when a voltage is applied through the contact unit 200*b* to plasma-treat the implant body 110*b*, the contact unit 200*b* may come into contact with the fixing unit 120*b*, for example, the second fixing member 122*b* of the fixing unit 120*b*, so as to apply a voltage. The voltage applied to the fixing unit 120*b* may be transmitted to the implant body 110*b*, and the implant body 110*b* may operate as one electrode used for dielectric barrier discharge as the voltage is applied.

According to an embodiment, the fixing unit 120*b*, for example, the first fixing member 121*b* and the second fixing member 122*b* constituting the fixing unit 120*b* may be made of a material through which electricity flows.

According to an embodiment, the fixing unit 120*b* may include a protrusion 122-1*b* convexly protruding toward a portion into which the contact unit 200*b* is inserted. When the contact unit 200*b* is inserted, the contact unit 200*b* may come into contact with the side of the contact unit 200*b*, and thus, a voltage may be applied to the protrusion 122-1*b*.

The cover 130*b* may accommodate the implant body 110*b* therein.

According to an embodiment, the cover 130*b* may be formed of a transparent material. According to an embodiment, the cover 130*b* may be formed of a polycarbonate material.

The cover 130*b* may be connected to the sealing member 140*b* to be described below to keep the inside thereof airtight.

The cover 130*b* may include an inner cover 131*b* for accommodating the implant body 110*b*, and an outer cover 132*b* for accommodating the inner cover 131*b*.

According to an embodiment, the inner cover 131*b* and the outer cover 132*b* may be spaced apart from each other by a certain distance.

According to an embodiment, the inner cover 131*b* may include a path for moving internal gas of the inner cover 131*b* to the outer cover 132*b*. In this case, gas may freely move between the inside and outside of the inner cover 131*b*.

According to an embodiment, each of the inner cover 131*b* and the outer cover 132*b* may be formed of a polycarbonate material.

According to an embodiment, any one of the inner cover 131*b* or the outer cover 132*b* may be omitted.

The sealing member 140*b* may be connected to the cover 130*b* to keep airtight an internal gas environment filled with discharge gas used for plasma discharge according to a preset composition ratio.

According to an embodiment, an elastic member 150*b* may be included between the sealing member 140*b* and the cover 130*b*, for sealing a boundary between the sealing member 140*b* and the cover 130*b*.

According to an embodiment, the internal gas environment may be maintained at an atmospheric pressure lower than the atmospheric pressure, and in this case, the elastic member 150*b* is compressed according to the pressure generated due to the difference between the atmospheric pressure and the pressure inside the plasma treatment container 100*b*, and thus maintains airtightness.

According to an embodiment, the elastic member 150*b* may be an O-ring or a sealing pad.

According to an embodiment, the internal gas environment may include an environment, such as the composition ratio of the discharge gas or the internal pressure of the discharge gas.

According to an embodiment, the sealing member 140*b* may be screwed to the cover 1310*b*.

The discharge gas may fill the internal space made airtight by the cover 130*b* (e.g., the outer cover 132*b*) and the sealing member 140*b*.

According to an embodiment, the discharge gas may include helium gas, neon gas, argon gas, krypton gas, xenon gas, radon gas, xenon gas, nitrogen gas, hydrogen selenide gas, deuterium gas, fluorine gas, chlorine gas, bromine gas, iodine gas, hydrogen gas, mercury gas, or a combination thereof.

According to an embodiment, the sealing member 140*b* may be made of a styrene-based ABS material, a silicone material, or a mixture thereof, but is not limited thereto.

The penetration portion 141*b* and the path portion 160*b* may be formed at a lower portion of the sealing member 140*b*.

The penetration portion 141*b* is made of an elastic material, and may be formed such that a gas flow path is temporarily formed therein when injecting the discharge gas into the plasma treatment container 100*b*, and then the penetration portion 141*b* returns to its original shape to close the gas flow path.

The penetration portion 141*b* is formed to be penetrated by the contact unit 200*b*, and when penetrated by the contact unit 200*b*, the penetrated portion comes into close contact with the contact unit 200*b* and thus, the internal gas environment of the discharge gas filled in the internal space made airtight by the cover 130*b* and the sealing member 140*b* may be kept airtight.

According to an embodiment, the penetration portion 141*b* may be made of a styrene-based ABS material, a silicone material, or a mixture thereof, but is not limited thereto.

The path portion 160*b* may provide a path through which the contact unit 200*b* moves after passing through the penetration portion 141*b* when the contact unit 200*b* is inserted into the plasma treatment container 100*b*.

The cap unit 170*b* may include an inner cap unit 171*b* and a handle 172*b*. The inner cap unit 171*b* is made of an elastic material and thus be kept pressed between the inner cover 131*b* and the outer cover 132*b* when the cover 130*b* and the sealing member 140*b* are sealed.

According to an embodiment, the inner cap unit 171*b* may be made of a styrene-based ABS material, a silicone material, or a mixture thereof, but is not limited thereto.

When the inside of the plasma treatment container 100*b* is vented after the plasma treatment of the implant body 110*b* in the plasma treatment container 100*b* is completed, due to the restoring force of the inner cap unit 171*b*, the inner cover 131*b* and the outer cover 132*b* receive a force in a direction away from each other. Accordingly, the inner cover 131*b* and the outer cover 132*b* may be separated from each other without using hands.

After the inner cover 131b and the outer cover 132b are separated from each other, the user may separate the inner cover 131b in which the plasma-treated implant body 110b is accommodated, from the sealing member 140b by pulling the handle 172b.

According to the embodiment, the implant body 110b is connected to the guide unit 180b or the inner cap unit 171b, such that, when the user pulls the handle 172b and thus the inner cover 131b is separated from the sealing member 140b, the implant body 110b may be located on the side of the inner cover 131b.

Because the inner cover 131b is separated from the outer cover 132b at the final stage of use, it is possible to minimize external infection of the inner cover 131b by blocking contact with other than a person who finally handles the implant body 110b.

According to an embodiment, the cap unit 170b may be connected to the guide unit 180b, and the guide unit 180b may be in contact with an upper portion of the implant body 110b to fix the implant body 110b.

A display unit 190b for displaying information about the internal gas environment may be included on the outer surface of the sealing member 140b.

According to an embodiment, the display unit 190b may be arranged in the cover 130b, for example, the outer surface of the outer cover 132b.

According to an embodiment, the display unit 190b may display at least one of the type of the discharge gas filled in the plasma treatment container 100b, the composition ratio of the discharge gas, the internal pressure of the discharge gas, and the use-by date of the discharge gas.

According to an embodiment, the display unit 190b may be a QR code, barcode, or near field communication (RFID, NFC).

When the container 100b is accommodated in the accommodation unit 120, the accommodation unit 120 may determine, through the display unit 190b of the container 100b, whether the container 100b is accommodated, the type of the container 100b, whether the container 100b is a genuine product, whether the container 100b is accurately accommodated in a target position, the type of a target object accommodated in the container 100b, the number of times the container 100b is used for plasma treatment, etc.

FIG. 21 is an enlarged view of region C of FIG. 20.

Referring to FIGS. 18 to 21, according to an embodiment, an inner angle b1b of an insertion groove formed by the protrusion 122-1b may be greater than an inner angle b2b of the tip of the contact unit 200b.

In this case, the contact unit 200b is inserted, to a certain depth, into the insertion groove formed by the protrusion 122-1b, and then is caught by and comes into contact with the protrusion 122-1b.

According to an embodiment, the size of the inner angle b1b of the insertion groove formed by the protrusion 122-1b may be set such that a side of the contact unit 200b is in contact with the protrusion 122-1b in a state in which the contact unit 200b is inserted and the tip of the contact unit 200b is not in contact with the first fixing member 121b. That is, the protrusion 122-1b may be implemented such that the side of the contact unit 200b may be stably in contact while preventing the tip of the contact unit 200b from being damaged due to contact with other members.

According to an embodiment, the inner angle b1b of the insertion groove may equal to the inner angle b2b of the tip.

Because the protrusion 122-1b comes into line or surface contact with the side of the contact unit 200b, even when there is a slight error in the degree of insertion of the contact unit 200b, a voltage may be applied through stable contact. That is, as the side of the contact unit 200b comes into line contact or surface contact with the protrusion 122-1b, the contact unit 200b allows the voltage to be applied to the implant body 110b through the fixing unit 120b.

Plasma Treatment Apparatus According to the Fifth Embodiment of the Present Disclosure Hereinafter, a plasma treatment apparatus according to the fifth embodiment of the present disclosure will be described.

FIG. 22 is a schematic diagram of the plasma treatment apparatus according to the fifth embodiment of the present disclosure, and FIG. 23 is a diagram illustrating a state in which a contact unit is inserted into a plasma treatment container in the plasma treatment apparatus of FIG. 22.

Referring to FIGS. 22 and 23, a plasma treatment apparatus 1000b according to the fifth embodiment of the present disclosure may include a plasma treatment container 310b, an accommodation unit 320b, a ground electrode unit 321b, a dielectric unit 322b, a contact unit 330b, a driving unit 340b, an insulation unit 342b, a power supply unit 350b, a current measurement unit 352b, and a power control unit 354b.

For example, the plasma treatment apparatus 1000b may include a plasma treatment system.

According to an embodiment, the accommodation unit 320b, the ground electrode unit 321b, the dielectric unit 322b, the contact unit 330b, the driving unit 340b, the insulation unit 342b, the power supply unit 350b, the current measurement unit 352b, and the power control unit 354b may be implemented as a plasma treatment apparatus separate from the plasma treatment container 310b.

In the plasma treatment container 310b of FIGS. 22 and 23, only an implant body 311b and a fixing unit 312b accommodated in a cover are illustrated for convenience of description, but the plasma treatment container 310b may be the plasma treatment container 100b according to the second embodiment of the present disclosure illustrated in FIGS. 18 to 20.

The accommodation unit 320b of the plasma treatment apparatus provides a space for accommodating the plasma treatment container 310b.

The accommodation unit 320b may include the ground electrode unit 321b and the dielectric unit 322b arranged adjacent to the outer circumferential surface of the plasma treatment container 310b.

The ground electrode unit 321b is connected to a ground terminal of the power supply unit 350b to function as a ground electrode.

The dielectric unit 322b may be made of a dielectric material and included in the accommodation unit 320b to increase the effect of plasma barrier discharge, but the dielectric unit 322b may not be included according to an embodiment.

According to an embodiment, the dielectric unit 322b may be formed to be closer to the plasma treatment container 310b than is the ground electrode unit 321b.

The contact unit 330b may be inserted into the plasma treatment container 310b, such that a side of the contact unit 330b may come into contact with the fixing unit 312b. Accordingly, the contact unit 330b may apply, to the implant body 311b through the fixing unit 312b, a voltage applied from the power supply unit 350b.

The driving unit 340b may control movement of the contact unit 330b, for example, movement in a vertical direction.

According to an embodiment, the driving unit 340*b* may use sensing information collected from a lower limit sensor and an upper limit sensor such that the contact unit 330*b* may move a predetermined distance through a predetermined path.

According to an embodiment, the driving unit 340*b* may include a motor for moving the contact unit 330*b*.

According to another embodiment, the driving unit 340*b* may be replaced with a nonpowered elastic material. In this case, the position of the contact unit 330*b* is fixed through the elastic material, and when the plasma treatment container 310*b* is inserted into the accommodation unit 320*b*, the contact unit 330*b* may be inserted into the plasma treatment container 310*b* by using the restoring force of the elastic material. For example, the driving unit 340*b* may include a spring having a certain elasticity.

The insulation unit 342*b* may maintain insulation between the contact unit 330*b* made of a material through which electricity flows, and another component (e.g., the driving unit 340*b*).

The power supply unit 350*b* may apply power for generating plasma to the implant body 311*b* through the contact unit 330*b*.

The current measurement unit 352*b* may monitor a current provided by the power supply unit 350*b* and transmit information about the monitored current to the power control unit 354*b*.

The power control unit 354*b* may control supplied power by using the information about the monitored current transmitted from the current measurement unit 352*b*.

The plasma treatment container according to an embodiment of the present disclosure may include an implant body, a cover for accommodating the implant body therein, and a sealing member connected to the cover to keep airtight an internal gas environment filled with discharge gas to be used for plasma discharge according to a preset composition ratio.

According to an embodiment, the plasma treatment container may further include an elastic member for sealing a boundary between the sealing member and the cover.

According to an embodiment, the elastic member may be an elastic O-ring or a sealing pad.

According to an embodiment, the sealing member may include a penetration portion, which is made of an elastic material such that a gas flow path is temporarily formed therein when injecting the discharge gas into the cover, and then the penetration portion returns to its original shape to close the gas flow path.

According to an embodiment, a display unit for displaying information about the internal gas environment may be further included on the outer surface of the sealing member or the outer surface of the cover.

According to an embodiment, the display unit may display at least one of the type of the discharge gas filled in the plasma treatment container, the composition ratio of the discharge gas, the internal pressure of the discharge gas, and the use-by date of the discharge gas.

According to an embodiment, the plasma treatment container may further include a fixing unit connected to the implant body to fix the implant body.

According to an embodiment, the fixing unit may include a first fixing member connected to the implant body, and a second fixing member coupled to the first fixing member.

According to an embodiment, the first fixing member and the second fixing member are made of a material through which electricity flows, such that a voltage applied to the second fixing member may be transmitted to the implant body.

According to an embodiment, the implant body may operate as one electrode used for dielectric barrier discharge as a voltage is applied.

According to an embodiment, the discharge gas may include helium gas, neon gas, argon gas, krypton gas, xenon gas, radon gas, xenon gas, nitrogen gas, hydrogen selenide gas, deuterium gas, fluorine gas, chlorine gas, bromine gas, iodine gas, hydrogen gas, mercury gas, or a combination thereof.

According to an embodiment, the cover may include an inner cover for accommodating the implant body, and an outer cover for accommodating the inner cover, and the inner cover and the outer cover may be spaced apart from each other by a certain distance.

According to an embodiment, the inner cover may be provided with a handle formed in a protruding structure.

According to an embodiment, the inner cover may include a path for circulating gas between the inner cover and the outer cover.

Plasma Treatment Container According to the Third
Embodiment of the Present Disclosure Hereinafter, a plasma treatment container according to the third embodiment of the present disclosure will be described.

FIG. 24 is a cross-sectional view and an exploded view of the plasma treatment container according to the third embodiment of the present disclosure, and FIG. 25 is a diagram for describing a form in which an external ground electrode or power supply electrode is inserted into and brought into contact with the plasma treatment container of FIG. 24.

For convenience of description, FIG. 24 illustrates a storage container 100*c* and an external electrode 330*c*, together with a plasma treatment container 200*c*.

Referring to FIG. 24, the plasma treatment container 200*c* may serve as an auxiliary apparatus for surface-treating, through the external electrode 330*c*, of contents CNT stored in the storage container 100*c*.

According to an embodiment, the contents CNT may have various forms, such as a combination of a plurality of particles, a solid mass, or a liquid, and may refer to a wide range of materials to be stored in the storage container 100*c* then surface-treated.

For example, various materials that may be surface-treated, such as bone graft materials and plant seeds, may correspond to the contents CNT, and the scope of the present disclosure should not be construed as being limited by the type of the contents CNT.

For example, the plasma treatment container 200*c* may include an auxiliary apparatus for surface treatment of contents.

The external electrode 330*c* may be formed as a ground electrode or a power supply electrode. Despite what it is called, the external electrode 330*c* may exhaust internal gas of the storage container 100*c* through the plasma treatment container 220*c*. The external electrode 330*c* may have a hole 330-Hc and a passage for exhausting the internal gas of the storage container 100*c*. A content surface treatment apparatus including the external electrode 330*c* will be described below with reference to FIGS. 26 and 27.

The plasma treatment container 200*c* includes an exhaust unit 210*c*, a body unit 220*c*, and a first airtight unit 230*c*.

The exhaust unit 210*c* is form to be inserted into the storage container 100*c* storing the contents CNT, and may include a passage 212-PHc for exhausting internal gas of the storage container 100c while being inserted into the storage container 100c.

According to an embodiment, the exhaust unit 210c may be formed in a needle shape, to penetrate a cap 110c of the storage container 100c in a state in which the cap 110c is closed, and then is inserted into the storage container 100c. In this case, the exhaust unit 210c may penetrate at least a portion of the storage container 100c, for example, a region of the storage container 100c formed of an elastic material (e.g., the cap 110c).

The exhaust unit 210c may include an insertion unit 212c protruding to be inserted into the storage container 100c, and a contact unit 213c formed to come into contact with the external electrode 330c.

The insertion unit 212c may have a hole 212-Hc and the passage 212-PHc for exhausting the internal gas of the storage container 100c while being inserted into the storage container 100c. The internal gas sucked through the hole 212-Hc may be exhausted through the passage 212-PHc.

According to an embodiment, the hole 212-Hc may be formed on a side of the exhaust unit 210c (e.g., the insertion unit 212c).

An end END of the exhaust unit 210c (e.g., the insertion unit 212c) may be formed to be positioned higher than the height of the contents CNT stored in the storage container 100c when the storage container 100c is reversed, in a state in which the exhaust unit 210c (e.g., the insertion unit 212c) is inserted into the storage container 100c as much as possible.

According to an embodiment, as the internal gas of the storage container 100c is exhausted through the exhaust unit 210c, a region of contact between the storage container 100c and the cap 110c is compressed to maintain airtightness that prevents the internal gas from leaking out. For example, when the exhausting is performed until the inside of the storage container 100c is in a vacuum state, the region of contact between the storage container 100c and the cap 110c may be compressed to maintain the vacuum state.

According to an embodiment, the exhaust unit 210c is formed as a conductor, and thus, as the external electrode 330c comes into contact with at least a portion (e.g., the contact unit 213c) of the exhaust unit 210c, the exhaust unit 210c may operate as a ground electrode or a power supply electrode. In this case, as an electrode constituting a set with a ground electrode or a power supply electrode, or a ground electrode is arranged outside the storage container 100c, plasma may be generated in the storage container 100c to perform surface treatment of the contents CNT.

According to an embodiment, the exhaust unit 210c (e.g., the passage 212-PHc of a protrusion 212c) may include a filter FLT for preventing movement of the contents CNT when the contents CNT are sucked together in a process of exhausting the internal air of the storage container 100c. According to an embodiment, the arrangement position of the filter FLT may be variously changed, and in some cases, the filter FLT may be arranged in the hole 212-Hc of the protrusion 212c to prevent the contents CNT from being introduced from the beginning.

According to another embodiment, the filter FLT may be arranged in an inner contact groove 215c.

The contact unit 213c may include the inner contact groove 215c therein. At least a portion of an inner surface of the inner contact groove 215c may be in contact with the external electrode 330c.

According to an embodiment, a protrusion 216c may be formed in the inner contact groove 215c to be in contact with the external electrode 330c.

Referring to FIG. 25 together, the inner angle b1 of the insertion groove formed by the protrusion 216c may be greater than the inner angle b2 of the tip of the external electrode 330c.

In this case, the external electrode 330c is inserted, to a certain depth, into the insertion groove formed by the protrusion 216c, and then is caught by and comes into contact with a lower surface 216-1c of the protrusion 216c.

According to an embodiment, the size of the inner angle b1 of the insertion groove formed by the protrusion 216c may be set such that the side of the external electrode 330c is in contact with the protrusion 216c. That is, the protrusion 216c may be implemented such that the side of the external electrode 330c may be stably in contact with the contact unit 213c while preventing the tip of the external electrode 330c from being damaged due to contact with other members.

According to an embodiment, the inner angle b1 of the insertion groove may equal to the inner angle b2 of the tip.

Because the protrusion 216c comes into line or surface contact with the side of the external electrode 330c, even when there is a slight error in the degree of insertion of the external electrode 330c, a voltage may be applied through stable contact. That is, the side of the external electrode 330c may come into line contact or surface contact with the protrusion 216c.

Referring back to FIG. 24, the body unit 220c may be coupled to the exhaust unit 210c to fix the exhaust unit 210c.

The first airtight unit 230c for sealing the lower surface of the contact unit 213c may be formed at a lower portion of the contact unit 213c.

The first airtight unit 230c may be implemented with a material such that, when the first airtight unit 230c is penetrated by the external electrode 330c, and then the external electrode 330c exits therefrom after the surface treatment of the contents CNT is completed, the first airtight unit 230c restores its original shape to make the penetrated portion airtight.

According to an embodiment, the first airtight unit 230c may be formed of an elastic material.

Plasma Treatment Container According to the
Fourth Embodiment of the Present Disclosure Hereinafter, a plasma treatment container according to the fourth embodiment of the present disclosure will be described.

FIG. 26 is a cross-sectional view of the plasma treatment container according to the fourth embodiment of the present disclosure.

Referring to FIG. 26, unlike the plasma treatment container 200c of FIG. 24, a plasma treatment container 200Ac according to the fourth embodiment of the present disclosure has a structure that is coupled to the storage container 100c after removing the cap 110c of the storage container 100c.

The plasma treatment container 200Ac may include an insertion unit 212Ac, a sealing unit 220-1c, the contact unit 213c, and a body unit 220-2c.

The insertion unit 212Ac is formed to protrude to be inserted into the storage container 100c.

The insertion unit 212Ac may have a hole 212A-Hc and a passage 212A-PHc for exhausting the internal gas of the storage container 100c while being inserted into the storage container 100c.

According to an embodiment, the insertion unit 212Ac may further include a prevention unit 212A-SHc for preventing the contents CNT in the storage container 100c from flowing into the hole 212A-Hc of the insertion unit 212Ac.

According to an embodiment, the prevention unit 212A-SHc may be formed of a dielectric material.

According to another embodiment, the prevention unit 212A-SHc may be formed of a metal and thus operate as a ground electrode or a power supply electrodes together with the insertion unit 212Ac.

According to another embodiment, the prevention unit 212A-SHc may be formed of a metal material when electrically connected to the insertion unit 212Ac or the contact unit 213c, and the prevention unit 212A-SHc may be formed of a dielectric material when not electrically connected to the insertion unit 212Ac or the contact unit 213c.

According to an embodiment, the tip of the prevention unit 212A-SHc may be positioned higher than the tip of the insertion unit 212Ac.

The sealing unit 220-1c is formed to seal the inlet of the storage container 100c in a state in which the cap 110c of the storage container 100c is removed.

According to an embodiment, the sealing unit 220-1c may be formed of a metal material. In this case, a second airtight unit 240c may be further included in at least a portion of a region in which the sealing unit 220-1c and the storage container 100c are in contact with each other. According to an embodiment, the second airtight unit 240c may be formed of an elastic material.

According to an embodiment, as the internal gas of the storage container 100c is exhausted, a region of contact between the storage container 100c and the sealing unit 220-1c is compressed to maintain airtightness that prevents the internal gas from leaking out. For example, when the exhausting is performed until the inside of the storage container 100c is in a vacuum state, the region of contact between the storage container 100c and the sealing unit 220-1c may be compressed to maintain the vacuum state.

According to an embodiment, the sealing unit 220-1c may further include a third airtight unit 242c. For example, the third airtight unit 242c may be formed of an elastic material and in a ring shape, to be fixed in the circumferential direction of the sealing unit 220-1c. For example, the third airtight unit 242c may be formed as an O-ring.

According to an embodiment, a protruding guide unit 221c may be formed on the upper surface of the sealing unit 220-1c to stably fix the inlet of the storage container 100c to the sealing unit 220-1c. The guide unit 221c may be formed to correspond to the shape of the inlet of the storage container 100c. The contact unit 213c has substantially the same structure as that of the contact unit 213c of FIG. 24, and the body unit 220-2c may have substantially the same structure as that of the body unit 220c of FIG. 24.

The insertion unit 212Ac may constitute an exhaust unit together with the contact unit 213c.

According to an embodiment, the sealing unit 220-1c and the body unit 220-2c may be implemented as separated units to be combined with each other, or may be initially implemented as a single integrated unit.

Plasma Treatment Container According to the Fifth Embodiment of the Present Disclosure Hereinafter, a plasma treatment container according to the fifth embodiment of the present disclosure will be described.

FIG. 27 is a cross-sectional view and an exploded view of the plasma treatment container according to the fifth embodiment of the present disclosure.

Referring to FIG. 27, like the plasma treatment container 200Ac according to the fourth embodiment of the present disclosure of FIG. 26, a plasma treatment container 200Bc according to the fifth embodiment of the present disclosure may have a structure that is coupled to the storage container 100c after removing the cap 110c of the storage container 100c.

The plasma treatment container 200Bc may include an exhaust unit 210Bc, a first body unit 220-1Bc, a second body unit 220-2Bc, a first airtight unit 230Bc, the second airtight unit 240c, and the third airtight unit 242c.

The exhaust unit 210Bc may include an insertion unit 212Bc and a contact unit 213Bc.

The insertion unit 212Bc has a structure without the prevention unit 212A-SHc of FIG. 26, and a prevention unit (not shown) may be added thereto according to an embodiment.

The insertion unit 212Bc may also perform the function of the sealing unit 220-1c of FIG. 26. A portion of the insertion unit 212Bc may be coupled to the first body unit 220-1Bc, and a portion protruding from the first body unit 220-1Bc may be inserted into the inlet of the storage container 100c to maintain airtightness.

According to an embodiment, a plurality of holes 212B-Hc for exhausting the internal air of the storage container 100c may be formed in the insertion unit 212Bc. For example, all of the plurality of holes 212B-Hc may be formed on a side of the insertion unit 212Bc.

The contact unit 213Bc may have the same structure as that of the contact unit 213c of FIG. 26, and a detailed structure thereof is omitted in FIG. 26 for convenience of description.

The first body unit 220-1Bc is formed to be in close contact with the storage container 100c so as to seal the inlet of the storage container 100c in a state in which the cap 110c of the storage container 100c is removed.

The second airtight unit 240c and the third airtight unit 242c may have substantially the same structure and function as those of the second airtight unit 240c and the third airtight unit 242c of FIG. 26, respectively.

The second body unit 220-2Bc may be coupled to the first body unit 220-1Bc to fix the exhaust unit 210Bc therein.

According to an embodiment, a first airtight unit 230-Bc may be formed on the upper surface of the second body unit 220-2Bc. The first airtight unit 230-Bc is arranged inside a structure in which the first body unit 220-1Bc and the second body unit 220-2Bc are coupled to each other, and, when pressed by the exhaust unit 210Bc and thus fixed, may stably maintain its initial arrangement state even when the external electrode 330c is inserted and penetrates the first airtight unit 230-Bc.

According to an embodiment, the first airtight unit 230Bc may be implemented with a material such that, when the first airtight unit 230Bc is penetrated by the external electrode 330c, and then the external electrode 330c exits therefrom after the surface treatment of the contents CNT is completed, the first airtight unit 230Bc restores its original shape to make the penetrated portion airtight.

According to an embodiment, the first airtight unit 230Bc may be formed of an elastic material.

Plasma Treatment Apparatus According to the Sixth Embodiment

Hereinafter, a plasma treatment apparatus according to the fifth embodiment will be described.

FIGS. 28 and 29 are diagrams for describing a process of performing surface treatment after an external electrode is inserted into a plasma treatment container of the plasma treatment apparatus according to the sixth embodiment.

Referring to FIGS. 28 and 29, a plasma treatment apparatus 1000c according to the fifth embodiment of the present disclosure may include the plasma treatment container 200c, an accommodation unit 320c, a first electrode unit 321c, a dielectric unit 322c, a second electrode unit 330c, a driving unit 340c, an insulation unit 342c, a power supply unit 350c, a current measurement unit 352c, and a power control unit 354c.

According to an embodiment, the accommodation unit 320c, the first electrode unit 321c, the dielectric unit 322c, the second electrode unit 330c, the driving unit 340c, the insulation unit 342c, the power supply unit 350c, the current measurement unit 352c, and the power control unit 354c may be implemented as a separate plasma treatment apparatus.

Although the plasma treatment container 200c is briefly illustrated in FIGS. 28 and 29 for convenience of description, the plasma treatment container 200c may be the plasma treatment container 200c illustrated in FIG. 24 or the plasma treatment container 200Ac illustrated in FIG. 26.

The accommodation unit 320c provides a space for accommodating the plasma treatment container 200c coupled to the storage container 100c.

The accommodation unit 320b may include the first electrode unit 321c and the dielectric unit 322c arranged adjacent to the outer circumferential surface of the storage container 100c.

The first electrode unit 321c may be connected to the power supply unit 350c to function as a ground electrode or a power supply electrode.

The dielectric unit 322c may be made of a dielectric material and included in the accommodation unit 320c to increase the effect of plasma barrier discharge, but the dielectric unit 322c may not be included according to an embodiment.

According to an embodiment, the dielectric unit 322c may be formed to be closer to the storage container 100c than is the first electrode unit 321c.

The second electrode unit 330c may refer to the same component as the external electrode 330c of FIGS. 24 and 26.

The second electrode unit 330c may be inserted into the plasma treatment container 200c such that a side of the second electrode unit 330c comes into contact with the contact unit (213c of FIG. 24C or 26) of the plasma treatment container 200c. Accordingly, the second electrode unit 330c may apply a power electrode voltage or a ground electrode voltage to the insertion unit (212c of FIG. 24 or 212Ac of FIG. 26) through the contact unit 213c.

The driving unit 340c may control movement of the second electrode unit 330c, for example, movement in a vertical direction.

According to an embodiment, the driving unit 340c may use sensing information collected from a lower limit sensor and an upper limit sensor such that the second electrode unit 330c may move a predetermined distance through a predetermined path.

According to an embodiment, the driving unit 340c may include a motor for moving the second electrode unit 330c.

According to another embodiment, the driving unit 340c may be replaced with a nonpowered elastic material. In this case, the position of the second electrode unit 330c is fixed through the elastic material, and when the plasma treatment container 200c coupled to the storage container 100c is inserted into the accommodation unit 320c, the second electrode unit 330c may be inserted into the plasma treatment container 200c by using the restoring force of the elastic material. For example, the driving unit 340c may include a spring having a certain elasticity.

The insulation unit 342c may maintain insulation between the second electrode unit 330c made of a material through which electricity flows, and another component (e.g., the driving unit 340c).

The power supply unit 350c may operate a protrusion 212c as a ground electrode or a power supply electrode through the second electrode unit 330c, and may operate the first electrode unit 321c as a power supply electrode or a ground electrode opposite to the second electrode unit 330c. That is, the power supply unit 350c may apply power to generate plasma for surface treatment of contents of the storage container 100c.

The current measurement unit 352c may monitor a current provided by the power supply unit 350c and transmit information about the monitored current to the power control unit 354c.

The power control unit 354c may control supplied power by using the information about the monitored current transmitted from the current measurement unit 352c.

Plasma Treatment Method According to the Third Embodiment of the Present Disclosure Hereinafter, a plasma treatment method according to the third embodiment of the present disclosure will be described.

FIG. 30 is a flowchart of the plasma treatment method according to the third embodiment of the present disclosure.

Referring to FIGS. 24 to 30, according to the plasma treatment method according to the third embodiment of the present disclosure, the exhaust unit 210c may be inserted into the storage container 100c (S710c).

According to an embodiment, while the cap 110c of the storage container 100c is closed, the exhaust unit 210c (e.g., the insertion unit 212c of the exhaust unit) may be inserted into the storage container 100c while penetrating the cap 110c.

According to another embodiment, after the cap 110c of the storage container 100c is removed, the exhaust unit (e.g., the insertion unit 212Ac of the exhaust unit) may be inserted into the storage container 100c, as the plasma treatment container 220Ac is coupled to the storage container 100c.

Next, the internal gas of the storage container 100c may be exhausted through the passage 212-PHc or 212A-PHc formed in the inserted exhaust unit 210c (S720c).

Finally, after bringing the external electrode 330c (e.g., an external ground electrode or an external power supply electrode) into contact with the exhaust unit 210c (e.g., the contact unit 213c of the exhaust unit 210c), surface treatment may be performed on the contents (S730c).

According to an embodiment, the stored contents CNT may be surface-treated by generating plasma inside the storage container 100c.

The plasma treatment container according to an embodiment of the present disclosure may include an exhaust unit, which is formed to be inserted into a storage container for storing contents, and has a passage for exhausting internal gas of the storage container while being inserted into the storage container, and a body unit coupled to the exhaust unit to fix the exhaust unit.

According to an embodiment, a tip of the exhaust unit may be formed to be positioned higher than the height of the stored contents when the storage container 100c is reversed, in a state in which the exhaust unit is inserted into the storage container as much as possible.

According to an embodiment, the exhaust unit may have a hole formed on a side thereof for exhausting the internal gas of the storage container.

According to an embodiment, the exhaust unit may be formed as a conductor, and may operate as a ground electrode or a power supply electrode while being inserted into the storage container.

According to an embodiment, as the exhaust unit operates as a ground electrode or a power supply electrode after the internal gas of the storage container is exhausted through the exhaust unit, the contents may be surface-treated.

According to an embodiment, the exhaust unit may include an insertion unit formed to protrude to be inserted into the storage container, and a contact unit formed to be in contact with an external ground electrode or an external power supply electrode.

According to an embodiment, as at least a portion of the inner surface of an inner contact groove of the contact unit is in contact with the external ground electrode or the external power supply electrode, the exhaust unit may operate as the ground electrode or the power supply electrode.

According to an embodiment, a protrusion for contacting the external ground electrode or the external power supply electrode may be formed on the inner surface of the inner contact groove of the contact unit.

According to an embodiment, the protrusion may come into line contact or surface contact with the external ground electrode or the external power supply electrode.

According to an embodiment, the plasma treatment container may further include an airtight unit for making airtight the lower surface of the contact unit.

According to an embodiment, when the airtight unit is penetrated by the external ground electrode or the external power supply electrode and then the surface treatment of the contents is completed, the airtight unit may restore its original shape to make the penetrated portion airtight.

According to an embodiment, the airtight unit may be formed of an elastic material.

According to an embodiment, the exhaust unit may further include a filter that prevents movement of the contents.

According to an embodiment, the exhaust unit may be formed to penetrate at least a portion of the storage container.

According to an embodiment, the exhaust unit may be formed to penetrate a region of the storage container, which is formed of an elastic material.

According to an embodiment, the exhaust unit may include a sealing unit formed to seal the inlet of the storage container in a state in which the cap of the storage container is removed, an insertion unit formed to protrude to be inserted into the storage container, and a contact unit formed to be in contact with an external ground electrode or an external power supply electrode.

According to an embodiment, the sealing unit may be formed of a metal material, and may further include an airtight unit, which is formed of an elastic material and arranged in a region in which the sealing unit and the storage container come into contact with each other.

The plasma treatment method according to an embodiment of the present disclosure may include inserting an exhaust unit into a storage container for storing contents, exhausting internal gas of the storage container through a passage formed in the inserted exhaust unit, and, after bringing an external ground electrode or an external power supply electrode into contact with the exhaust unit, performing surface treatment on the contents.

Plasma Treatment Method According to the Fourth Embodiment of the Present Disclosure Hereinafter, a plasma treatment method according to the fourth embodiment of the present disclosure will be described.

FIG. 31 is a flowchart of the plasma treatment method according to the fourth embodiment of the present disclosure.

The plasma treatment method according to the fourth embodiment of the present disclosure includes, exhausting internal air of a container in which a target object is accommodated, by operating a pump connected to a pump valve in a state in which the pump valve is open (S810), when the internal air of the container is exhausted and the pressure of the internal air of the container reaches a preset reference pressure, applying electric power for generating plasma to the container (S820), closing the pump valve (S830), exhausting again the internal air of the container by operating the pump in a state in which the pump valve is open (S840), when the internal air of the container is exhausted and the pressure of the internal air of the container reaches the reference pressure, closing the pump valve (S850), exhausting again the internal air of the container by operating the pump in a state in which the pump valve is open, (S860), when the internal air of the container is exhausted and the pressure of the internal air of the container reaches the reference pressure, continuously exhausting the internal air of the container by operating the pump in a state in which the pump valve open, such that the pressure of the internal air of the container is maintained to be equal to the reference pressure (S870).

In operation S810, the internal air of the container in which the target object is accommodated is exhausted by operating the pump connected to the pump valve in a state in which the pump valve is open.

In operation S820, when the internal air of the container is exhausted and the pressure of the internal air of the container reaches the preset reference pressure, the electric power for generating plasma is applied to the container.

As described above, as the plasma treatment is performed by applying the electric power while exhausting the internal air of the container, foreign substances inside the container, such as hydrocarbon, are removed, and thus, the plasma treatment efficiency increases.

In operation S830, the pump valve is closed. In this case, the operation of an exhaust pump may be stopped.

As described above, as the pump valve is closed, the exhausting of the internal air of the container is stopped. Therefore, the ozone concentration of the internal air of the container is maintained or increased to improve sterilization performance, and accordingly, plasma treatment and sterilization may be simultaneously performed on the target object.

In addition, as the pump valve is closed, the pressure of the internal air of the container gradually increases. That is, by closing the pump valve, the pressure of the internal air of the container becomes greater than the preset reference pressure.

In operation S840, the pump is operated in a state in which the pump valve is open, to exhaust again the internal air of the container.

Operation S840 may be performed when a first preset closing time period has elapsed after operation S830 is performed, or when the pressure of the internal air of the container reaches a preset first threshold pressure.

For example, when 40 seconds (in this case, 40 seconds is the preset first closing time period) has elapsed after operation S830 is performed, operation S840 may be performed to exhaust the internal air of the container.

As described above, as the plasma treatment is performed by applying the electric power while exhausting the internal air of the container, foreign substances inside the container, such as hydrocarbon, are removed, and thus, the plasma treatment efficiency increases.

In operation S850, when the internal air of the container is exhausted and the pressure of the internal air of the container reaches the reference pressure, the pump valve is closed. In this case, the operation of the exhaust pump may be stopped.

As described above, as the pump valve is closed, the exhausting of the internal air of the container is stopped. Therefore, the ozone concentration of the internal air of the container is maintained or increased to improve sterilization performance, and accordingly, plasma treatment and sterilization may be simultaneously performed on the target object.

In addition, as the pump valve is closed, the pressure of the internal air of the container gradually increases. That is, by closing the pump valve, the pressure of the internal air of the container becomes greater than the preset reference pressure.

In operation S860, the pump is operated in a state in which the pump valve is open, to exhaust again the internal air of the container.

Operation S860 may be performed when a second preset closing time period has elapsed after operation S850 is performed, or when the pressure of the internal air of the container reaches a preset second threshold pressure.

For example, when 30 seconds (in this case, 30 seconds is the preset second closing time period) has elapsed after operation S850 is performed, operation S860 may be performed to exhaust the internal air of the container.

As described above, as the plasma treatment is performed by applying the electric power while exhausting the internal air of the container, foreign substances inside the container, such as hydrocarbon, are removed, and thus, the plasma treatment efficiency increases.

Operations S850 and S860 described above may be repeatedly performed several times.

In operation S870, when the internal air of the container is exhausted and the pressure of the internal air of the container reaches the reference pressure, the internal air of the container is continuously exhausted by operating the pump in a state in which the pump valve open, such that the pressure of the internal air of the container is maintained to be equal to the reference pressure.

In this case, by measuring the pressure of the internal air by using a pressure sensor or the like and adjusting the exhaust force of the pump according to the measured pressure or adjusting the degree of opening the pump valve, the pressure of the internal air may be maintained at a constant pressure, that is, the reference pressure.

Operation S870 may be performed for a preset pressure holding duration.

For example, operation S870 may be performed for 25 seconds (in this case, 25 seconds is the preset pressure holding duration).

In some embodiments, a relationship of 'first closing time period>second closing time period>pressure holding duration' may be satisfied.

As described above, in the plasma treatment method according to the fourth embodiment of the present disclosure, by closing the pump valve in operations S830 and S850 to maintain or raise the ozone concentration and thus improve the sterilizing power on the target object, and finally removing again foreign substances, such as hydrocarbon, in operation S870, sterilization treatment may be effectively performed simultaneously with the plasma treatment.

PRIOR ART DOCUMENTS

Patent Documents (Patent Document 1) Korean Patent Publication No. 2014-0101261

(Patent Document 2) Korean Patent Publication No. 2018-0015057

(Patent Document 3) Korean Patent Publication No. 2018-0015054

(Patent Document 4) Korean Patent Registration No. 10-1439344

(Patent Document 5) Korean Patent Registration No. 10-1693335

EXPLANATION OF REFERENCE NUMERALS DESIGNATING THE MAJOR ELEMENTS OF THE DRAWINGS

110: container 111: target object
120: accommodation unit 130: exhaust unit
140: power supply unit 141: first electrode unit
142: second electrode unit
110a: target object 120a: fixing unit
130a: cover 200a: contact unit
100b: plasma treatment container 110b: implant body
120b: fixing unit 130b: cover
140b: sealing member 150b: display unit
100c: storage container 200c: plasma treatment container
210c: exhaust unit 220c: body unit
230c: airtight unit

The invention claimed is:

1. A plasma treatment apparatus comprising:
an accommodation unit to accommodate a container in which a target object is accommodated;
a first electrode unit in contact with the target object;
a second electrode unit adjacent to an outer circumferential surface of the container; and
a power supply unit to apply a voltage to the target object through the first electrode unit to generate plasma in the container,
wherein the first electrode unit comprises a contact unit configured to be electrically connected to the target object, the contact unit having a tip configured to penetrate an outer surface of the container and an air flow path for exhausting internal air from the container.

2. The plasma treatment apparatus of claim 1, wherein the accommodation unit is provided with an insertion groove into which the container is inserted and accommodated, and the second electrode unit is provided inside a sidewall of the insertion groove.

3. The plasma treatment apparatus of claim 2, wherein upper and lower lengths of the target object are less than or equal to upper and lower lengths of the second electrode unit, such that upper and lower regions of the target object are located within upper and lower regions of the second electrode unit, respectively, when the plasma is generated in the container.

4. The plasma treatment apparatus of claim 1, further comprising a dielectric between the container and the second electrode unit.

5. The plasma treatment apparatus of claim 1, further comprising an exhaust unit connected to the accommodation unit to exhaust internal air of the container, wherein the exhaust comprises:

a path generation unit to generate a path communicating with an inside of the container; and a pump to exhaust the internal air of the container through the path.

6. The plasma treatment apparatus of claim 5, wherein the path generation unit comprises a needle to generate the path by piercing one surface of the container.

7. The plasma treatment apparatus of claim 1, wherein the contact unit is configured to be inserted into the container such that a side of the contact unit is electrically connected to the target object.

8. The plasma treatment apparatus of claim 1, wherein the accommodation unit reads information of a display unit provided in the container, and determines, through the display unit provided in the container, at least one of whether the container is accurately accommodated in a target position, whether the container is a genuine product, the number of times the container is used for plasma treatment, a type of the container, and a type of the target object accommodated in the container.

9. The plasma treatment apparatus of claim 1, wherein the accommodation unit reads information of a display unit provided in the container to determine an internal environment of the container, and the power supply unit applies a voltage by varying a voltage condition according to the determined internal environment.

10. A plasma treatment apparatus comprising:

first and second accommodation units to accommodate first and second containers in which first and second target objects are accommodated, respectively;

an independent exhaust unit, which is connected to each of the first and second accommodation units and comprises an exhaust pump and a pump valve to exhaust internal air of the first and second containers; and first and second treatment units to apply electric power for generating plasma, respectively to the first and second containers from which the internal air is exhausted by the independent exhaust unit, wherein the first treatment unit comprises a first electrode unit configured to be electrically connected to the first target object and a second electrode unit electrically grounded and configured as a first needle to generate a first path exhausting internal air from the first container, and wherein the second treatment unit comprises a first electrode unit configured to be electrically connected to the second target object and a second electrode unit electrically grounded and configured as a second needle to generate a second path exhausting internal air from the second container.

11. The plasma treatment apparatus of claim 10, further comprising:

a housing, which surrounds the first and second accommodation units and packs the first and second accommodation units to be independent of the independent exhaust unit; and a connection unit to connect the housing to the independent exhaust unit such that the housing and the independent exhaust unit are arranged independently of each other.

12. The plasma treatment apparatus of claim 11, further comprising:

a first path generation unit, which comprises the first needle to generate the first path for exhausting the internal air of the first container, by piercing one surface of the first container, and is connected to the connection unit; and a second path generation unit, which comprises the second needle to generate the second path for exhausting the internal air of the second container, by piercing one surface of the second container, and is connected to the connection unit.

13. The plasma treatment apparatus of claim 10, wherein the first and second treatment units simultaneously or separately apply the electric power to the first and second containers, respectively, such that the first and second target objects are simultaneously or separately plasma-treated.

*    *    *    *    *